(12) United States Patent
Ferreira et al.

(10) Patent No.: US 10,099,981 B2
(45) Date of Patent: Oct. 16, 2018

(54) METHODS FOR META-ARYLATION OF AROMATIC ALCOHOLS

(71) Applicant: The University of Georgia Research Foundation, Inc., Athens, GA (US)

(72) Inventors: Eric Ferreira, Athens, GA (US); Qiankun Li, Taihe (CN)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 15/809,305

(22) Filed: Nov. 10, 2017

(65) Prior Publication Data

US 2018/0065909 A1   Mar. 8, 2018

Related U.S. Application Data

(63) Continuation-in-part of application No. 15/088,014, filed on Mar. 31, 2016, now Pat. No. 10,005,719.

(60) Provisional application No. 62/141,093, filed on Mar. 31, 2015.

(51) Int. Cl.

| | |
|---|---|
| *C07C 41/18* | (2006.01) |
| *C07C 269/06* | (2006.01) |
| *C07C 67/333* | (2006.01) |
| *C07D 209/08* | (2006.01) |
| *C07C 201/12* | (2006.01) |
| *C07D 317/60* | (2006.01) |
| *C07C 45/67* | (2006.01) |
| *C07C 67/31* | (2006.01) |
| *C07C 41/28* | (2006.01) |
| *C07C 45/64* | (2006.01) |

(52) U.S. Cl.
CPC .............. *C07C 41/18* (2013.01); *C07C 41/28* (2013.01); *C07C 45/64* (2013.01); *C07C 45/673* (2013.01); *C07C 67/31* (2013.01); *C07C 67/333* (2013.01); *C07C 201/12* (2013.01); *C07C 269/06* (2013.01); *C07D 209/08* (2013.01); *C07D 317/60* (2013.01); *C07C 2603/86* (2017.05)

(58) Field of Classification Search
CPC ...................................... C07C 41/18
USPC ...................................... 546/116
See application file for complete search history.

(56) References Cited

PUBLICATIONS

Li et al Chem. Eur.J.2017, 23,11519-11523.*
Ackermann et al., "Ruthenium-Catalyzed C—H Bond Arylations of Arenes Bearing Removable Directing Groups via Six-Membered Ruthenacycles," Organic Letters, 2012, 14(4): 1154-1157.
Alberico et al., "Aryl-Aryl Bond Formation by Transition-Metal-Catalyzed Direct Arylation," Chem. Rev., 2007, 107: 174-238.
Alsters et al., "Rigid Five- and Six-Membered C,N,N'-Bound Aryl, Benzyl, and Alkyl Organopalladium Complexes: sp2 vs sp3 C—H Activation during Cyclopalladation and Palladium(IV) Intermediates in Oxidative Addition Reactions with Dihalogens and Alkyl Halides," Organometallics, 1993, 12: 1831-1844.
Arockiam et al., "Ruthenium(II)-Catalyzed C—H Bond Activation and Functionalization," Chem. Rev., 2012, 112:5879-5918.
Ashenhurst JA, "Intermolecular oxidative cross-coupling of arenes," Chem. Soc. Rev., 2010, 39: 540-548.
Bedford et al., "The Catalytic Intermolecular Orthoarylation of Phenols," Angew. Chem. Int. Ed., 2003, 42(1): 112-114.
Breit and Rousseau, "Removable Directing Groups in Organic Synthesis and Catalysis," Angew. Chem. Int. Ed., 2011, 50: 2450-2494.
Carrión and Cole-Hamilton, "Halide-free ethylation of phenol by multifunctional catalysis using phosphinite ligands," Chem. Commun., 2006, 4527-4529.
Chen and Shi, "Sulfonamide-Promoted Palladium(II)-Catalyzed Alkylation of Unactivated Methylene C(sp3)-H Bonds with Alkyl Iodides," Angew. Chem. Int. Ed., 2014, 53: 11950-11954.
Chu et al., "Palladium(II)-Catalyzed Ortho Arylation of 2-Phenoxypyridines with Potassium Aryltrifluoroborates via C—H Functionalization," Organometallics, 2010, 29: 4058-4065.
Chu et al., "Remote Meta-C—H Activation Using a Pyridine-Based Template: Achieving Site-Selectivity via the Recognition of Distance and Geometry," ACS Cent. Sci., 2015, 1: 394-399.
Colby et al., "Rhodium-Catalyzed C—C Bond Formation via Heteroatom-Directed C—H Bond Activation," Chem. Rev., 2010: 624-655.
Cong et al., "2-Pyridylmethyl ether: a readily removable and efficient directing group for amino acid ligand accelerated orth-C—H olefination of phenols," ChemComm, 2013, 49: 662-664.
Corbet and De Campo, "8-Aminoquinoline: A Powerful Directing Group in Metal-Catalyzed Direct Functionalization of C—H Bonds," Angew. Chem. Int. Ed., 2013, 52: 9896-9898.
Dai et al., "Pd(II)-Catalyzed ortho- or meta-C—H Olefination of Phenol Derivatives," J. Am. Chem. Soc., 2013, 135: 7567-7571.
Deng and Yu, "Remote meta-C—H Olefination of Phenylacetic Acids Directed by a Versatile U-Shaped Template," Angew. Chem. Int. Ed., 2015, 54: 888-891.
Engle et al., "Ligand-Accelerated C—H Activation Reactions: Evidence for a Switch of Mechanism," J. Am. Chem. Soc., 2010, 132: 14137-14151.

(Continued)

*Primary Examiner* — Nizal S Chandrakumar
(74) *Attorney, Agent, or Firm* — Thomas | Horstemeyer, LLP

(57) ABSTRACT

Provided are methods for the meta-selective C—H arylations of arene alcohol-based substrates. The methods combine the transient norbornene strategy with a quinoline-based acetal scaffold to achieve the formation of biaryl compounds. These processes establish a foundation for catalytic polyfunctionalization of alcohol-based compounds. The method comprises attaching a heterocyclic hemiacetal scaffold to an aromatic alcohol or a substituted aromatic alcohol; reacting the aromatic or substituted aromatic alcohol having the heterocyclic hemiacetal scaffold attached with an alkyl or aryl iodide in a reaction mix comprising a palladium catalyst, a silver salt, and carboxymethyl norbornene to generate a meta-arylated arene conjugated to the heterocyclic hemiacetal scaffold; and then cleaving the heterocyclic hemiacetal scaffold from the meta-arylated arene alcohol.

3 Claims, 6 Drawing Sheets

(56) References Cited

PUBLICATIONS

Engle et al., "Ligand-Accelerated Cross-Coupling of C(sp2)-H Bonds with Arylboron Reagents," J. Am. Chem. Soc., 2011, 133: 18183-18193.

Ferreira EM, "A urrogate for selectivity," Nat. Chem., 2014, 6: 94-96.

Fraunhoffer and White, "syn-1,2-Amino Alcohols via Diastereoselective Allylic C—H Amination," J. Am. Chem. Soc., 2007, 129: 7274-7276.

Gormisky and White, "Synthetic Versatility in C—H Oxidation: A Rapid Approach to Differentiated Diols and Pyrans from Simple Olefins," J. Am. Chem. Soc., 2011, 133: 12584-12589.

Guo et al., "Direct ortho-C—H Functionalization of Aromatic Alcohols Masked by Acetone Oxime Ether via exo-Palladacycle," Org. Lett., 2015, 17: 1802-1805.

Guo et al., "Palladium(II)-Catalyzed Acetoxime Directed ortho-Arylation of Aromatic Alcohols," Chem. Eur. J., 2015, 21: 17474-17478.

Huang et al., "Silanol: A Traceless Directing Group for Pd-Catalyzed o-Alkenylation of Phenols," J. Am. Chem. Soc., 2011, 133: 12406-12409.

Huang et al., "Synthesis of Catechols from Phenols via Pd-Catalyzed Silanol-Directed C—H Oxygenation," J. Am. Chem. Soc., 2011, 133: 17630-17633.

Hussain and Singh, "Synthesis of Biaryls through Aromatic C—H Bond Activation: A Review of Recent Developments," Adv. Synth. Catal., 2014, 356: 1661-1696.

Kandukuri et al., "Diastereotopic Group Selection in Hydroxy-Directed Intramolecular C—H Alkenylation of Indole under Oxidative Palladium(II) Catalysis," Adv. Synth. Catal., 2014, 356: 1597-1609.

Kim et al., "Pd-catalyzed oxidative acylation of 2-phenoxypyridines with alcohols via C—H bond activation," Tetrahedron, 2013, 69: 6552-6559.

Knight et al., "The design of a readily attachable and cleavable molecular scaffold for ortho-selective C—H alkenylation of arene alcohols," Chem. Sci., 2016, 7: 1982-1987.

Lee et al., "Meta-Selective C—H Functionlization Using a Nitrile-Based Directing Group and Cleavable Si-Tether," J. Am. Chem. Soc., 135: 18778-18781.

Leow et al., "Activation of remote meta-C—H bonds assisted by an end-on template," Nature, 2012, 486: 518-522.

Lewis and Smith, "Catalytic C—C Bond Formation via Ortho-Metalated Complexes," J. Am. Chem. Soc., 1986, 108(10): 2728-2735.

Lewis et al., "Preagostic Rh—H Interactions and C—H Bond Functionalization: A Combined Experimental and Theoretical Investigation of Rhodium (I) Phosphinite Complexes," Organometallics, 2005, 24: 5737-5746.

Li et al., "Iridium-Catalyzed Regioselective Silylation of Secondary Alkyl C—H Bonds for the Synthesis of 1,3-Diols," J. Am. Chem. Soc., 2014, 136: 6586-6589.

Liu et al., "Ni(II)/BINOL-Catalyzed alkenylation of unactivated C(sp3)-H bonds," Chem. Commun., 2015, 51: 7899-7902.

Liu et al., "Palladium-Catalyzed Oxidative Olefination of Phenols Bearing Removable Directing Groups under Molecular Oxygen," J. Org. Chem., 2014, vol. 79: 1521-1526.

Lu et al., "Hydroxyl-directed C—H carbonylation enabled by mono-N-protected amino acid ligands: An expedient route to 1-isochromanones," Chem. Sci., 2011, 2: 967-971.

Lu et al., "Pd(II)-Catalyzed Hydroxyl-Directed C—H Olefination Enabled by Monoprotected Amino Acid Ligands," J. Am. Chem. Soc., 2010, 132: 5916-5921.

Lyons and Sanford, "Palldium-Catalyzed Ligand-Dreicted C—H Functionalization Reactions," Chem. Rev., 2010, 110: 1147-1169.

Ma and Ackermann, "Ruthenium(II)-Catalyzed C—H Alkenylations of Phenols with Removable Directing Groups," Chem. Eur. J., 2013, 19: 13925-13928.

McGlacken and Bateman, "Recent advances in aryl-aryl bond formation by direct arylation," Chem. Soc. Rev., 2009, 38: 2447-2464.

Mo et al., "Alcohols or Masked Alcohols as Directing Groups for C—H Bond Functionalization," Chem. Lett., 2014, 43: 264-271.

Morimoto et al., "Synthesis of Isochromene and Related Derivatives by Rhodium-Catalyzed Oxidative Coupling of Benzyl and Allyl Alcohols with Alkynes," J. Org. Chem., 2011, 76: 9548-9551.

Nakanowatari and Ackermann, "Ruthenium(II)-Catalyzed Synthesis of Isochromenes by C—H Activation with Weakly Coordinating Aliphatic Hydroxyl Groups," Chem. Eur. J., 2014, 20: 5409-5413.

Nourry et al., "Synthesis of an analogue fo lavendamycin and of conformationally restricted derivatives by cyclization via a hemiaminal intermediate," Tetrahedrom Letters, 2007, 48: 6014-6018.

Oi et al., "Rhodium-HMPT-catalyzed direct ortho arylation of phenols with aryl bromides," Tetrahedron Letters, 2003, 44: 8665-8668.

Pascual et al., "Palladium catalyzed arylation for the synthesis of polyarenes," Org. Biomol. Chem., 2007, 5: 2727-2734.

Ren et al., "Catalytic Functionalization of Unactivated sp3 C—H Bonds via exo-Directing Groups: Synthesis of Chemically Differentiated 1,2-Diols," J. Am. Chem. Soc., 2012, 134: 16991-16994.

Ren et al., "Catalytic Ortho-Acetoxylation of Masked Benzyl Alcohols via an Exo-Directing Mode," Org. Lett., 2015, 17: 2696-2699.

Rice and White, "Allylic C—H Amination for the Preparation of syn-1,3-Amino Alcohol Motifs," J. Am. Chem. Soc., 2009, 131:11707-11711.

Rit et al., "Pd(II)-Catalyzed ortho-C—H Oxidation of Arylacetic Acid Derivatives: Synthesis of Benzofuranones," Org. Lett., 2014, 16: 968-971.

Rit et al., "Reusable directing groups [8-aminoquinoline, picolinamide, sulfoximine] in C(sp3)-H bond acitivation: presnet and future," Tetrahedron, 2015, 71: 4450-4459.

Shabashov and Daugulis, "Auxiliary-Assisted Palladium-Catalyzed Arylation and Alkylation of sp2 and sp3 Carbon-Hydrogen Bonds," J. Am. Chem. Soc., 2010, 132: 3965-3972.

Simmons and Hartwig, "Catalytic funcitonalization of unactivated primary C—H bonds directed by an alcohol," Nature, 2012, 483:70-73.

Simmons and Hartwig, "Iridium-Catalyzed Arene Ortho-Silylation by Formal Hydroxyl-Directed C—H Activation," J. Am. Chem. Soc., 2010, 132: 17092-17095.

Stache et al., "Molecular scaffolds with remote directing groups for selective apalldium-catalyzed C—H bond functionalizations," Chem. Sci., 2012, 3: 1623-1628.

Thompson et al., "Cyclic Ether Synthesis via Palladium-Catalyzed Directed Dehydrogenative Annulation at Unactivated Terminal Positions," J. Am. Chem. Soc., 2015, 137: 11586-11589.

Wan et al., "Cross-Coupling of Remote meta-C—H Bonds Directed by a U-shaped Template," J. Am. Chem. Soc., 2013, 135: 18056-18059.

Wang and Gevorgyan, "General Method for the Synthesis of Salicylic Acids from Phenols through Palladium-Catalyzed Silanol-Directed C—H Carboxylation," Angew. Chem. Int. Ed., 2015, 54: 2255-2259.

Wang and Huang, "Expanding Structural Diversity; Removable and Manipulable Directing Groups for C—H Activation," SYNLETT 2013, 24: 145-149.

Wang et al., "Pd(II)-Catalyzed Hydoxyl-Directed C—H Acivation/C—O Cyclization: Expedient Construction of Dihydrobenzofurans," J. Am. Chem. Soc., 2010, 132: 12203-12205.

Xiao et al., "Pd(II)-Catalyzed C—H Activation/Aryl-Aryl Coupling of Phenol Esters," J. Am. Chem. Soc., 2010, 132: 468-469.

Xu et al., "Diverse sp3 C—H functionalization through alcohol β-sulfonyloxylation," Nat. Chem., 2015, 7: 829-835.

Yang et al., "Pd(II)-Catalyzed meta-C—H Olefination, Arylation, and Acetoxylation of Indolines Using a U-Shaped Template," J. Am. Chem. Soc., 2014, 136: 10807-10813.

Yeung and Dong, "Catalytic Dehydrogenative Cross-Coupling: Forming Carbon-Carbon Bonds by Oxidizing Two Carbon-Hydrogen Bonds," Chem. Rev., 2011, 111: 1215-1292.

(56) References Cited

OTHER PUBLICATIONS

Zaitsev et al., "Highly Regioselective Arylation of sp3 C—H Bonds Catalyzed by Palladium Acetate," J. Am. Chem. Soc., 2005, 127: 13154-13155.

Zhang and Spring, "Arene C—H functionalisation using a removable/modifiable or a traceless directing group strategy," Chem. Soc. Rev., 2014, 43: 6906-6918.

Zhang et al., "Palladium-Catalyzed Aromatic C—H Bond Nitration Using Removable Directing Groups: Regiospecific Synthesis of Substituted o-Nitrophenols from Related Phenols," J. Org. Chem, 2014, 79: 11508-11516.

Narasimhan et al., "Evidence in Favor of Lithium-Halogen Exchange Being Faster Than Lithium-Acidic Hydrogen (Deuterium) Exchange," J. Am. Chem. Soc., 1990, 112(11): 4431-4435.

Nandhikonda and Heagy, "Dual Fluorescent N-Aryl-2,3-naphthalimides: applications in Ratiometric DNA Detection and White Organic Light-Emitting Devices," Org. Lett., 2010, 12(21): 4796-4799.

Jnaneshwara et al., "Selenium dioxide: a selective oxidising agent for the functionalisation of quinolines," J. Chem. Res. (S), 2000, 34-35.

Li and Ferreira, "Meta-Selective C—H Arylation of Aromatic Alcohols with a Readily Attachable and Cleavable Molecular Scaffold," Chem. Eur. J., 2017, 23(48): 11519-11523.

Li et al., "Palladium(II)-Catalyzed ortho-Arylation of Aromatic Alcohols with a Readily Attachable and Cleavable Molecular Scaffold," Chem. Eur. J., 2016, 22(37): 1521-3765.

\* cited by examiner

*Arylation/Cleavage Procedure*

*Telescoping Procedure*

METHODS FOR META-ARYLATION OF AROMATIC ALCOHOLS

CROSS-REFERENCE TO RELATED APPLICATIONS

This application is a Continuation-in-Part of U.S. application Ser. No. 15/088,014 entitled "METHOD FOR DIRECTED CATALYTIC FUNCTIONALIZATION OF ALCOHOLS" filed Mar. 31, 2016 and claims priority from U.S. Provisional Patent Application Ser. No. 62/141,093 entitled "METHOD FOR DIRECTED CATALYTIC FUNCTIONALIZATION OF ALCOHOLS" filed on Mar. 31, 2015, the disclosures of which are incorporated herein by reference in their entireties.

STATEMENT REGARDING FEDERALLY SPONSORED RESEARCH OR DEVELOPMENT

This invention was made with Government support under contract NSF-CHE-1339674 awarded by the National Science Foundation and the Environmental Protection Agency. The Government has certain rights in the invention.

TECHNICAL FIELD

The present disclosure is generally related to methods of selectively meta-arylating aromatic alcohols.

BACKGROUND

Transition metal-catalyzed site-selective C—H functionalization has been a broad and highly impactful enterprise in the fields of synthetic chemistry and materials science. A primary strategy to achieve site specificity is to employ substrates with directing capabilities that can position the catalytic complex to achieve selective bond functionalization. In terms of $C(sp^2)$-H functionalization, this strategy has been widely executed for ortho-selective processes, as proximity effects are readily achieved. More recently, innovative approaches in directed C—H functionalization have now been achieved to attain meta-selectivity (Yang J. (2015) *Org. Biomol. Chem.* 13: 1930-1941; Dey et al., (2016) *Org. Biomol. Chem.* 14: 5440-5453). Select strategies include designer templates that orient the metal in close proximity to a meta C—H bond (Leow et al., (2012) *Nature* 486: 518-522; Dai et al., (2013) *Am. Chem. Soc.* 135: 7567-7571; Wan et al., (2013) *J. Am. Chem. Soc.* 135: 18056-18059; Lee et al., (2013) *J. Am. Chem. Soc.* 135: 18778-18781; Tang et al., (2104) *Nature* 507: 215-220; Bera et al., (2014) *Org. Lett.* 16: 5760-5763; Deng & Yu (2015) *Angew. Chem. Int. Ed.* 54: 888-891; Deng & Yu (2015) *Angew. Chem.* 127: 902-905; Chu et al., (215) *ACS Cent. Sci.* 1: 394-399; Li et al., (2015) *Chem. Sci.* 6: 5595-5600; Bera et al., (2015) *Angew. Chem. Int. Ed.* 54: 8515-8519; Bera et al., (2015) *Angew. Chem.* 127: 8635-8639; Patra et al., (2016) *Chem. Commun.* 52: 2027-2030; Li et al., (2016) *Nat. Commun.* 7: 10443; Dutta et al., (2017) *ACS Catal.* 7: 3162-3168), steric-controlled processes (Cho et al., (2000) *J. Am. Chem. Soc.* 122: 12868-12869; Cho et al., (2002) *Science* 295: 305-308; Murphy et al., (2007) *J. Am. Chem. Soc.* 129: 15434-15435; Cheng & Hartwig (2014) *Science* 343: 853-857), or transformations that are predicated on a specific mechanistic pathway selective for meta reactivity (Phipps & Gaunt (2009) *Science* 323: 1593-1597; Duong et al., (2011) *Angew. Chem. Int. Ed.* 50: 463-466; Duong et al., (2011) *Angew. Chem.* 123: 483-486; Saidi et al., (2011) *J. Am. Chem. Soc.* 133: 19298-19301; Hofmann & Ackermann (2013) *J. Am. Chem. Soc.* 135: 5877-5884; Martinez-Martinez et al., (2014) *Science* 346: 834-837; Li et al., (2015) *J. Am. Chem. Soc.* 137: 13894-13901 (Phipps & Gaunt (2009) *Science* 323: 1593-1597; Duong et al., (2011) *Angew. Chem. Int. Ed.* 50: 463-466; Duong et al., (2011) *Angew. Chem.* 123: 483-486; Saidi et al., (2011) *J. Am. Chem. Soc.* 133: 19298-19301; Hofmann & Ackermann (2013) *J. Am. Chem. Soc.* 135: 5877-5884; Martinez-Martinez et al., (2014) *Science* 346: 834-837; Li et al., (2015) *J. Am. Chem. Soc.* 137: 13894-13901).

A separate approach using palladium catalysis was developed by the Yu and Dong groups independently (Wang et al., (2015) *Nature* 519: 334-338; Dong et al., (2015) *J. Am. Chem. Soc.* 137: 5887-5890), where they draw inspiration from the Catellani reaction involving norbornene insertion/deinsertion (Catellani et al., (1997) *Angew. Chem. Int. Ed. Engl.* 36: 119-122; Catellani et al., (1997) *Angew. Chem.* 109: 142-145; Della Ca et al., (2016) *Acc. Chem. Res.* 49: 1389-1400) to achieve metalation at the meta position from an initial ortho-directed functionalization, as shown in FIG. 1. Further studies illustrated the capacity of this palladium-catalyzed process to be utilized in derivatives of phenylacetic acids, phenethyl amines, benzyl amines, anilines, and phenols (Shen et al., (2015) *J. Am. Chem. Soc.* 137: 11574-11577; Wang et al., (2016) *J. Am. Chem. Soc.* 138: 9269-9276; Wang et al., (2016) *J. Am. Chem. Soc.* 138: 14092-14099; Shi et al., (2016) *J. Am. Chem. Soc.* 138: 14876-14879; Wang et al., (2017) *Angew. Chem. Int. Ed.* 56: 5125-5129; Wang et al., (2017) *Angew. Chem.* 129: 5207-5211; Li et al., (2017) *Angew. Chem. Int. Ed.* 56: 6874-6877; Li et al., (2017) *Angew. Chem.* 129: 6978-6981; Chen et al., (2017) *Angew. Chem. Int. Ed.* 56: 8183-8186; Chen et al., (2017) *Angew. Chem.* 129: 8295-8298; Han et al., (2016) *Chem. Commun.* 52: 6903-6906; Ding et al., (2017) *J. Am. Chem. Soc.* 139: 417-425; Ling et al., (2017) *Chem. Commun.* 53: 2166-2169).

There has been interest in the catalytic $C(sp^2)$-H functionalization of alcohol-based substrates, namely in the development of molecular scaffolds that can direct a metal species to a specific site (Knight et al., (2016) *Chem. Sci.* 7: 1982-1987; Li et al., (2016) *Chem. Eur. J.* 22: 13054-13058; Simmons & Hartwig (2010) *J. Am. Chem. Soc.* 132: 17092-17095; Lee et al., (2013) *J. Am. Chem. Soc.* 135, 18778-18781; Chu et al., (2015) *ACS Cent. Sci.* 21: 394-399; Guo et al., (2015) *Org. Lett.* 17: 1802-1805; Guo et al., (2015) *Chem. Eur. J.* 21: 17474-17478; Ren et al., (2015) *Org. Lett.* 17, 2696-2699; Chen et al., (2016) *Chem. Commun.* 52: 10241-10244; Shao et al., (2016) *RSC Adv.* 6: 78875-78880; Mo et al., (2014) *Chem. Lett.* 43: 264-271). Some efforts have focused on the design of acetal-based scaffolds that feature pyridyl or quinolinyl groups for the functionalization of arene-based alcohols (Knight et al., (2016) *Chem. Sci.* 7: 1982-1987). These scaffolds are readily covalently attached to alcohols, and when attached will induce ortho-selective Pd-catalyzed C—H alkenylations and arylations. These scaffolds can circumvent some of the challenges encountered in directed functionalizations with alcohol-based substrates (e.g., oxidative decomposition pathways), and the facile attachment, cleavage, and recovery methods for these scaffolds enable straightforward processing and telescoping procedures. These processes were designed for ortho-selective reactivity; an analogous development in meta-functionalizations would significantly expand the scope of this methodology.

SUMMARY

The present disclosure encompasses embodiments of meta-selective C—H arylations of arene alcohol-based substrates. The strategy involves the combination of the transient norbornene strategy with a quinoline-based acetal scaffold to achieve the formation of biaryl compounds. These processes establish a foundation for catalytic polyfunctionalization of alcohol-based compounds.

One aspect of the disclosure, therefore, encompasses embodiments of a method of meta-arylating an arene alcohol, the method comprising the steps of: (a) attaching a heterocyclic hemiacetal scaffold to an aromatic alcohol or a substituted aromatic alcohol; (b) reacting the aromatic or substituted aromatic alcohol having the heterocyclic hemiacetal scaffold attached thereto with an alkyl or aryl iodide in a reaction mix comprising a palladium catalyst, a silver salt, and carboxymethyl norbornene to generate a meta-arylated arene conjugated to the heterocyclic hemiacetal scaffold; and (c) cleaving the heterocyclic hemiacetal scaffold from the meta-arylated arene alcohol.

In some embodiments of this aspect of the disclosure, in step (b) of the method, the reaction mix can further comprise a ligand.

In some embodiments of this aspect of the disclosure, the heterocyclic hemiacetal scaffold can be quinolinyl hemiacetal benzoate.

In some embodiments of this aspect of the disclosure, the aryl iodide can have the formula I:

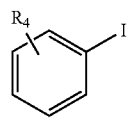

wherein $R_4$ can be selected from the group consisting of: H, a halogen, an alkyl, an alkoxy, a carboxyalkyl, an alkylbenzoate, a substituted amine, an ether, a ketone, an ester, a carbamate, a nitro, and an halogenated alkyl.

In some embodiments of this aspect of the disclosure, the aryl iodide can be an iodoalkylbenzoate.

In some embodiments of this aspect of the disclosure, the iodoalkylbenzoate can be iodomethylbenzoate.

In some embodiments of this aspect of the disclosure, the ligand can be selected from the group consisting of acetylglycine, 3-acetylamino 2-hydroxypyridine, 3-[3-trifluoro 1-amido tetrafluorophenyl] 2-hydroxy pyridine, acetylalanine, acetyl tert-alanine, acetylphenylalanine, acetyl β-alanine, Boc-glycine, formyl-glycine, benzoylglycine, trifluoroacetylglycine, and trifluoroacetyl-β-alanine.

In some embodiments of this aspect of the disclosure, ligand can be trifluoroacetylglycine or trifluoroacetyl-β-alanine.

In some embodiments of this aspect of the disclosure, ligand can be trifluoroacetylglycine.

In some embodiments of this aspect of the disclosure, the palladium catalyst can be palladium acetate or palladium trifluoroacetate.

In some embodiments of this aspect of the disclosure, the palladium catalyst is palladium trifluoroacetate.

In embodiments of this aspect of the disclosure, the silver salt can be silver acetate.

In some embodiments of this aspect of the disclosure, the cleavage of the heterocyclic hemiacetal scaffold from the meta-arylated arene alcohol generates an alkylayted heterocyclic hemiacetal scaffold and the steps (a)-(c) are repeated using the alkylayted heterocyclic hemiacetal scaffold in step (a).

Another aspect of the disclosure encompasses embodiments of a method of meta-arylating an arene alcohol, the method comprising the steps of: (a) attaching a quinolinyl hemiacetal benzoate to an aromatic alcohol or a substituted aromatic alcohol wherein the aromatic alcohol or a substituted aromatic alcohol has the formula II:

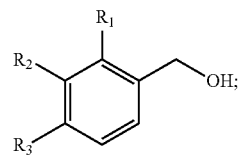

thereby forming form a compound of formula III:

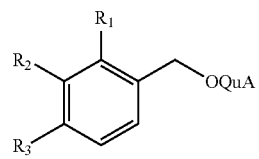

(b) reacting the compound of formula IV with an alkyl or aryl iodide having the formula I:

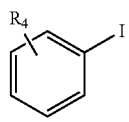

in the presence of a palladium trifluoroacetate catalyst, silver acetate, trifluoroacetylglycine, and carboxymethyl norbornene to generate a meta-arylated arene-quinolinyl hemiacetal scaffold conjugate; and (c) incubating the meta-arylated arene-quinolinyl hemiacetal scaffold conjugate of step (b) with an alkyl alcohol under acid conditions to generate an alkylayted quinolinyl hemiacetal scaffold having the formula VI:

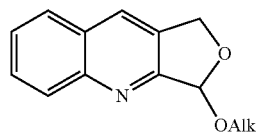

and a meta-arylated arene alcohol having the formula VII.

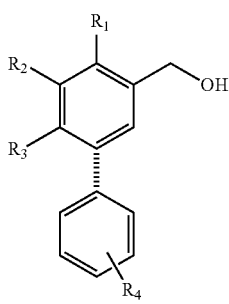

wherein: $R_1$, $R_2$, or $R_3$ can be independently selected from the group consisting of: H, a halogen, an alkyl, a substituted alkyl, an aryl, a substituted aryl, an amino group, a substituted amino group, an alkoxy group, a heterocyclic group, $R_1$ and $R_2$ can be linked to form a cyclic group, and $R_2$ and $R_3$ can be linked to form a cyclic group; and $R_4$ can be selected from the group consisting of: H, a halogen, an alkyl, an alkoxy, a carboxyalkyl, an alkylbenzoate, a substituted amine, an ether, a ketone, an ester, a carbamate, a nitro, and a halogenated alkyl.

In some embodiments of this aspect of the disclosure, the aryl iodide can be an iodoalkylbenzoate.

In some embodiments of this aspect of the disclosure, the iodoalkylbenzoate can be iodomethylbenzoate.

In some embodiments of this aspect of the disclosure, the steps (a)-(c) are repeated wherein the alkylayted quinolinyl hemiacetal scaffold replaces the quinolinyl hemiacetal benzoate scaffold in step (a).

In some embodiments of this aspect of the disclosure, when in the aromatic alcohol having the formula II $R_1$ and $R_2$ are both H, the meta-arylated arene alcohol product of step (b) having the formula VI can be a mono-meta-arylated aromatic alcohol, a di-meta-arylated aromatic alcohol, or a mixture thereof.

BRIEF DESCRIPTION OF THE DRAWINGS

Aspects of the present disclosure will be more readily appreciated upon review of the detailed description of its various embodiments, described below, when taken in conjunction with the accompanying drawings.

DETAILED DESCRIPTION

Figure 1:
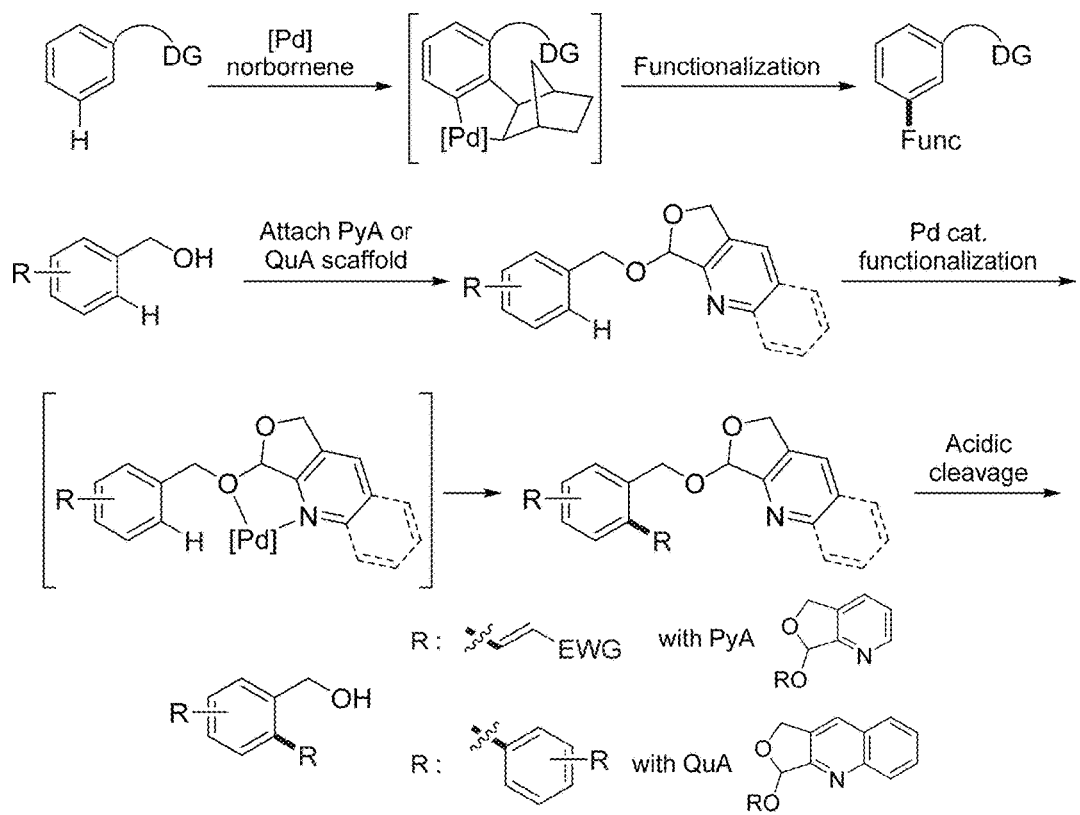
FIG. 1 illustrates a prior art approach to alcohol-based scaffold to direct functionalization (Wang et al., (2015) Nature 519: 334-338; Dong et al., (2015) J. Am. Chem. Soc. 137: 5887-5890; Shen et al., (2015) J. Am. Chem. Soc. 137: 11574-11577; Wang et al., (2016) J. Am. Chem. Soc. 138: 9269-9276; Wang et al., (2016) J. Am. Chem. Soc. 138: 14092-14099; Shi et al., (2016) J. Am. Chem. Soc. 138: 14876-14879; Wang et al., (2017) Angew. Chem. Int. Ed. 56: 5125-5129; Wang et al., (2017) Angew. Chem. 129, 5207-5211; Li et al., (2017) Angew. Chem. Int. Ed. 56: 6874-6877; Li et al., (2017) Angew. Chem. 129: 6978-6981; Chen et al., (2017) Angew. Chem. Int. Ed. 56: 8183-8186; Chen et al., (2017) Angew. Chem. 129: 8295-8298; Han et al., (2016) Chem. Commun. 52: 6903-6906; Ding et al., (2017) J. Am. Chem. Soc. 139: 417-425; Ling et al., (2017) Chem. Commun. 53; 2166-2169).

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, dimensions, frequency ranges, applications, or the like, as such can vary. It is also to be understood that the terminology used herein is for purposes of describing particular embodiments only, and is not intended to be limiting. It is also possible in the present disclosure that steps can be executed in different sequence, where this is logically possible. It is also possible that the embodiments of the present disclosure can be applied to additional embodiments involving measurements beyond the examples described herein, which are not intended to be limiting. It is furthermore possible that the embodiments of the present disclosure can be combined or integrated with other measurement techniques beyond the examples described herein, which are not intended to be limiting.

It should be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

Prior to describing the various embodiments, the following definitions are provided and should be used unless otherwise indicated.

Abbreviations

DMF, Dimethylformamide; NBE-CO$_2$Me, 2-carboxymethylnorbornene; EtOAc, ethyl acetate; Et$_3$N, triethylamine Definitions The term "acetylamino" as used herein refers any primary or secondary amino that is acetylated. Examples of such include, but are not limited to, acetamide and the like.

The term "acyl" as used herein refers to an organic acid group wherein the —OH of the carboxyl group has been replaced with another substituent (i.e., as represented by RCO—, wherein R is an alkyl or an aryl group as defined herein). The term "acyl" specifically includes arylacyl groups, such as an acetylfuran and a phenacyl group. Specific examples of acyl groups include acetyl and benzoyl.

The term "acylamino" as used herein refers to an acyl-NH— group wherein acyl is as previously described.

The term "acyloxyl" as used herein refers to an acyl-O— group wherein acyl is as previously described.

The term "alkenyloxy" as used herein refers to linear or branched oxy-containing radicals having an alkenyl portion of about 2 to 10 carbon atoms, such as an ethenyloxy or propenyloxy radical. An alkenyloxy radical may be a "lower alkenyloxy" radical having about 2 to 6 carbon atoms. Examples of alkenyloxy radicals include without limitation ethenyloxy, propenyloxy, butenyloxy, and isopropenyloxy alkyls. An "alkenyloxy" radical may be substituted with one or more substitutents disclosed herein including halo atoms, such as fluoro, chloro or bromo, to provide "haloalkenyloxy" radicals (e.g. trifluoroethenyloxy, fluoroethenyloxy, difluoroethenyloxy, and fluoropropenyloxy).

The term "alkoxy" as used herein refers to a linear or branched oxy-containing radical having an alkyl portion of one to about ten carbon atoms, such as a methoxy radical, which may be substituted. In aspects of the disclosure an alkoxy radical may comprise about 1-10, 1-8, 1-6 or 1-3 carbon atoms. In embodiments of the disclosure, an alkoxy radical comprises about 1-6 carbon atoms and includes a C$_1$-C$_6$ alkyl-O-radical wherein C$_1$-C$_6$ alkyl has the meaning set out herein. Examples of alkoxy radicals include without limitation methoxy, ethoxy, propoxy, butoxy, isopropoxy, and tert-butoxy alkyls. An "alkoxy" radical may, optionally be substituted with one or more substitutents disclosed herein including alkyl atoms to provide "alkylalkoxy" radicals; halo atoms, such as fluoro, chloro or bromo, to provide "haloalkoxy" radicals (e.g. fluoromethoxy, chloromethoxy, trifluoromethoxy, difluoromethoxy, trifluoroethoxy, fluoroethoxy, tetrafluoroethoxy, pentafluoroethoxy, and fluoropropox) and "haloalkoxyalkyl" radicals (e.g. fluoromethoxymethyl, chloromethoxyethyl, trifluorornethoxymethyl, difluoromethoxyethyl, and trifluorocthoxymethyl).

The term "alkoxycarbonyl" as used herein refers to an alkyl-O—CO— group. Exemplary alkoxycarbonyl groups include methoxycarbonyl, ethoxycarbonyl, butyloxycarbonyl, and t-butyloxycarbonyl.

The term "alkyl", either alone or within other terms such as "thioalkyl" and "arylalkyl", as used herein, means a monovalent, saturated hydrocarbon radical which may be a straight chain (i.e. linear) or a branched chain. An alkyl radical for use in the present disclosure generally comprises from about 1 to 20 carbon atoms, particularly from about 1 to 10, 1 to 8 or 1 to 7, more particularly about 1 to 6 carbon atoms, or 3 to 6. Illustrative alkyl radicals include methyl, ethyl, n-propyl, n-butyl, n-pentyl, n-hexyl, isopropyl, isobutyl, isopentyl, amyl, sec-butyl, tert-butyl, tert-pentyl, n-heptyl, n-actyl, n-nonyl, n-decyl, undecyl, n-dodecyl, n-tetradecyl, pentadecyl, n-hexadecyl, heptadecyl, n-octadecyl, nonadecyl, eicosyl, dosyl, n-tetracosyl, and the like, along with branched variations thereof. In certain aspects of the disclosure an alkyl radical is a C$_1$-C$_6$ lower alkyl comprising or selected from the group consisting of methyl, ethyl, n-propyl, n-butyl, n-pentyl, n-hexyl, isopropyl, isobutyl, isopentyl, amyl, tributyl, sec-butyl, tert-butyl, tert-pentyl, and n-hexyl. An alkyl radical may be optionally substituted with substitutents as defined herein at positions that do not significantly interfere with the preparation of compounds of the disclosure and do not significantly reduce the efficacy of the compounds. In certain aspects of the disclosure, an alkyl radical is substituted with one to five substitutents including halo, lower alkoxy, lower aliphatic, a substituted lower aliphatic, hydroxy, cyano, nitro, thio, amino, keto, aldehyde, ester, amide, substituted amino, carboxyl, sulfonyl, sulfuryl, sulfenyl, sulfate, sulfoxide, substituted carboxyl, halogenated lower alkyl (e.g., CF$_3$), halogenated lower alkoxy, hydroxycarbonyl, lower alkoxycarbonyl, lower alkylcarbonyloxy, lower alkylcarbonylamino, cycloaliphatic, substituted cycloaliphatic, or aryl (e.g., phenylmethyl benzyl), heteroaryl (e.g., pyridyl), and heterocyclic (e.g., piperidinyl, morpholinyl). Substituents on an alkyl group may themselves be substituted.

The term "alkenyl" as used herein refers to an unsaturated, acyclic branched or straight-chain hydrocarbon radical comprising at least one double bond. An alkenyl radical may contain from about 2 to 24 or 2 to 10 carbon atoms, in particular from about 3 to 8 carbon atoms and more particularly about 3 to 6 or 2 to 6 carbon atoms. Suitable alkenyl radicals include without limitation ethenyl, propenyl (e.g., prop-1-en-1-yl, prop-1-en-2-yl, prop-2-en-1-yl (allyl), and prop-2-en-2-yl), buten-1-yl, but-1-en-2-yl, 2-methyl-prop-1-en-1-yl, but-2-en-1-yl, but-2-en-2-yl, buta-1,3-dien-1-yl, β-1,3-dien-2-3/1, hexen-1-yl, 3-hydroxyhexen-yl, hepten-1-yl, and octen-1-yl, and the like. An alkenyl radical may be optionally substituted similar to alkyl.

The term "alkylcarbamoyl" as used herein refers to a R'RN—CO— group wherein one of R and R' is hydrogen and the other of R and R' is alkyl and/or substituted alkyl as previously described.

The term "alkylene" as used herein refers to a linear or branched radical having from about 1 to 10, 1 to 8, 1 to 6, or 2 to 6 carbon atoms and having attachment points for two or more covalent bonds. Examples of such radicals are methylene, ethylene, propylene, butylene, pentylene, hexylene, ethylidene, methylethylene, and isopropylidene. When an alkenylene radical is present as a substituent on another radical it is typically considered to be a single substituent rather than a radical formed by two substituents.

The term "amino" as used herein, alone or in combination, refers to a radical where a nitrogen atom (N) is bonded to three substituents being any combination of hydrogen, hydroxyl, alkyl, cycloalkyl, alkenyl, alkynyl, aryl, silyl, heterocyclic, or heteroaryl which may or may not be substituted. Generally an "amino group" has the general chemical formula —NR'R" where R' and R" can be any combination of hydrogen, hydroxyl, alkyl, cycloalkyl, alkoxy, alkenyl, alkynyl, aryl, carbonyl carboxyl, amino, silyl, heteroaryl, or heterocyclic which may or may not be substituted. Optionally one substituent on the nitrogen atom may be a hydroxyl group (—OH) to provide an amine known as a hydroxylamine. Illustrative examples of amino groups are amino alkylamino, acylamino, cycloamino, acycloalkylamino, arylamino, arylalkylamino, and lower alkylsilylamino, in particular methylamino, ethylamino, dimethylamino, 2-propylamino, butylamino, isobutylamino, cyclopropylamino, benzylamino, allylamino, hydroxylamino, cyclohexylamino, piperidinyl, hydrazinyl, benzylamino, diphenylmethylamino, tritylamino, trimethylsilylamino, and dimethyl-tert-butylsilyiamino, which may or may not be substituted.

The term "amino" as used herein refers to the —NH$_2$ group.

The term "aralkoxycarbonyl" as used herein refers to an aralkyl-O—CO— group. An exemplary aralkoxycarbonyl group is benzyloxycarbonyl.

The term "aralkyl" as used herein refers to an aryl or a substituted aryl group bonded directly through an alkyl group, such as benzyl. Other particular examples of substituted aryl radicals include chlorobenzyl, and amino benzyl.

The term "aralkyl" as used herein refers to an aryl-alkyl- group wherein aryl and alkyl are as previously described, and included substituted aryl and substituted alkyl. Exemplary aralkyl groups include benzyl, phenylethyl, and naphthylmethyl.

The term "aralkyloxyl" as used herein refers to an aralkyl-O— group wherein the aralkyl group is as previously described. An exemplary aralkyloxyl group is benzyloxyl.

The term "aroyl" as used herein refers to aryl radicals, as defined above, attached to a carbonyl radical as defined herein, including without limitation benzoyl and toluoyl. An aroyl radical may be optionally substituted with groups as disclosed herein.

The term "aroylamino" as used herein refers to an aroyl-NH— group wherein aroyl is as previously described.

The term "aryl" as used herein refers to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

The term "aryloxy" as used herein refers to aryl radicals, as defined above, attached to an oxygen atom. Exemplary aryloxy groups include naphthyloxy, quinolyloxy, isoquinolizinyloxy, and the like.

The term "aryloxycarbonyl" as used herein refers to an aryl-O—CO— group. Exemplary aryloxycarbonyl groups include phenoxy- and naphthoxy-carbonyl.

The term "aryloxyl" as used herein refers to an aryl-O— group wherein the aryl group is as previously described, including a substituted aryl.

The term "arylalkoxy" as used herein refers to an aryl group attached to an alkoxy group. Representative examples of arylalkoxy groups include, but are not limited to, 2-phenylethoxy, 3-naphth-2-ylpropoxy, and 5-phenylpentyloxy.

The term "carbocyclic" as used herein includes radicals derived from a saturated or unsaturated, substituted or unsubstituted 5 to 14 member organic nucleus whose ring forming atoms (other than hydrogen) are solely carbon. Examples of carbocyclic radicals are cycloalkyl, cycloalkenyl, aryl, in particular phenyl, naphthyl, norbornanyl, bicycloheptadienyl, toluoyl, xylenyl, indenyl, stilbenzyl, terphenylyl, diphenylethylenyl, phenylcyclohexyl, acenaphthylenyl, anthracenyl, biphenyl, bibenzylyl, and related bibenzylyl homologs, octahydronaphthyl, tetrahydronaphthyl, octahydroquinolinyl, dimethoxytetrahydronaphthyl and the like.

The term "carbamoyl" as used herein, alone or in combination, refers to amino, monoalkylamino, dialkylamino, monocycloalkylamino, alkyleycloalkylamino, and dicycloalkylaxaino radicals, attached to one of two unshared bonds in a carbonyl group.

The term "carbonyl" as used herein refers to a carbon radical having two of the four covalent bonds shared with an oxygen atom.

The term "carboxamide" as used herein refers to the group —CONH—.

The term "cyano" as used herein refers to a carbon radical having three of four covalent bonds shared by a nitrogen atom, in particular —CN. A cyano group may be substituted with substituents described herein.

The terms "cyclic" and "cycloalkyl" as used herein refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur, or substituted or unsubstituted nitrogen atoms, wherein the nitrogen substituent is hydrogen, alkyl, substituted alkyl, aryl, or substituted aryl, thus providing a heterocyclic group.

Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The term "cycloaliphatic" as used herein refers to a cycloalkane possessing less than 8 carbons or a fused ring system consisting of no more than three fused cycloaliphatic rings. Examples of such groups include, but are not limited to, decalin and the like.

The term "cycloalkenyl" as used herein refers to radicals comprising about 4 to 16, 2 to 15, 2 to 10, 2 to 8, 4 to 10, 3 to 8, 3 to 7, 3 to 6, or 4 to 6 carbon atoms, one or more carbon-carbon double bonds, and one, two, three, or four rings wherein such rings may be attached in a pendant manner or may be fused. In certain aspects of the disclosure the cycloalkenyl radicals are "lower cycloalkenyl" radicals having three to seven carbon atoms. Examples of cycloalkenyl radicals include without limitation cyclobutenyl, cyclopentenyl, cyclohexenyl and cycloheptenyl. A cycloalkenyl radical may be optionally substituted with groups as disclosed herein, in particular 1, 2, or 3 substituents which may be the same or different.

The term "cycloalkoxy" as used herein refers to cycloalkyl radicals (in particular, cycloalkyl radicals having 3 to 15, 3 to 8 or 3 to 6 carbon atoms) attached to an oxy radical. Examples of cycloalkoxy radicals include cyclohexoxy and cyclopentoxy. A cycloalkoxy radical may be optionally substituted with groups as disclosed herein.

The term "cycloalkyl" as used herein refers to radicals having from about 3 to 15, 3 to 10, 3 to 8, or 3 to 6 carbon atoms and containing one, two, three, or four rings wherein such rings may be attached in a pendant manner or may be fused. In aspects of the disclosure, "cycloalkyl" refers to an optionally substituted, saturated hydrocarbon ring system containing 1 to 2 rings and 3 to 7 carbons per ring which may be further fused with an unsaturated C3-C7 carbocylic ring. Examples of cycloalkyl groups include single ring structures such as cyclopropyl, cyclobutyl, cyclopentyl, cyclohexyl, cycloheptyl, cyclooctyl, cyclononyl, cyclodecyl, cyclododecyl, and the like, or multiple ring structures such as adamantanyl, and the like. In certain aspects of the disclosure the cycloalkyl radicals are "lower cycloalkyl" radicals having from about 3 to 10, 3 to 8, 3 to 6, or 3 to 4 carbon atoms, in particular cyclopropyl, cyclobutyl, cyclopentyl, cyclohexyl and cycloheptyl. The term "cycloalkyl" also embraces radicals where cycloalkyl radicals are fused with aryl radicals or heterocyclyl radicals. A cycloalkyl radical may be optionally substituted with groups as disclosed herein.

The term "dialkylamino" as used herein refers to an —NRR' group wherein each of R and R' is independently an alkyl group and/or a substituted alkyl group as previously described. Exemplary alkylamino groups include ethylmethylamino, dimethylamino, and diethylamino.

The term "dialkylcarbamoyl" as used herein refers to a R'RN—CO— group wherein each of R and R' is independently alkyl and/or substituted alkyl as previously described.

The terms "halo," "halide," or "halogen" as used herein refer to fluoro, chloro, bromo, and iodo groups.

The term "heteroaryl" as used herein refers to fully unsaturated heteroatom-containing ring-shaped aromatic radicals having at least one heteroatom selected from carbon, nitrogen, sulfur and oxygen. A heteroaryl radical may contain one, two or three rings and the rings may be attached in a pendant manner or may be fused. In aspects of the disclosure the term refers to fully unsaturated heteroatom-containing ring-shaped aromatic radicals having from 3 to 15, 3 to 10, 3 to 8, 5 to 15, 5 to 10, or 5 to 8 ring members selected from carbon, nitrogen, sulfur and oxygen, wherein at least one ring atom is a heteroatom. Examples of "heteroaryl" radicals, include without limitation, an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, tetrazolyl and the like; an unsaturated condensed heterocyclic group containing 1 to 5 nitrogen atoms, in particular, indolyl, isoindolyl, indolizinyl, benzimidazolyl, quinolyl, isoquinolyl, indazolyl, quinazolinyl, pteridinyl, quinolizidinyl, phthalazinyl, naphthyridinyl, quinoxalinyl, cinnolinyl, phenanthridinyl, acridinyl, phenanthrolinyl, phenazinyl, carbazolyl; purinyl, benzimidazolyl, quinolinyl, isoquinolinyl, benzotriazolyl, tetrazolopyridazinyl and the like; an unsaturated 3 to 6-membered heteromonocyclic group containing an oxygen atom, in particular, 2-furyl, pyranyl, and the like; an unsaturated 5 to 6-membered heteromonocyclic group containing a sulfur atom, in particular, thienyl, 2-thienyl, 3-thienyl, and the like; unsaturated 5 to 6-membered heteromonocyclic group containing 1 to 2 oxygen atoms and 1 to 3 nitrogen atoms, in particular, furazanyl, benzofurazanyl, oxazolyl, isoxazolyl, and oxadiazolyl; an unsaturated condensed heterocyclic group containing 1 to 2 oxygen atoms and 1 to 3 nitrogen atoms, in particular benzoxazolyl, benzoxadiazolyl and the like; an unsaturated 5 to 6-membered heteromonocyclic group containing 1 to 2 sulfur atoms and 1 to 3 nitrogen atoms, for example, thiazolyl, isothiazolyl, thiadiazolyl and the like; an unsaturated condensed heterocyclic group containing 1 to 2 sulfur atoms and 1 to 3 nitrogen atoms such as benzothiazolyl, benzothiadiazolyl and the like. The term also includes radicals where heterocyclic radicals are fused with aryl radicals, in particular bicyclic radicals such as benzofuranyl, benzothiophenyl, phthalazinyl, chromenyl, xanthenyl, and the like. A heteroaryl radical may be optionally substituted with groups as disclosed herein, for example with an alkyl, amino, halogen, etc., in particular a heteroarylamine. The term may refer to an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, pyridinyl, pyrimidinyl, pyrazinyl, pyridazinyl, triazolyl, tetrazolyl and the like. A heteroaryl radical may be optionally substituted with groups disclosed herein, for example with an alkyl, amino, halogen, etc., in particular a substituted heteroaryl radical is a heteroarylamine.

The term "heterocyclic" as used herein refers to a cycloalkane and/or an aryl ring system, possessing less than 8 carbons, or a fused ring system consisting of no more than three fused rings, where at least one of the ring carbon atoms is replaced by oxygen, nitrogen or sulfur. Examples of such groups include, but are not limited to, morpholino and the like.

The term "hydroxyalkyl" as used herein refers to an alkyl group substituted with an —OH group.

The term "hydroxyl" as used herein refers to the —OH group.

The term "lower-alkyl-substituted-amino" as used herein refers to any alkyl unit containing up to and including eight carbon atoms where one of the aliphatic hydrogen atoms is replaced by an amino group. Examples of such include, but are not limited to, ethylamino and the like.

The term "lower-alkyl-substituted-halogen" as used herein refers to any alkyl chain containing up to and including eight carbon atoms where one of the aliphatic hydrogen atoms is replaced by a halogen. Examples of such include, but are not limited to, chloroethyl and the like.

The term "nitro" as used herein means —NO$_2$.

The term "oxo" as used herein refers to a compound described previously herein wherein a carbon atom is replaced by an oxygen atom.

The term "substituted alkenyl" as used herein includes an alkenyl group substituted by, for example, one to three substituents, preferably one to two substituents, such as alkyl, alkoxy, haloalkoxy, alkylalkoxy, haloalkoxyalkyl, alkanoyl, alkanoyloxy, cycloalkyl, cycloalkoxy, acyl, acylamino, acyloxy, amino, alkylamino, alkanoylamino, aminoacyl, aminoacyloxy, cyano, halogen, hydroxyl, carboxyl, carboxylalkyl, carbamyl, keto, thioketo, thiol, alkylthio, sulfonyl, sulfonamido, thioalkoxy, aryl, nitro, and the like.

In aspects of the disclosure, "substituted alkyl" includes an alkyl group substituted by, for example, one to five substituents, and preferably 1 to 3 substituents, such as alkyl, alkoxy, oxo, alkanoyl, aryl, aralkyl, aryloxy, alkanoyloxy, cycloalkyl, acyl, amino, hydroxyamino, alkylamino, arylamino, alkoxyamino, aralkylamino, cyano, halogen, hydroxyl, carboxyl, carbamyl, carboxylalkyl, keto, thioketo, thiol, alkylthiol, arylthio, aralkylthio, sulfonamide, thioalkoxy, and nitro.

The term "substituted aryl" as used herein includes an aromatic ring, or fused aromatic ring system consisting of no more than three fused rings at least one of which is aromatic, and where at least one of the hydrogen atoms on a ring carbon has been replaced by a halogen, an amino, a hydroxy, a nitro, a thio, an alkyl, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, hydroxyphenyl, chlorophenyl and the like.

The term "substituted cycloaliphatic" as used herein refers to a cycloalkane possessing less than 8 carbons or a fused ring system consisting of no more than three fused rings, and where at least one of the aliphatic hydrogen atoms has been replaced by a halogen, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted cycloaliphatic). Examples of such groups include, but are not limited to, 1-chlorodecalyl and the like.

The term "substituted cycloalkyl" as used herein includes cycloalkyl groups having from 1 to 5 (in particular 1 to 3) substituents including without limitation alkyl, alkenyl, alkoxy, cycloalkyl, substituted cycloalkyl, acyl, acylamino, acyloxy, amino, aminoacyl, aminoacyloxy, oxyacylamino, cyano, halogen, hydroxyl, carboxyl, carboxylalkyl, keto, thioketo, thiol, thioalkoxy, aryl, aryloxy, heteroaryl, heteroaryloxy, hydroxyamino, alkoxyamino, and nitro.

The term "substituted heterocyclic" as used herein refers to a cycloalkane and/or an aryl ring system, possessing less than 8 carbons, or a fused ring system consisting of no more than three fused rings, where at least one of the ring carbon atoms is replaced by oxygen, nitrogen or sulfur, and where at least one of the aliphatic hydrogen atoms has been replaced by a halogen, hydroxy, a thio, nitro, an amino, a ketone, an aldehyde, an ester, an amide; a lower aliphatic, a substituted lower aliphatic, or a ring (aryl, substituted aryl, cycloaliphatic, or substituted cycloaliphatic). Examples of such groups include, but are not limited to 2-chloropyranyl.

The term "substituted aliphatic" as used herein refers to an alkyl or an alkane possessing less than 10 carbons. The term "substituted aliphatic" refers to an alkyl or an alkane possessing less than 10 carbons where at least one of the aliphatic hydrogen atoms has been replaced by a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.). Examples of such groups include, but are not limited to, 1-chloroethyl and the like.

Compounds of the disclosure can be prepared using reactions and methods generally known to the person of ordinary skill in the art, having regard to that knowledge and the disclosure of this application including the Examples. The reactions are performed in solvent appropriate to the reagents and materials used and suitable for the reactions being effected. It will be understood by those skilled in the art of organic synthesis that the functionality present on the compounds should be consistent with the proposed reaction steps. This will sometimes require modification of the order of the synthetic steps or selection of one particular process scheme over another in order to obtain a desired compound of the disclosure. It will also be recognized that another major consideration in the development of a synthetic route is the selection of the protecting group used for protection of the reactive functional groups present in the compounds described in this disclosure. An authoritative account describing the many alternatives to the skilled artisan is Greene and Wuts (Protective Groups In Organic Synthesis, Wiley and Sons, 1991).

Compounds of the disclosure which are acidic in nature are capable of forming base salts with various pharmacologically acceptable cations. These salts may be prepared by conventional techniques by treating the corresponding acidic compounds with an aqueous solution containing the desired pharmacologically acceptable cations and then evaporating the resulting solution to dryness, preferably under reduced pressure. Alternatively, they may be prepared by mixing lower alkanolic solutions of the acidic compounds and the desired alkali metal alkoxide together and then evaporating the resulting solution to dryness in the same manner as before. In either case, stoichiometric quantities of reagents are typically employed to ensure completeness of reaction and maximum product yields.

The compounds of the disclosure which are basic in nature can form a wide variety of different salts with various inorganic and organic acids. In practice is it desirable to first isolate a compound of the disclosure from a reaction mixture as a pharmaceutically unacceptable salt and then convert the latter to the free base compound by treatment with an alkaline reagent and subsequently convert the free base to a pharmaceutically acceptable acid addition salt. The acid addition salts of the base compounds of the disclosure are readily prepared by treating the base compound with a substantially equivalent amount of the chosen mineral or inorganic or organic acid in an aqueous solvent medium or in a suitable organic solvent such as methanol or ethanol. Upon careful evaporation of the solvent, the desired solid salt is obtained.

Discussion

The present disclosure encompasses embodiments of methods for the meta-selective C—H arylations of arene alcohol-based substrates. The strategy involves the combination of a transient norbornene strategy with a quinoline-based acetal scaffold to achieve the formation of biaryl compounds. Both a two-step meta-arylation/scaffold cleavage process and a total telescoping procedure are provided, highlighting the advantageous attribute of attachment, removal, and recovery of the acetal scaffold. Moreover, the meta-arylated compounds can be further derivatized via ortho-selective functionalizations. These processes establish a process for the catalytic polyfunctionalization of alcohol-based compounds. The norbornene strategy juxtaposed with a scaffolding protocol is used to achieve meta-selective functionalizations of alcohol-based substrates, which represents a novel approach to meta-selective arylation of arene alcohol-based substrates.

Figure 2:
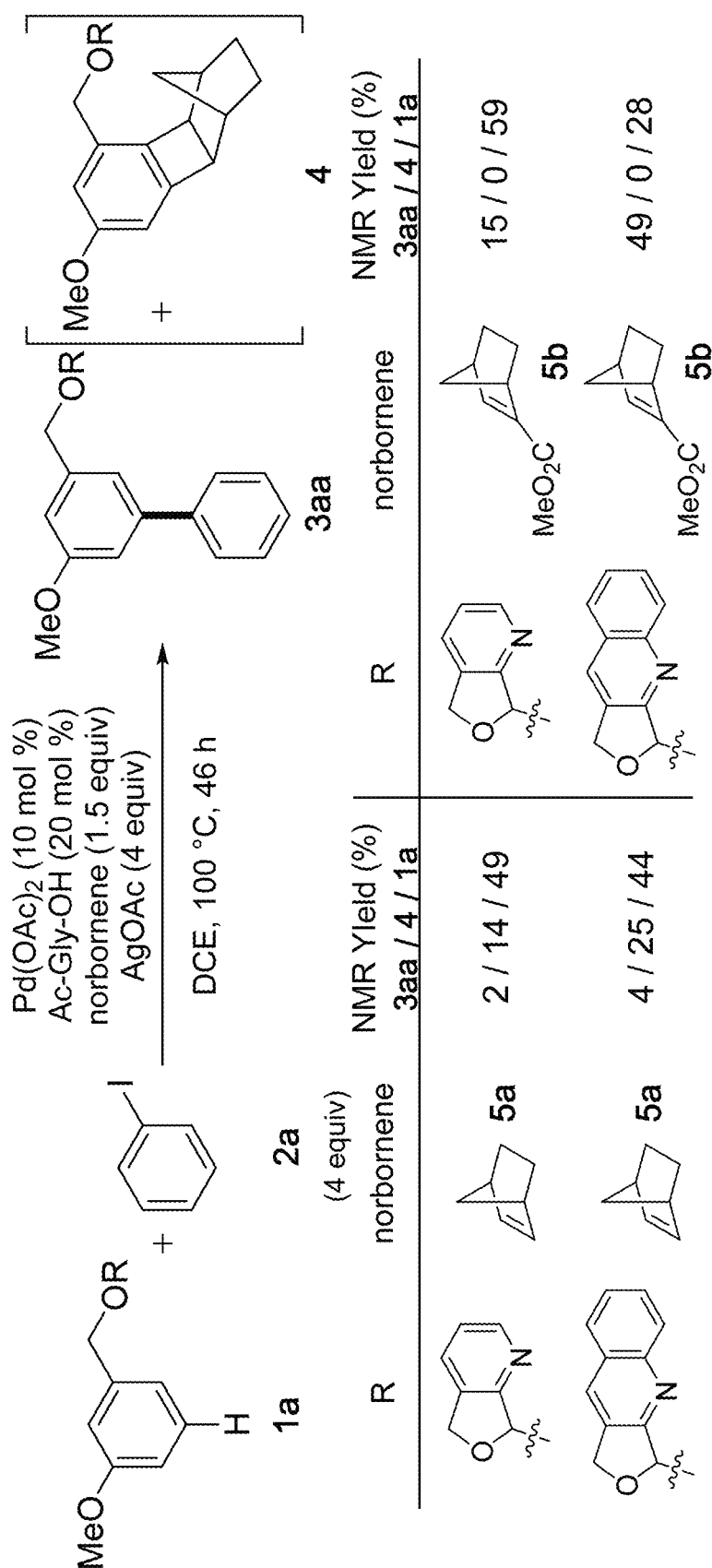
FIG. 2 illustrates Scheme 1 for the preliminary evaluation of meta-selective arylations using an alcohol scaffold.

The reaction of 3-methoxybenzyl alcohol (1a) was evaluated with respective to attached heterocyclic scaffolds (FIG. 2). The pyridyl acetal substrate was synthesized from PyAOH in the presence of TsOH.H$_2$O and MgSO$_4$. For the quinolinyl acetal substrates, it was found that the QuAOBz strategy (TFA, then K$_2$CO$_3$) was generally effective for attachment.

When these substrates were treated under oxidative arylation conditions using norbornene as the transient mediator, minimal meta-arylation products (3aa) were observed. Additionally, significant amounts of recovered starting material and observable quantities of a benzocyclobutane byproduct (4) were observed albeit with low reactivity (FIG. 2). It was found, however, that norbornene 5b (NBE-CO$_2$Me), developed by Yu for this transient strategy (Shen et al., (2015) *J. Am. Chem. Soc.* 137: 11574-11577; Wang et al., (2016) *J. Am. Chem. Soc.* 138: 9269-9276; Wang et al., (2016) *J. Am. Chem. Soc.* 138: 14092-14099; Shi et al., (2016) *J. Am. Chem. Soc.* 138: 14876-14879; Wang et al., (2017) *Angew. Chem. Int. Ed.* 56: 5125-5129; Wang et al., (2017) *Angew. Chem.* 2017, 129, 5207-5211; Li et al., (2017) *Angew. Chem. Int. Ed.* 56: 6874-6877; Li et al., (2017) *Angew. Chem.* 2017, 129, 6978-6981; Chen et al., (2017) *Angew. Chem. Int. Ed.* 56: 8183-8186; Chen et al., (2017) *Angew. Chem.* 2017, 129, 8295-8298) improved the arylation, with no observation of benzocyclobutane byproduct. The quinolinyl-based scaffold also afforded a significant enhancement in reactivity (49% versus 15% yield as shown in FIG. 2).

Other parameters of the transformation were also evaluated as shown in Table 1. Catalyst Pd(TFA)$_2$ bolstered reactivity, affording the product in 65% yield (Table 1, entry 1). Four equivalents each of phenyl iodide and silver acetate (AgOAc) were advantageous and different silver salts were minimally effective, as shown in Table 1, entries 3-6.

Investigations into ligands showed that 2-hydroxypyridine ligands, often effective for similar meta-C—H functionalization processes (Wang et al., (2016) *J. Am. Chem. Soc.* 138: 9269-9276; Wang et al., (2016) *J. Am. Chem. Soc.* 138: 14092-14099; Shi et al., (2016) *J. Am. Chem. Soc.* 138: 14876-14879; Wang et al., (2017) *Angew. Chem. Int. Ed.* 56: 5125-5129; Wang et al., (2017) *Angew. Chem.* 129: 5207-5211; Li et al., (2017) *Angew. Chem. Int. Ed.* 56: 6874-6877; Li et al., (2017) *Angew. Chem.* 129: 6978-6981; Chen et al., (2017) *Angew. Chem. Int. Ed.* 56: 8183-8186; Chen et al., (2017) *Angew. Chem.* 129: 8295-8298) did not improve reactivity (Table 1, entries 7-8).

In evaluating amino acid derivatives, both N-trifluoroacetylglycine (TFA-Gly-OH) and N-trifluoroacetyl-β-alanine (TFA-β-Ala-OH) were similarly advantageous, affording the arylated product (3aa) in much improved yield (78%, with 8% rsm, Table 1, entries 17, 18). Considering the availability of the amino acids, TFA-Gly-OH was selected for further studies. The reaction could be performed without ligand in decreased but still measurable yield; AgOAc, however, was required (entries 21, 22). Procedurally, the reaction was generally concluded by adding approximately 0.1 mL ethylenediamine and stirring for 2 h to remove any palladium complexes and facilitate purification, as described in Example 15, below.

TABLE 1

Optimization of the meta-C-H arylation of the QuA-attached scaffold

| Entry | Ligand | Additive | Time (h) | Yield [%][a] | Rsm [%][a,b] |
|---|---|---|---|---|---|
| 1 | Ac-Gly-OH | AgOAc | 46 | 65 | 17 |
| 2[c] | Ac-Gly-OH | AgOAc | 72 | 59 | 21 |
| 3 | Ac-Gly-OH | Ag$_2$CO$_3$ | 46 | 26 | 65 |
| 4 | Ac-Gly-OH | AgOPiv | 46 | 12 | 82 |
| 5 | Ac-Gly-OH | AgOTf | 46 | nd | nd |
| 6 | Ac-Gly-OH | AgTFA | 22.5 | nd | nd |
| 7 | (pyridine-NHAc, OH) | AgOAc | 24 | 33 | 52 |
| 8 | (fluorinated benzamide, pyridine-OH) | AgOAc | 24 | 23 | 69 |
| 9 | Ac-Ala-OH | AgOAc | 46 | 57 | 20 |
| 10 | Ac-t-Leu-OH | AgOAc | 46 | 64 | 12 |
| 11 | Ac-Phe-OH | AgOAc | 46 | 53 | 24 |
| 12 | Ac-β-Ala-OH | AgOAc | 46 | 66 | 8 |
| 13 | Boc-Gly-OH | AgOAc | 46 | 69 | 8 |
| 14 | Formyl-Gly-OH | AgOAc | 46 | 49 | 35 |
| 15 | Bz-Gly-OH | AgOAc | 46 | 23 | 61 |
| 16 | TFA-Gly-OH | AgOAc | 46 | 75 | 7 |
| 17 | TFA-β-Ala-OH | AgOAc | 24 | 78 | 8 |
| 18 | TFA-Gly-OH | AgOAc | 24 | 78 | 8 |
| 19 | TFA-Gly-OH | AgOAc | 15 | 74 | 13 |
| 20 | none | AgOAc | 24 | 60 | 9 |
| 21 | TFA-Gly-OH | KOAc | 24 | 4 | 95 |
| 22 | TFA-Gly-OH | none | 24 | 0 | 66 |

[a]NMR yield using 1-octene as a standard. nd: Not detected.
[b]Rsm: recovered starting material.
[c]3 equiv. each 2a, AgOAc.

Figure 3:
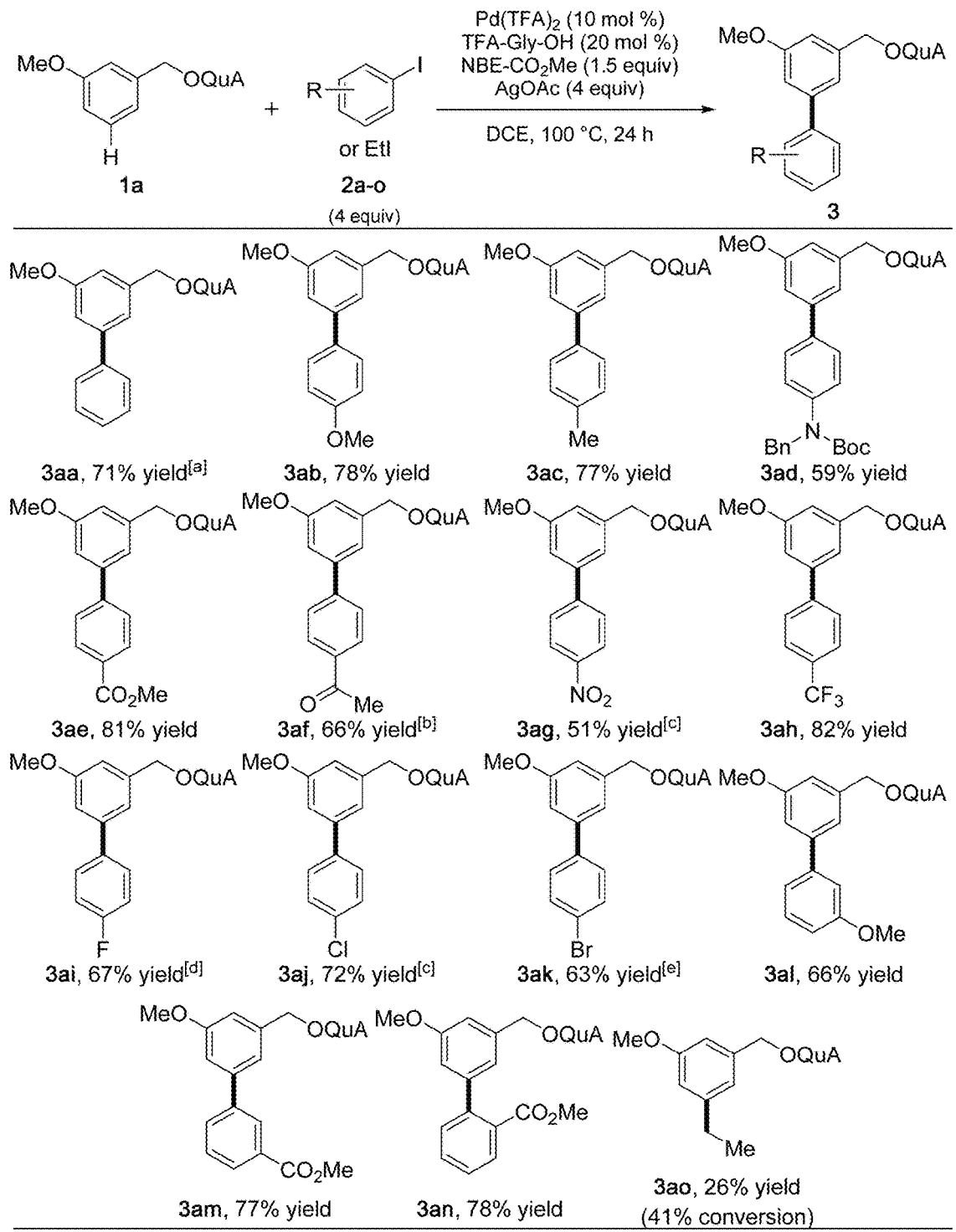
FIG. 3 illustrates Scheme 2 showing the iodide scope in meta-selective arylations.

The substrate scope was investigated as shown by Scheme 2 in FIG. 3. The aryl iodide component was evaluated, and it was found that a variety of substituted aromatic groups could be employed. Both electron rich and electron poor aryl iodides were reactive, and the transformation showed good functional group compatibility (e.g., ether, ester, ketone, carbamate, nitro, trifluoromethyl, and halogen). Aryl iodides bearing a para-, meta-, or ortho-substituent afforded the corresponding products in good to excellent yields. An alkyl iodide could also be utilized, although the alkylated arene was obtained in only modest yield (as shown in Example 29, compound 3ao).

Figure 4:
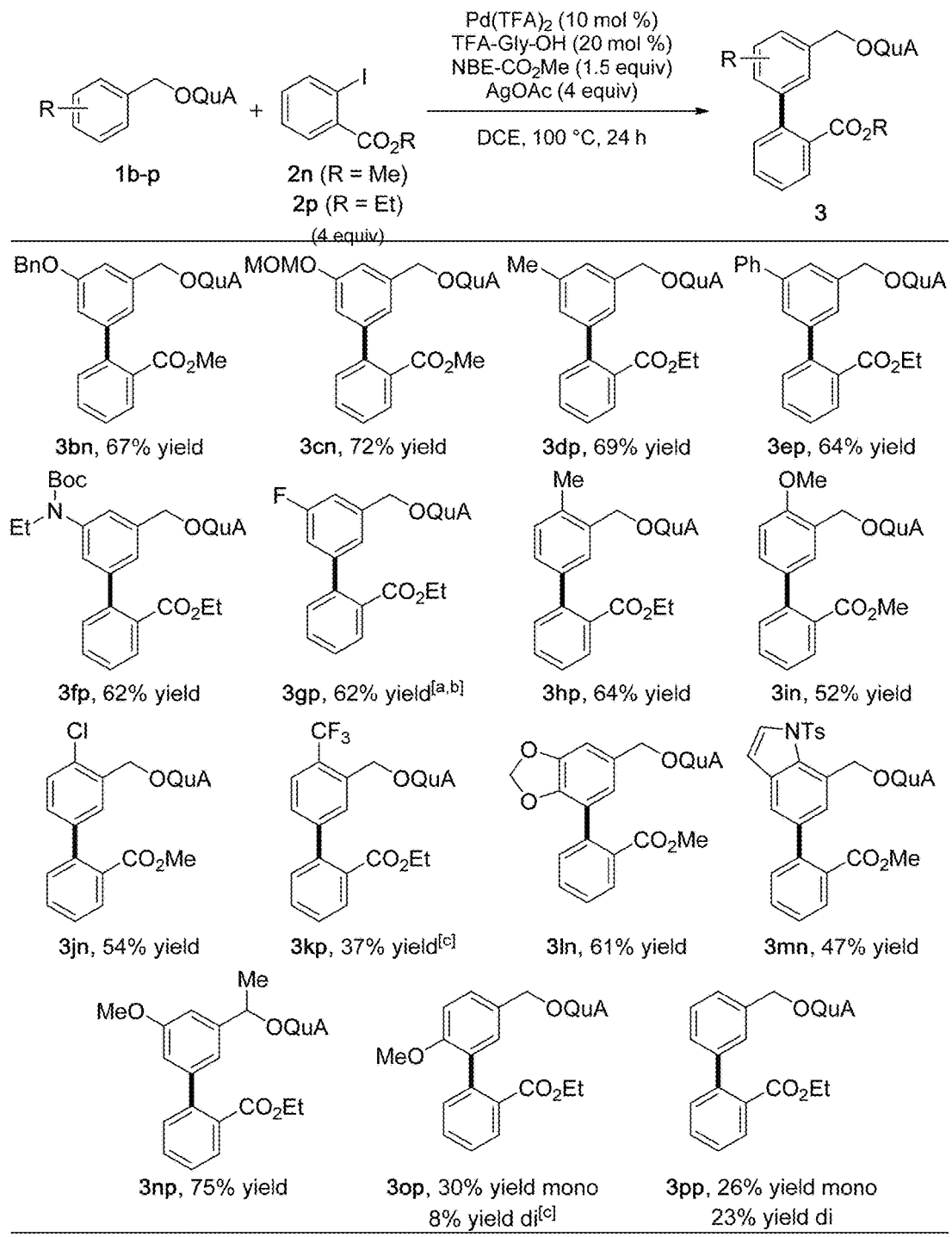
FIG. 4 illustrates Scheme 3 showing arene alcohol substrate scope in meta-selective arylations.

A range of scaffold-attached benzylic alcohol substrates were also evaluated (Scheme 3, FIG. 4), using unsubstituted or substituted iodobenzoate as the coupling agent. While the selection of methyl benzoate was made for ease of chromatographic purification, it was recognized that other alkylbenzoates including, but not limited to, ethyl benzoate may be usefully employed in the methods of the disclosure.

The transformation worked better for aryl compounds bearing electron-rich substituents, such as ethers, alkyls, arenes, and carbamates. Electron-withdrawing groups (e.g., halides in 3gp, 3jn) were still tolerated, however. The procedure has been found to work most effectively with meta-substituted benzylic alcohol-based substrates; ortho-substituted cases were also competent but in diminished yields, as shown in Examples 36-39 and 41 (compounds 3hp, 3in, 3jn, 3kp, 3mn). The 3,4-methylenedioxy group was effective (31n, 61% yield, Example 40), as was a heterocyclic compound (3mn, 47% yield, Example 41). The meta-arylation could be extended to secondary alcohol-based compounds (3np, 75% yield, Example 42). Finally, for cases where mono- and di-arylation were possible, both products were observed. Diarylation is only possible when the arene alcohol is unsubstituted at both ortho and both meta positions. If either an ortho or a meta position is substituted, or both are substituted, then only mono-arylation will occur. Substrates based on homobenzylic and bishomobenzylic alcohols, which were reactive in ortho-selective functionalizations, did not produce the desired meta-arylated species when evaluated.

Figure 5:
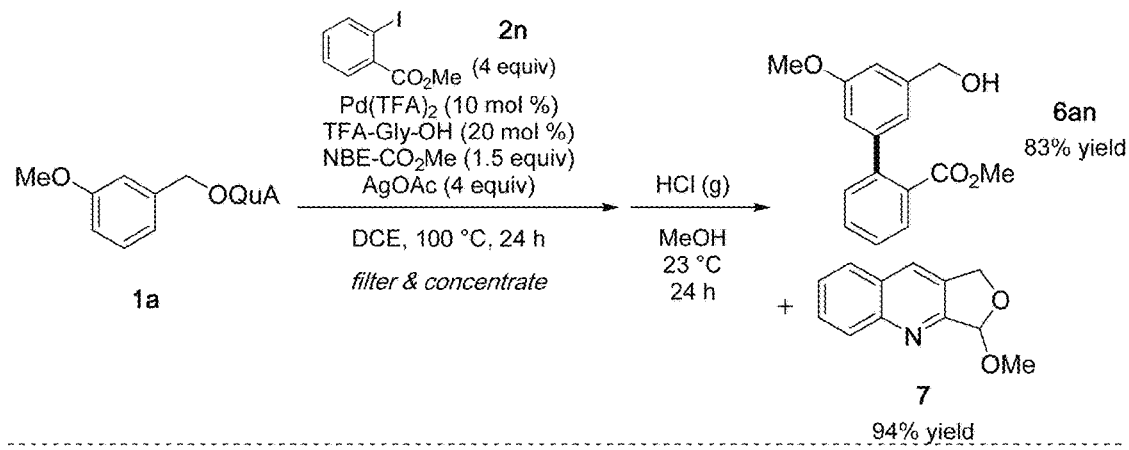
FIG. 5 illustrates Scheme 4 showing scaffold cleavage and a telescoping protocol.
Figure 5:
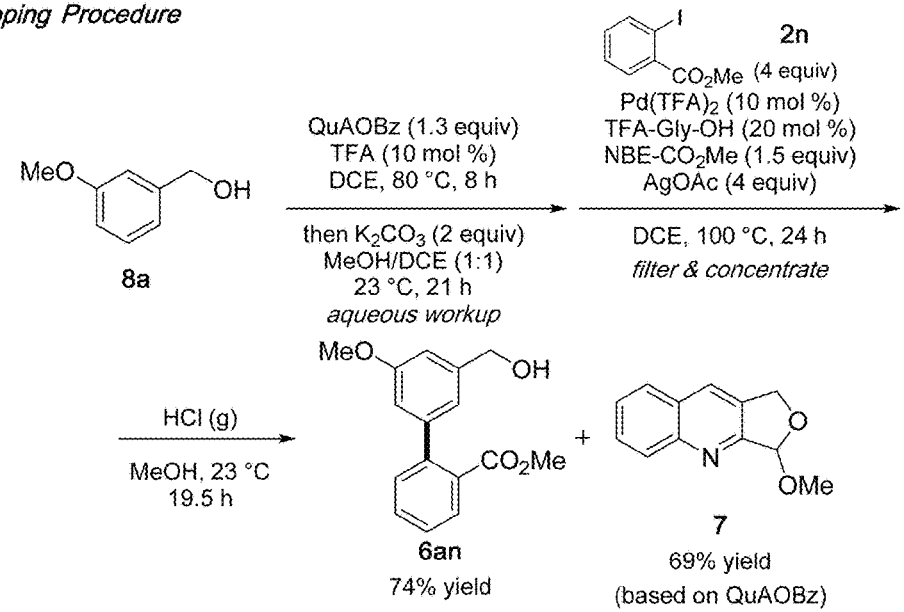

An advantage of the scaffolding approach of the disclosure is the lability of the acetal for direct scaffold cleavage and recovery. Scheme 4 as shown in FIG. 5 is illustrative in the context of this meta-arylation. A sequential procedure of arylation with immediate subsequent scaffold cleavage afforded biaryl alcohol 6an in 83% yield. The slightly lower yield of compound 3an in Scheme 2 (FIG. 3) relative to compound 6an likely reflects the small amount of acetal cleavage over the course of the arylation and purification. Methyl acetal-derived scaffold (QuAOMe, 7) was also recovered in 94% yield; this compound can be reused in further attachment sequences (Li et al., (2016) *Chem. Eur. J.* 22: 13054-13058). Furthermore, a telescoping procedure for this meta-arylation process using the quinolinyl scaffold could also be executed. Benzylic alcohol 8a was converted to the meta-arylated alcohol (6an) in 74% yield without any intermediate purifications (Example 45).

Figure 6:
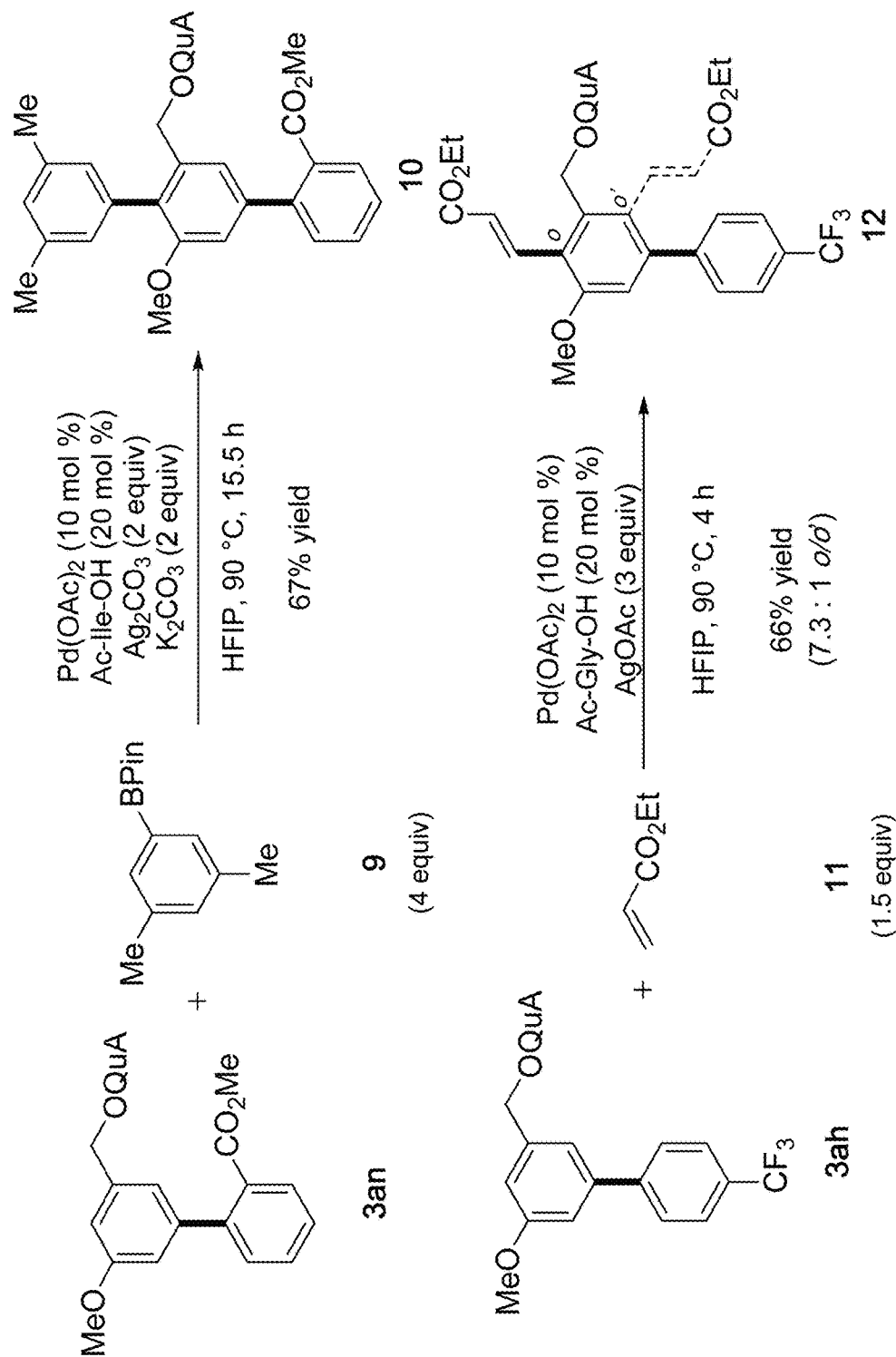
FIG. 6 illustrates Scheme 5 showing polyfunctionalization via the scaffolding strategy.

The scaffolding approach of the methods of the disclosure for the meta-arylation complements existing ortho-functionalization strategies. To that end, it has been demonstrated that the meta-arylated products can undergo subsequent functionalizations (Scheme 5, FIG. 6). The ortho-C—H arylation of compound 3an can afford the secondary arylated product (10) in 67% yield. Olefination was also successful; the C—H alkenylation of compound 3ah affords alkene product 12 in 66% yield (Example 22). Accordingly, the scaffold and methods of the disclosure can be utilized for the facile diversified syntheses of polysubstituted arene alcohols via select functionalization strategies.

Accordingly, the disclosure provides embodiments of a method for site selective meta-C—H arylation of benzylic alcohols via palladium catalysis by incorporating the norbornene transient mediator strategy into a quinoline-based acetal scaffold. The particular use of amino acid-based ligands for this reaction is distinct in the norbornene strategy, and suggests cooperation of ligand and scaffold in this functionalization process. The transformation shows considerable scope and functional group compatibility, and the desired biaryl compounds can be obtained in generally moderate to high yields. Scaffold cleavage and recovery, in addition to a telescoping protocol, was achieved in good yields without purification of any intermediates. The meta-arylation can also be combined with ortho-arylation or olefinations to afford polysubstituted arenes, establishing a foundational platform for ready diversifications of aromatic systems. Considering the synthetic versatility of the alcohol functional group, this scaffolding strategy toward functionalization can enable the facile and direct syntheses of an array of arene compounds.

One aspect of the disclosure, therefore, encompasses embodiments of a method of meta-arylating an arene alcohol, the method comprising the steps of: (a) attaching a heterocyclic hemiacetal scaffold to an aromatic alcohol or a substituted aromatic alcohol; (b) reacting the aromatic or substituted aromatic alcohol having the heterocyclic hemiacetal scaffold attached thereto with an alkyl or aryl iodide in a reaction mix comprising a palladium catalyst, a silver salt, and carboxymethyl norbornene to generate a meta-arylated arene conjugated to the heterocyclic hemiacetal scaffold; and (c) cleaving the heterocyclic hemiacetal scaffold from the meta-arylated arene alcohol.

In some embodiments of this aspect of the disclosure, in step (b) of the method, the reaction mix can further comprise a ligand.

In some embodiments of this aspect of the disclosure, the heterocyclic hemiacetal scaffold can be quinolinyl hemiacetal benzoate.

In some embodiments of this aspect of the disclosure, the aryl iodide can have the formula I:

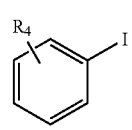

wherein $R_4$ can be selected from the group consisting of: H, a halogen, an alkyl, an alkoxy, a carboxyalkyl, an alkylbenzoate, a substituted amine, an ether, a ketone, an ester, a carbamate, a nitro, and a halogenated alkyl.

In some embodiments of this aspect of the disclosure, the aryl iodide can be an iodoalkylbenzoate.

In some embodiments of this aspect of the disclosure, the iodoalkylbenzoate can be iodomethylbenzoate.

In some embodiments of this aspect of the disclosure, the ligand can be selected from the group consisting of acetylglycine, 3-acetylamino 2-hydroxypyridine, 3-[3-trifluoro 1-amido tetrafluorophenyl] 2-hydroxy pyridine, acetylalanine, acetyl tert-alanine, acetylphenylalanine, acetyl β-alanine, Boc-glycine, formyl-glycine, benzoylglycine, trifluoroacetylglycine, and trifluoroacetyl-β-alanine.

In some embodiments of this aspect of the disclosure, ligand can be trifluoroacetylglycine or trifluoroacetyl-β-alanine.

In some embodiments of this aspect of the disclosure, ligand can be trifluoroacetylglycine.

In some embodiments of this aspect of the disclosure, the palladium catalyst can be palladium acetate or palladium trifluoroacetate.

In some embodiments of this aspect of the disclosure, the palladium catalyst is palladium trifluoroacetate.

In embodiments of this aspect of the disclosure, the silver salt can be silver acetate.

In some embodiments of this aspect of the disclosure, the cleavage of the heterocyclic hemiacetal scaffold from the meta-arylated arene alcohol generates an alkylayted heterocyclic hemiacetal scaffold and the steps (a)-(c) are repeated using the alkylayted heterocyclic hemiacetal scaffold in step (a).

Another aspect of the disclosure encompasses embodiments of a method of meta-arylating an arene alcohol, the method comprising the steps of: (a) attaching a quinolinyl hemiacetal benzoate to an aromatic alcohol or a substituted aromatic alcohol wherein the aromatic alcohol or a substituted aromatic alcohol has the formula II:

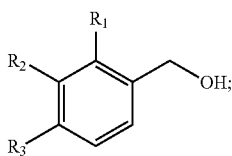

thereby forming form a compound of formula III:

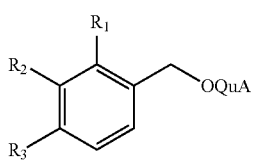

(b) reacting the compound of formula IV with an alkyl or aryl iodide having the formula I:

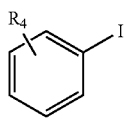

in the presence of a palladium trifluoroacetate catalyst, silver acetate, trifluoroacetylglycine, and carboxymethyl norbornene to generate a meta-arylated arene-quinolinyl hemiacetal scaffold conjugate; and (c) incubating the meta-arylated arene-quinolinyl hemiacetal scaffold conjugate of step (b) with an alkyl alcohol under acid conditions to generate an alkylayted quinolinyl hemiacetal scaffold having the formula VI:

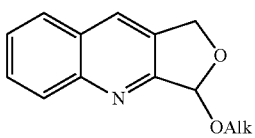

and a meta-arylated arene alcohol having the formula VII.

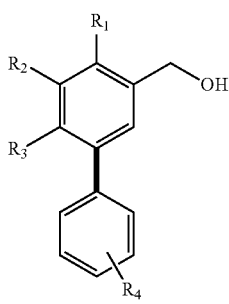

wherein: $R_1$, $R_2$, or $R_3$ can be independently selected from the group consisting of: H, a halogen, an alkyl, a substituted alkyl, an aryl, a substituted aryl, an amino group, a substituted amino group, an alkoxy group, a heterocyclic group, $R_1$ and $R_2$ can be linked to form a cyclic group, and $R_2$ and $R_3$ can be linked to form a cyclic group; and $R_4$ can be selected from the group consisting of: H, a halogen, an alkyl, an alkoxy, a carboxyalkyl, an alkylbenzoate, a substituted amine, an ether, a ketone, an ester, a carbamate, a nitro, and a halogenated alkyl.

In some embodiments of this aspect of the disclosure, the aryl iodide can be an iodoalkylbenzoate.

In some embodiments of this aspect of the disclosure, the iodoalkylbenzoate can be iodomethylbenzoate.

In some embodiments of this aspect of the disclosure, the steps (a)-(c) are repeated wherein the alkylayted quinolinyl hemiacetal scaffold replaces the quinolinyl hemiacetal benzoate scaffold in step (a).

In some embodiments of this aspect of the disclosure, when in the aromatic alcohol having the formula II $R_1$ and $R_2$ are both H, the meta-arylated arene alcohol product of step (b) having the formula VI can be a mono-meta-arylated aromatic alcohol, a di-meta-arylated aromatic alcohol, or a mixture thereof.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLES

Example 1

Materials and Methods:

Tetrahydrofuran, dichloromethane, diethyl ether, DMF, and toluene were purified by passing through activated alumina columns. Anhydrous HCl gas was regularly prepared by adding concentrated HCl to anhydrous $CaCl_2$. NBE-$CO_2$Me was synthesized according to the procedure of Yu et al. ((2015) *J. Am. Chem. Soc.* 137: 11574-11577). All other reagents were used as received unless otherwise noted. Qualitative TLC and preparatory plate chromatography was performed on 250 mm thick, 60 Å, glass backed, F254 silica (Silicycle, Quebec City, Canada). Visualization was accomplished with UV light and exposure to $KMnO_4$ or Dragendorff stain solutions followed by heating. Flash column chromatography was performed using Silicylce silica gel (230-400 mesh). $^1$H NMR spectra were acquired on a Varian Mercury Plus (at 400 MHz) or a Varian Unity Inoval (at 500 MHz) and are reported relative to $SiMe_4$ (δ 0.00). $^{13}$C NMR spectra were acquired on a Varian Mercury Plus (at 100 MHz) or a Varian Unity (nova at 125 MHz) and are reported relative to $SiMe_4$ (δ 0.0). $^{19}$F NMR spectra were acquired on a Varian Mercury Plus (at 376 MHz) and are reported relative to $CFCl_3$ (δ 0.0). All IR spectra were obtained as a film with a Nicolet iS50 FT-IR Spectrophotometer. High-resolution mass spectrometry data was acquired on a Bruker Esquire 3000 Plus Ion Trap Spectrophotometer.

Example 2

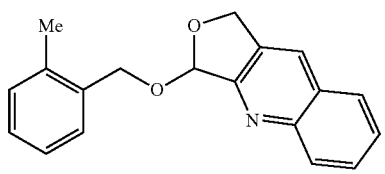

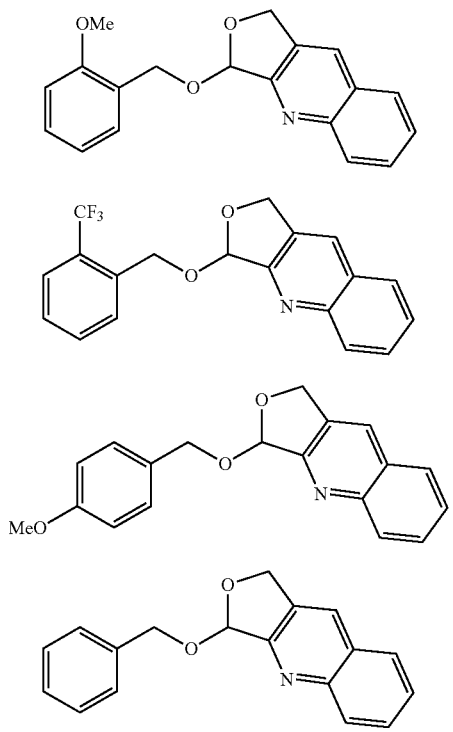

The attachment of scaffolds for compounds 1h, 1i, 1k, 1o, and 1p were previously described. Li et al. (2016) *Chem. Eur. J.* 22: 13054-13058.

Example 3

Acetal 1a:

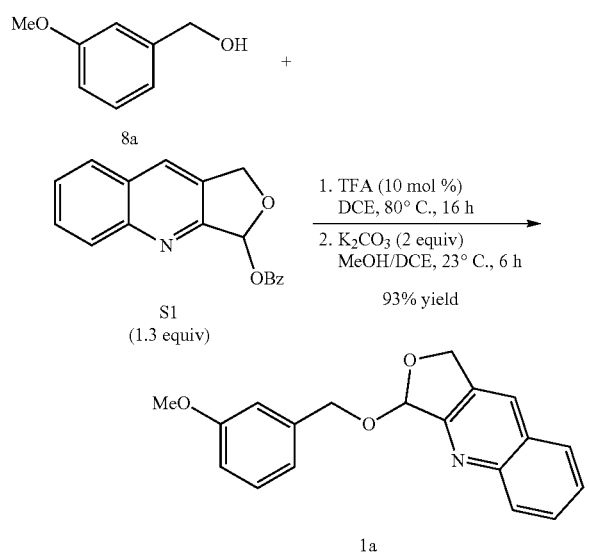

A 100 mL flask fitted with a reflux condenser was charged with (3-methoxyphenyl)methanol (8a, 830 mg, 6.01 mmol) and benzoate S1 (2.31 g, 7.94 mmol). These were dissolved in DCE (20.0 mL), and TFA (45.0 µL, 0.608 mmol) was added. The resulting mixture was heated to 80° C. and stirred for 16 h. After cooling to room temperature, $K_2CO_3$ (1.67 g, 12.1 mmol) and MeOH (20.0 mL) were added, and the resulting mixture was stirred at 23° C. for 6 h. The mixture was then filtered through a short pad of silica gel, eluting with EtOAc (100 mL), and the filtrate was concentrated under reduced pressure. The residue was purified by flash column chromatography (5:1:1 hexanes/EtOAc/$CH_2Cl_2$ eluent) to afford acetal 1a (1.72 g, 93% yield, $R_f$=0.17 in 5:1:1 hexanes/EtOAc/$CH_2Cl_2$) as a light yellow oil.

$^1$H NMR: (500 MHz, $CDCl_3$) δ 8.18 (d, J=8.5 Hz, 1H), 8.05 (s, 1H), 7.84 (d, J=7.9 Hz, 1H), 7.73 (ddd, J=8.5, 6.9, 1.3 Hz, 1H), 7.58 (ddd, J=7.9, 6.9, 1.1 Hz, 1H), 7.25 (t, J=8.1 Hz, 1H), 7.05-7.00 (m, 2H), 6.85-6.79 (m, 1H), 6.31 (d, J=0.9 Hz, 1H), 5.41 (d, J=13.1 Hz, 1H), 5.23 (dd, J=13.1, 0.9 Hz, 1H), 4.93 (d, J=11.6 Hz, 1H), 4.86 (d, J=11.6 Hz, 1H), 3.81 (s, 3H).

$^{13}$C NMR: (100 MHz, $CDCl_3$) δ 159.9, 159.6, 148.7, 139.4, 130.8, 130.0, 129.7, 129.6, 129.1, 128.12, 128.06, 127.3, 120.6, 113.8, 113.6, 103.7, 70.4, 70.1, 55.5.

IR: (film) 1266, 1073, 1022, 783, 756 $cm^{-1}$.

HRMS: (ESI+) m/z calc'd for $(M+H)+[C_{19}H_{17}NO_3+H]^+$: 308.1281, found 308.1284.

Example 4

Acetal 1b:

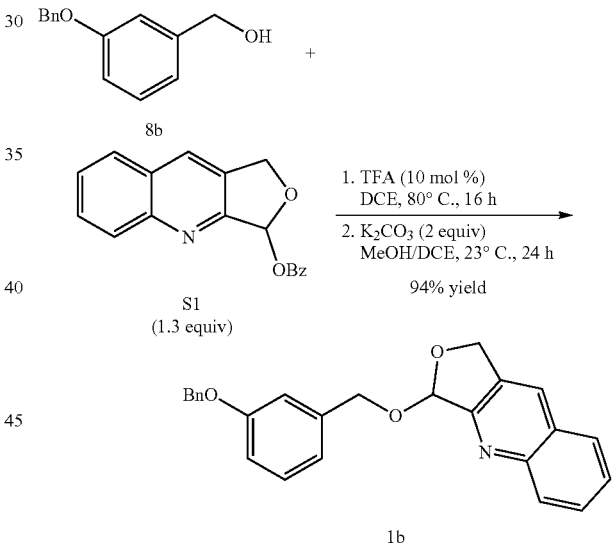

A 2-dram vial with a PTFE-lined cap was charged with (3-(benzyloxy)phenyl)methanol (8b, 65.3 mg, 0.305 mmol) and benzoate S1 (113 mg, 0.388 mmol). These were dissolved in DCE (1.00 mL), and TFA (2.2 µL, 0.0297 mmol) was added. The resulting mixture was heated to 80° C. and stirred for 16 h. After cooling to room temperature, $K_2CO_3$ (82.8 mg, 0.600 mmol) and MeOH (1.00 mL) were added, and the resulting mixture was stirred at 23° C. for 24 h. The mixture was then filtered through a short pad of silica gel, eluting with EtOAc (30 mL), and the filtrate was concentrated under reduced pressure. The residue was purified by flash column chromatography (4:1 hexanes/EtOAc eluent) to afford acetal 1b (110 mg, 94% yield, $R_f$=0.16 in 5:1 hexanes/EtOAc) as a colorless oil.

$^1$H NMR: (400 MHz, $CDCl_3$) δ 8.18 (d, J=8.5 Hz, 1H), 8.05 (s, 1H), 7.85 (d, J=8.1 Hz, 1H), 7.77-7.69 (m, 1H), 7.61-7.54 (m, 1H), 7.43 (d, J=7.3 Hz, 2H), 7.37 (t, J=7.3 Hz, 2H), 7.34-7.28 (m, 1H), 7.26 (t, J=7.9 Hz, 2H), 7.12 (s, 1H), 7.04 (d, J=7.6 Hz, 1H), 6.89 (dd, J=8.2, 2.4 Hz, 1H), 6.31 (s, 1H), 5.39 (d, J=13.3 Hz, 1H), 5.23 (d, J=13.3 Hz, 1H), 5.07 (s, 2H), 4.93 (d, J=11.6 Hz, 1H), 4.86 (d, J=11.6 Hz, 1H).
$^{13}$C NMR: (100 MHz, CDCl$_3$) δ 159.6, 159.1, 148.7, 139.4, 137.3, 130.8, 130.0, 129.7, 129.6, 129.1, 128.8, 128.10, 128.06, 127.8, 127.3, 120.9, 114.6, 114.5, 103.6, 70.4, 70.13, 70.12.

IR: (film) 1585, 1503, 1265, 1073, 1022 cm$^{-1}$.

HRMS: (ESI+) m/z calc'd for (M+H)+[C$_{25}$H$_{21}$NO$_3$+H]$^+$: 384.1594, found 384.1599.

Example 5

Acetal 1c:

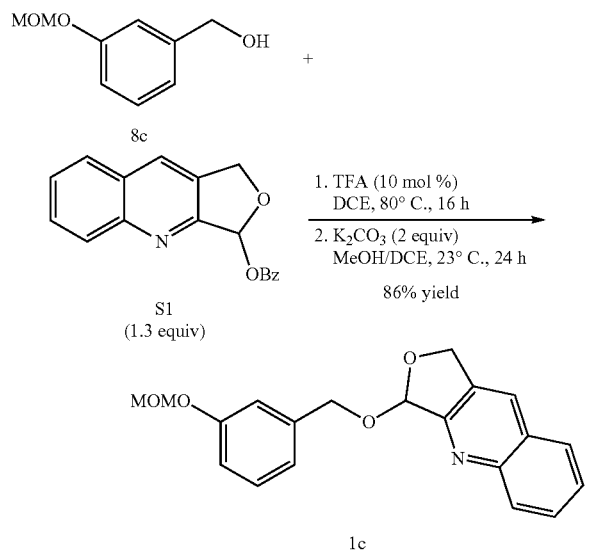

A 2-dram vial with a PTFE-lined cap was charged with alcohol 8c (50.1 mg, 0.298 mmol) and benzoate S1 (112 mg, 0.385 mmol). These were dissolved in DCE (1.00 mL), and TFA (2.2 µL, 0.0297 mmol) was added. The resulting mixture was heated to 80° C. and stirred for 16 h. After cooling to room temperature, K$_2$CO$_3$ (82.7 mg, 0.599 mmol) and MeOH (1.00 mL) were added, and the resulting mixture was stirred at 23° C. for 24 h. The mixture was then filtered through a short pad of silica gel, eluting with EtOAc (30 mL), and the filtrate was concentrated under reduced pressure. The residue was purified by flash column chromatography (2:1 hexanes/EtOAc eluent) to afford acetal 1c (86.9 mg, 86% yield, R$_f$=0.30 in 2:1 hexanes/EtOAc) as a colorless oil.

$^1$H NMR: (400 MHz, CDCl$_3$) δ 8.18 (d, J=8.5 Hz, 1H), 8.05 (s, 1H), 7.84 (d, J=8.1 Hz, 1H), 7.76-7.69 (m, 1H), 7.57 (app. t, J=7.5 Hz, 1H), 7.26 (app. t, J=7.9 Hz, 1H), 7.13 (s, 1H), 7.09 (d, J=7.6 Hz, 1H), 6.95 (dd, J=8.1, 2.3 Hz, 1H), 6.31 (s, 1H), 5.41 (d, J=13.3 Hz, 1H), 5.23 (d, J=13.3 Hz, 1H), 5.18 (s, 2H), 4.92 (d, J=11.5 Hz, 1H), 4.84 (d, J=11.5 Hz, 1H), 3.47 (s, 3H).

$^{13}$C NMR: (100 MHz, CDCl$_3$) δ 159.6, 157.5, 148.7, 139.5, 130.8, 130.0, 129.69, 129.66, 129.1, 128.11, 128.05, 127.3, 121.9, 116.2, 115.8, 103.7, 94.6, 70.4, 70.1, 56.2.

IR: (film) 1256, 1150, 1077, 1008, 920 cm$^{-1}$.

HRMS: (ESI+) m/z calc'd for (M+H)$^+$ [C$_{20}$H$_{19}$NO$_4$+H]$^+$: 338.1387, found 338.1390.

Example 6

Acetal 1d:

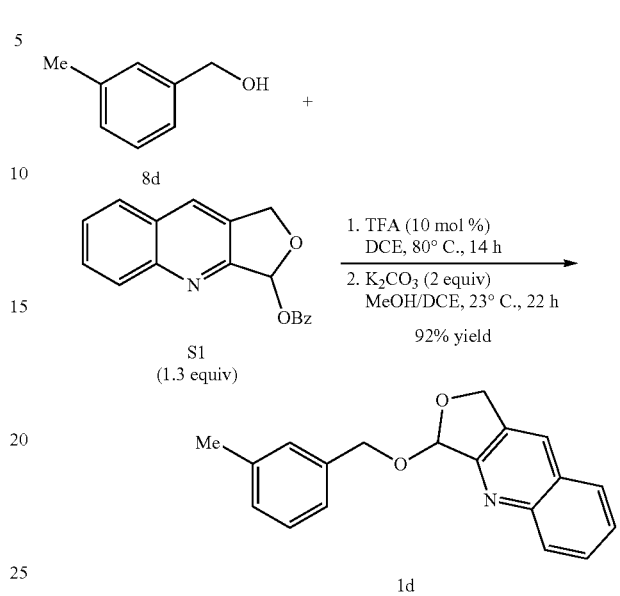

A 2-dram vial with a PTFE-lined cap was charged with m-tolylmethanol (8d, 74.5 mg, 0.611 mmol) and benzoate S1 (227 mg, 0.780 mmol). These were dissolved in DCE (2.00 mL), and TFA (4.5 µL, 0.0608 mmol) was added. The resulting mixture was heated to 80° C. and stirred for 14 h. After cooling to room temperature, K$_2$CO$_3$ (166 mg, 1.20 mmol) and MeOH (2.00 mL) were added, and the resulting mixture was stirred at 23° C. for 22 h. The mixture was then filtered through a short pad of silica gel, eluting with EtOAc (50 mL), and the filtrate was concentrated under reduced pressure. The residue was purified by flash column chromatography (5:1:1 hexanes/EtOAc/CH$_2$Cl$_2$ eluent) to afford acetal 1d (164 mg, 93% yield, R$_f$=0.31 in 3:1 hexanes/EtOAc) as a white solid.

$^1$H NMR: (400 MHz, CDCl$_3$) δ 8.19 (d, J=8.5 Hz, 1H), 8.04 (s, 1H), 7.83 (d, J=8.1 Hz, 1H), 7.72 (ddd, J=8.5, 7.0, 1.4 Hz, 1H), 7.57 (ddd, J=8.1, 7.0, 1.1 Hz, 1H), 7.27 (s, 1H), 7.25-7.20 (m, 2H), 7.12-7.05 (m, 1H), 6.31 (d, J=0.8 Hz, 1H), 5.41 (d, J=13.2 Hz, 1H), 5.23 (dd, J=13.2, 0.8 Hz, 1H), 4.92 (d, J=11.3 Hz, 1H), 4.84 (d, J=11.3 Hz, 1H), 2.34 (s, 3H).

$^{13}$C NMR: (100 MHz, CDCl$_3$) δ 159.7, 148.7, 138.2, 137.6, 130.8, 130.0, 129.7, 129.2, 129.1, 128.7, 128.5, 128.1, 128.0, 127.3, 125.6, 103.6, 70.6, 70.1, 21.6.

IR: (film) 1504, 1074, 1022, 1008, 756 cm$^{-1}$.

HRMS: (ESI+) m/z calc'd for (M+H)$^+$ [C$_{19}$H$_{17}$NO$_2$+H]$^+$: 292.1332, found 292.1335.

Example 7

Acetal 1e:

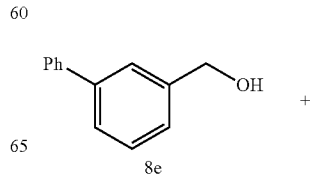

-continued

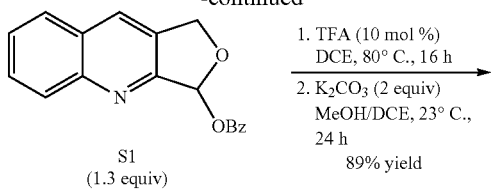

S1
(1.3 equiv)

1. TFA (10 mol %)
DCE, 80° C., 16 h
2. K₂CO₃ (2 equiv)
MeOH/DCE, 23° C., 24 h

89% yield

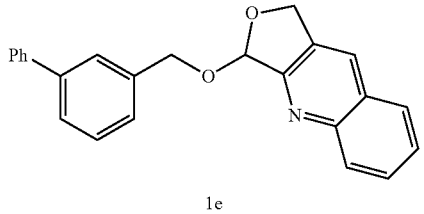

1e

A 2-dram vial with a PTFE-lined cap was charged with [1,1'-biphenyl]-3-ylmethanol (8e, 54.9 mg, 0.298 mmol) and benzoate S1 (115 mg, 0.395 mmol). These were dissolved in DCE (1.00 mL), and TFA (2.2 µL, 0.0297 mmol) was added. The resulting mixture was heated to 80° C. and stirred for 16 h. After cooling to room temperature, K₂CO₃ (83.3 mg, 0.604 mmol) and MeOH (1.00 mL) were added, and the resulting mixture was stirred at 23° C. for 24 h. The mixture was then filtered through a short pad of silica gel, eluting with EtOAc (30 mL), and the filtrate was concentrated under reduced pressure. The residue was purified by flash column chromatography (4:1 hexanes/EtOAc eluent) to afford acetal 1e, still containing some residual benzoate S1. The impure material was dissolved in MeOH (2.00 mL) and CH₂Cl₂ (2.00 mL), K₂CO₃ (82.8 mg, 0.600 mmol) was then added, and the resulting mixture was stirred at 23° C. for another 23 h. The mixture was then filtered through a short pad of silica gel, eluting with EtOAc (30 mL), and the filtrate was concentrated under reduced pressure. The residue was purified by flash column chromatography (2:1 hexanes/EtOAc eluent) to afford acetal 1e (93.9 mg, 89% yield, $R_f$=0.29 in 3:1 hexanes/EtOAc) as a colorless oil.

¹H NMR: (400 MHz, CDCl₃) δ 8.19 (d, J=8.5 Hz, 1H), 8.06 (s, 1H), 7.84 (d, J=8.1 Hz, 1H), 7.76-7.70 (m, 1H), 7.69 (s, 1H), 7.63-7.55 (m, 3H), 7.51 (app. dt, J=6.6, 1.9 Hz, 1H), 7.46-7.39 (m, 4H), 7.34 (app. t, J=7.3 Hz, 1H), 6.36 (s, 1H), 5.42 (d, J=13.2 Hz, 1H), 5.25 (d, J=13.2 Hz, 1H), 5.02 (d, J=11.5 Hz, 1H), 4.94 (d, J=11.5 Hz, 1H).

¹³C NMR: (100 MHz, CDCl₃) δ 159.6, 148.7, 141.6, 141.3, 138.3, 130.8, 130.0, 129.7, 129.13, 129.05, 128.9, 128.11, 128.05, 127.45, 127.44, 127.38, 127.3, 126.8, 103.7, 70.6, 70.2.

IR: (film) 1504, 1075, 1022, 756, 700 cm⁻¹.

HRMS: (ESI+) m/z calc'd for (M+H)⁺ [C₂₄H₁₉NO₂+H]⁺: 354.1489, found 354.1496.

Example 8

Acetal 1f:

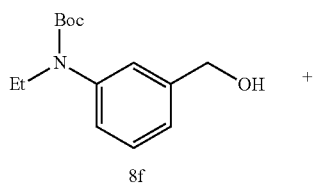

8f

-continued

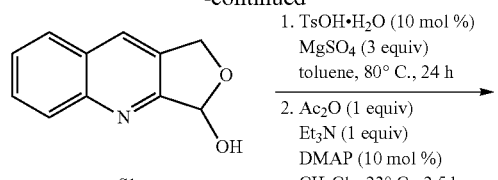

S1
(1.1 equiv)

1. TsOH·H₂O (10 mol %)
MgSO₄ (3 equiv)
toluene, 80° C., 24 h
2. Ac₂O (1 equiv)
Et₃N (1 equiv)
DMAP (10 mol %)
CH₂Cl₂, 23° C., 2.5 h 63% yield

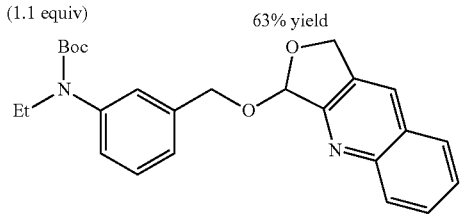

1f

A 2-dram vial with a PTFE-lined cap was charged with alcohol 8f (125 mg, 0.498 mmol), TsOH·H₂O (9.6 mg, 0.0505 mmol), MgSO₄ (180 mg, 1.50 mmol), hemiacetal S1 (103 mg, 0.551 mmol), and toluene (2.00 mL). The resulting mixture was heated to 80° C. and stirred for 24 h. After cooling to room temperature, the mixture was filtered through a short pad of silica gel, eluting with EtOAc (30.0 mL), and the filtrate was concentrated under reduced pressure. The residue was purified by flash column chromatography (2:1 hexanes/EtOAc eluent) to afford a mixture of acetal 1f and unreacted alcohol 8f (181 mg total). This mixture was then dissolved in CH₂Cl₂ (2.00 mL), and Et₃N (70.0 µL, 0.503 mmol), Ac₂O (50.0 µL, 0.529 mmol), and DMAP (6.1 mg, 0.0500 mmol) were added sequentially. Then resulting mixture was stirred at 23° C. for 2.5 h, and then it was concentrated under reduced pressure. The residue was purified by flash column chromatography (5:1:1→3:1:1 hexanes/EtOAc/CH₂Cl₂ eluent) to afford acetal 1f (133 mg, 63% yield, $R_f$=0.37 in 2:1 hexanes/EtOAc) as a yellow oil.

¹H NMR: (500 MHz, CDCl₃) δ 8.18 (d, J=8.5 Hz, 1H), 8.06 (s, 1H), 7.85 (d, J=8.0 Hz, 1H), 7.73 (ddd, J=8.5, 7.0, 1.3 Hz, 1H), 7.58 (ddd, J=8.0, 7.0, 1.1 Hz, 1H), 7.32-7.26 (m, 3H), 7.10 (d, J=6.8 Hz, 1H), 6.31 (d, J=0.7 Hz, 1H), 5.40 (d, J=13.2 Hz, 1H), 5.24 (dd, J=13.2, 0.7 Hz, 1H), 4.93 (d, J=11.6 Hz, 1H), 4.85 (d, J=11.6 Hz, 1H), 3.66 (q, J=7.1 Hz, 2H), 1.40 (s, 9H), 1.13 (t, J=7.1 Hz, 3H).

¹³C NMR: (100 MHz, CDCl₃) δ 159.6, 154.7, 148.7, 142.7, 138.5, 130.7, 130.0, 129.7, 129.1, 128.8, 128.11, 128.06, 127.3, 126.8, 126.7, 125.8, 103.7, 80.1, 70.2, 45.1, 28.5, 14.1.

IR: (film) 1694, 1391, 1366, 1150, 1010 cm⁻¹.

HRMS: (ESI+) m/z calc'd for (M+H)⁺ [C₂₅H₂₈N₂O₄+H]⁺: 421.2122, found 421.2127.

Example 9

Acetal 1g:

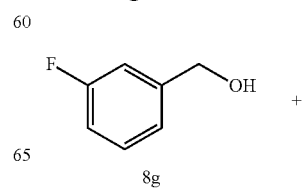

8g

+

A 2-dram vial with a PTFE-lined cap was charged with (3-fluorophenyl)methanol (8 g, 76.4 mg, 0.606 mmol) and benzoate S1 (227 mg, 0.780 mmol). These were dissolved in DCE (2.00 mL), and TFA (4.5 µL, 0.0608 mmol) was added. The resulting mixture was heated to 80° C. and stirred for 16 h. After cooling to room temperature, K$_2$CO$_3$ (165 mg, 1.20 mmol) and MeOH (2.00 mL) were added, and the resulting mixture was stirred at 23° C. for 24 h. The mixture was then filtered through a short pad of silica gel, eluting with EtOAc (50 mL), and the filtrate was concentrated under reduced pressure. The residue was purified by flash column chromatography (5:1:1 hexanes/EtOAc/CH$_2$Cl$_2$ eluent) to afford acetal 1g (166 mg, 93% yield, R$_f$=0.38 in 3:1:1 hexanes/EtOAc/CH$_2$Cl$_2$) as a white solid.

$^1$H NMR: (400 MHz, CDCl$_3$) δ 8.19 (d, J=8.5 Hz, 1H), 8.06 (s, 1H), 7.85 (d, J=8.2 Hz, 1H), 7.78-7.70 (m, 1H), 7.62-7.54 (m, 1H), 7.33-7.26 (m, 1H), 7.23-7.14 (m, 2H), 6.96 (app. td, J=8.4, 2.1 Hz, 1H), 6.31 (s, 1H), 5.40 (d, J=13.2 Hz, 1H), 5.24 (d, J=13.2 Hz, 1H), 4.93 (d, J=11.9 Hz, 1H), 4.86 (d, J=11.9 Hz, 1H).

$^{13}$C NMR: (100 MHz, CDCl$_3$) δ 163.1 (d, J=245.8 Hz), 159.4, 148.7, 140.5 (d, J=7.3 Hz), 130.7, 130.1, 130.0, 129.8, 129.2, 128.2, 128.1, 127.4, 123.6 (d, J=2.8 Hz), 115.1 (d, J=21.8 Hz), 114.8 (d, J=21.0 Hz), 103.8, 70.2, 69.7 (d, J=1.6 Hz).

$^{19}$F NMR: (376 MHz, CDCl$_3$) δ −113.4.

IR: (film) 1504, 1070, 1024, 783, 756 cm$^{-1}$.

HRMS: (ESI+) m/z calc'd for (M+H)$^+$ [C$_{18}$H$_{14}$FNO$_2$+H]$^+$: 296.1081, found 296.1084.

Example 10

Acetal 1j:

A 2-dram vial with a PTFE-lined cap was charged with (2-chlorophenyl)methanol (8j, 86.7 mg, 0.606 mmol) and benzoate S1 (227 mg, 0.780 mmol). These were dissolved in DCE (2.00 mL), and TFA (4.5 µL, 0.0608 mmol) was added. The resulting mixture was heated to 80° C. and stirred for 16 h. After cooling to room temperature, K$_2$CO$_3$ (166 mg, 1.20 mmol) and MeOH (2.00 mL) were added, and the resulting mixture was stirred at 23° C. for 24 h. The mixture was then filtered through a short pad of silica gel, eluting with EtOAc (50 mL), and the filtrate was concentrated under reduced pressure. The residue was purified by flash column chromatography (4:1:1 hexanes/EtOAc/CH$_2$Cl$_2$ eluent) to afford acetal 1j (181 mg, 96% yield, R$_f$=0.50 in 3:1:1 hexanes/EtOAc/CH$_2$Cl$_2$) as a white solid.

$^1$H NMR: (400 MHz, CDCl$_3$) δ 8.20 (d, J=8.5 Hz, 1H), 8.07 (s, 1H), 7.85 (d, J=8.2 Hz, 1H), 7.74 (ddd, J=8.5, 6.9, 1.4 Hz, 1H), 7.62-7.55 (m, 2H), 7.34 (dd, J=7.6, 1.5 Hz, 1H), 7.28-7.17 (m, 2H), 6.35 (d, J=0.9 Hz, 1H), 5.42 (d, J=13.2 Hz, 1H), 5.24 (dd, J=13.2, 0.9 Hz, 1H), 5.08 (d, J=12.8 Hz, 1H), 4.96 (d, J=12.8 Hz, 1H).

$^{13}$C NMR: (100 MHz, CDCl$_3$) δ 159.5, 148.7, 135.8, 133.1, 130.8, 130.0, 129.73, 129.66, 129.4, 129.2, 128.9, 128.2, 128.1, 127.4, 127.0, 104.0, 70.3, 67.5.

IR: (film) 1504, 1081, 1023, 1010, 753 cm$^{-1}$.

HRMS: (ESI+) m/z calc'd for (M+H)$^+$ [C$_{18}$H$_{14}$ClNO$_2$+H]$^+$: 312.0786, found 312.0791.

Example 11

Acetal 1l:

A 2-dram vial with a PTFE-lined cap was charged with 3,4-(methylenedioxy)phenylmethanol (8l, 91.6 mg, 0.603 mmol) and benzoate S1 (230 mg, 0.790 mmol). These were dissolved in DCE (2.00 mL), and TFA (4.5 µL, 0.0608 mmol) was added. The resulting mixture was heated to 80° C. and stirred for 15.5 h. After cooling to room temperature, $K_2CO_3$ (166 mg, 1.20 mmol) and MeOH (2.00 mL) were added, and the resulting mixture was stirred at 23° C. for 24 h. The mixture was then filtered through a short pad of silica gel, eluting with EtOAc (50.0 mL), and the filtrate was concentrated under reduced pressure. The residue was purified by flash column chromatography (3:1:1 hexanes/EtOAc/$CH_2Cl_2$ eluent) to afford acetal 1l (180 mg, 93% yield, $R_f$=0.19 in 3:1 hexanes/EtOAc) as a light yellow oil.

$^1$H NMR: (500 MHz, $CDCl_3$) δ 8.18 (d, J=8.5 Hz, 1H), 8.05 (s, 1H), 7.84 (d, J=8.0 Hz, 1H), 7.72 (ddd, J=8.5, 7.0, 1.4 Hz, 1H), 7.57 (ddd, J=8.0, 7.0, 1.1 Hz, 1H), 6.97 (d, J=1.5 Hz, 1H), 6.90 (dd, J=7.9, 1.5 Hz, 1H), 6.77 (d, J=7.9 Hz, 1H), 6.28 (d, J=0.8 Hz, 1H), 5.93 (s, 2H), 5.40 (d, J=13.1 Hz, 1H), 5.23 (dd, J=13.1, 0.8 Hz, 1H), 4.84 (d, J=11.1 Hz, 1H), 4.77 (d, J=11.1 Hz, 1H).

$^{13}$C NMR: (100 MHz, $CDCl_3$) δ 159.7, 148.7, 147.9, 147.5, 131.6, 130.8, 130.0, 129.7, 129.1, 128.1, 128.0, 127.3, 122.2, 109.3, 108.3, 103.4, 101.2, 70.4, 70.1.

IR: (film) 1503, 1491, 1444, 1251, 1009 cm$^{-1}$.

HRMS: (ESI+) m/z calc'd for (M+H)$^+$ [$C_{19}H_{15}NO_4$+H]$^+$: 322.1074, found 322.1076.

Example 12

Acetal 1m:

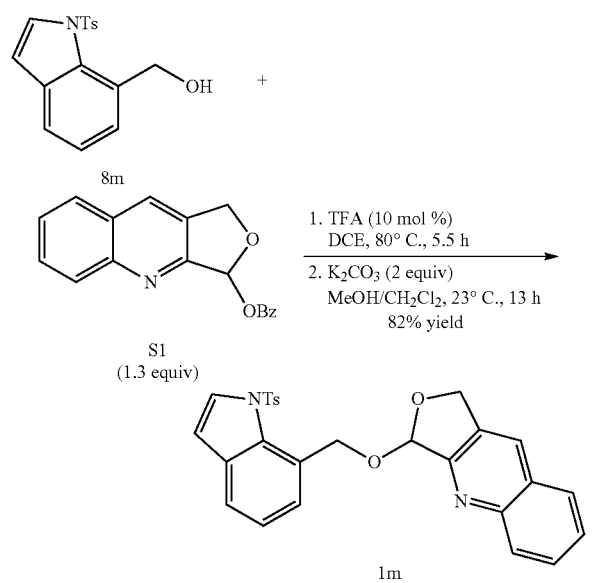

A 2-dram vial with a PTFE-lined cap was charged with alcohol 8m (201 mg, 0.668 mmol) and benzoate S1 (266 mg, 0.914 mmol). These were dissolved in DCE (2.30 mL), and TFA (5.2 µL, 0.0702 mmol) was added. The resulting mixture was heated to 80° C. and stirred for 5.5 h. After cooling to room temperature, the solvent was removed under reduced pressure. The residue was then dissolved in MeOH (3.00 mL) and $CH_2Cl_2$ (3.00 mL), $K_2CO_3$ (194 mg, 1.41 mmol) was added, and the resulting mixture was stirred at 23° C. for 13 h. The mixture was then filtered through a short pad of silica gel, eluting with EtOAc (30 mL), and the filtrate was concentrated under reduced pressure. The residue was purified by flash column chromatography (5:1:1 hexanes/EtOAc/$CH_2Cl_2$ eluent) to afford acetal 1m (257 mg, 82% yield, $R_f$=0.39 in 3:1 hexanes/EtOAc) as a white solid.

$^1$H NMR: (400 MHz, $CDCl_3$) δ 8.18 (d, J=8.5 Hz, 1H), 8.08 (s, 1H), 7.87 (d, J=8.1 Hz, 1H), 7.78-7.72 (m, 1H), 7.67 (d, J=3.8 Hz, 1H), 7.64-7.56 (m, 2H), 7.48 (d, J=8.4 Hz, 2H), 7.41 (d, J=7.3 Hz, 1H), 7.22 (app. t, J=7.7 Hz, 1H), 7.02 (d, J=8.2 Hz, 2H), 6.67 (d, J=3.8 Hz, 1H), 6.37 (s, 1H), 5.41 (d, J=13.5 Hz, 1H), 5.30 (s, 2H), 5.23 (d, J=13.5 Hz, 1H), 2.25 (s, 3H).

$^{13}$C NMR: (100 MHz, $CDCl_3$) δ 159.7, 148.7, 144.7, 135.9, 133.3, 133.2, 131.1, 130.2, 130.0, 129.9, 129.7, 129.0, 128.1, 127.3, 126.8, 126.0, 125.4, 124.3, 120.8, 110.3, 103.9, 70.3, 67.3, 21.7.

IR: (film) 1173, 1087, 1008, 729, 679 cm$^{-1}$.

HRMS: (ESI+) m/z calc'd for (M+H)$^+$ [$C_{27}H_{22}N_2O_4S$+H]$^+$: 471.1373, found 471.1382.

Example 13

Acetal 1n:

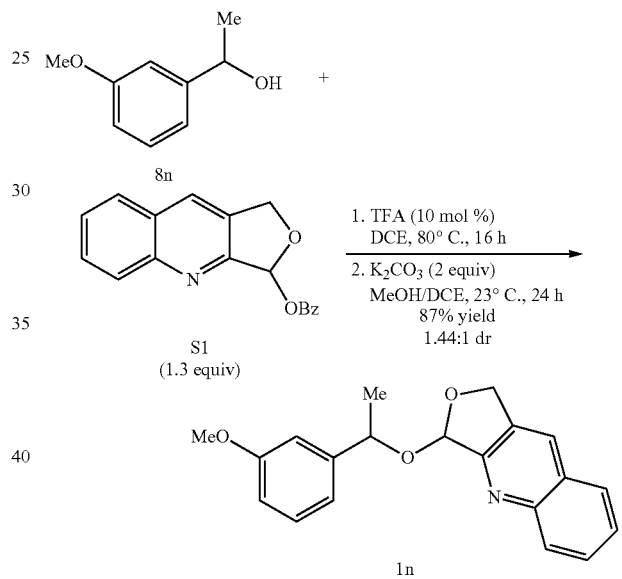

A 2-dram vial with a PTFE-lined cap was charged with 1-(3-methoxyphenyl)ethanol (8n, 46.2 mg, 0.304 mmol) and benzoate S1 (113 mg, 0.388 mmol). These were dissolved in DCE (1.00 mL), and TFA (2.2 µL, 0.0297 mmol) was added. The resulting mixture was heated to 80° C. and stirred for 16 h. After cooling to room temperature, $K_2CO_3$ (82.8 mg, 0.600 mmol) and MeOH (1.00 mL) were added, and the resulting mixture was stirred at 23° C. for 24 h. The mixture was then filtered through a short pad of silica gel, eluting with EtOAc (30 mL), and the filtrate was concentrated under reduced pressure. The residue was purified by flash column chromatography (4:1 hexanes/EtOAc eluent) to afford acetal 1n (85.0 mg, 87% yield, 1.44:1 dr, $R_f$=0.54, 0.46 in 2:1 hexanes/EtOAc) as a colorless oil.

$^1$H NMR: (400 MHz, $CDCl_3$) δ 8.19 (d, J=8.5 Hz, 0.41H), 8.15 (d, J=8.5 Hz, 0.59H), 8.03 (s, 0.59H), 8.02 (s, 0.41H), 7.83 (d, J=8.1 Hz, 1H), 7.76-7.67 (m, 1H), 7.61-7.53 (m, 1H), 7.33 (app. t, J=7.9 Hz, 0.59H), 7.28-7.21 (m, 0.41H), 7.20 (d, J=7.5 Hz, 0.59H), 7.11 (d, J=7.5 Hz, 0.59H), 7.02-6.95 (m, 0.82H), 6.87 (dd, J=8.1, 2.3 Hz, 0.59H), 6.79 (dd, J=8.2, 2.2 Hz, 0.41H), 6.34 (s, 0.41H), 6.07 (s, 0.59H), 5.40 (d, J=13.1

Hz, 0.59H), 5.23-5.15 (m, 1H), 5.15-5.06 (m, 1.41H), 3.92 (s, 1.77H), 3.79 (s, 1.23H), 1.61 (d, J=6.5 Hz, 1.23H), 1.53 (d, J=6.6 Hz, 1.77H).

$^{13}$C NMR: (100 MHz, CDCl$_3$) δ 160.2, 160.13, 160.06, 159.8, 148.8, 148.6, 146.4, 144.7, 130.88, 130.86, 130.1, 130.0, 129.8, 129.6, 129.5, 129.1, 128.9, 128.1, 128.04, 128.00, 127.2, 127.1, 119.4, 118.6, 113.8, 112.9, 112.0, 111.8, 103.2, 101.7, 75.5, 69.8, 55.5, 55.4, 24.6, 23.5.

IR: (film) 1504, 1257, 1008, 783, 756 cm$^{-1}$.

HRMS: (ESI+) m/z calc'd for (M+H)$^+$ [C$_{20}$H$_{19}$NO$_3$+H]$^+$: 322.1438, found 322.1440.

Example 14

Meta-C—H Functionalization of Benzylic Alcohol Acetals- General Procedure for Meta-C—H Arylation of QuA-Attached Alcohols:

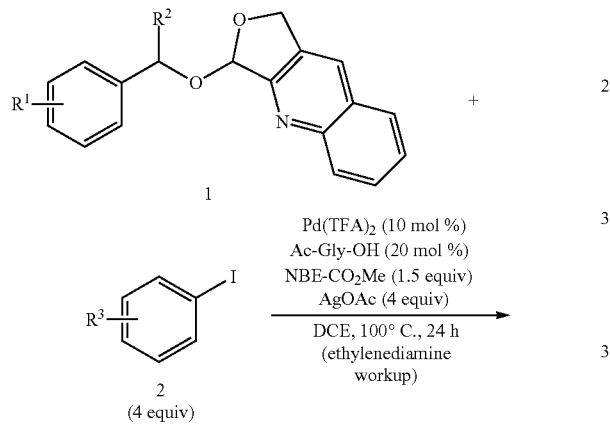

A suspension of substrate acetal, aryl iodide (4.00 equiv), NBE-CO$_2$Me (1.5 equiv), Pd(TFA)$_2$ (10.0 mol %), TFA-Gly-OH (20.0 mol %), and AgOAc (4.00 equiv) in DCE (50.0 mM) in a 2-dram vial with a PTFE-lined cap was heated at 100° C. and stirred for 24 h. After cooling to ambient temperature, ethylenediamine (0.100 mL) was added, and the resulting mixture was stirred at 23° C. for 2 h to remove the Pd catalyst complex, which is difficult to chromatographically separate from the arylation product. Then the mixture was filtered through a short pad of silica gel, eluting with EtOAc (50 mL). The filtrate was concentrated by rotary evaporation, and the resulting residue was purified by flash column chromatography to afford the arylation product.

Example 15

Arylation Product 3aa:

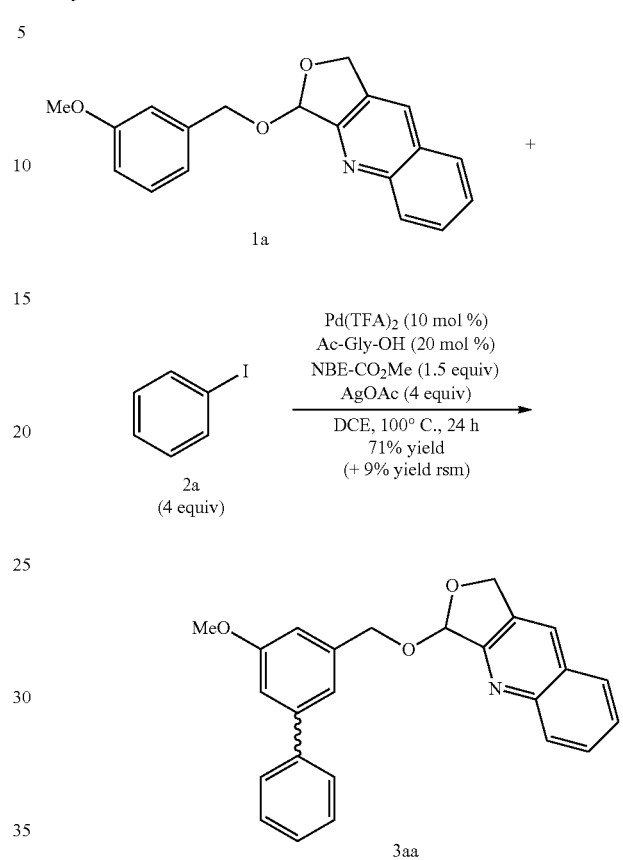

To a 2-dram vial with a PTFE-lined cap was charged with acetal 1a (1.00 mL, 0.100 M in DCE, 0.100 mmol), PhI (81.1 mg, 0.398 mmol), NBE-CO$_2$Me (22.6 mg, 0.149 mmol), Pd(TFA)$_2$ (3.2 mg, 0.00964 mmol), TFA-Gly-OH (3.3 mg, 0.0193 mmol), AgOAc (66.6 mg, 0.399 mmol), and DCE (1.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (5:1:1 hexanes/EtOAc/CH$_2$Cl$_2$ eluent) to afford arylation product 3aa (29.7 mg, 71% yield+9% recovered 1a, R$_f$=0.18 in 5:1:1 hexanes/EtOAc/CH$_2$Cl$_2$) as a light yellow oil.

$^1$H NMR: (400 MHz, CDCl$_3$) δ 8.19 (d, J=8.5 Hz, 1H), 8.04 (s, 1H), 7.83 (d, J=8.1 Hz, 1H), 7.76-7.69 (m, 1H), 7.63-7.53 (m, 3H), 7.42 (t, J=7.5 Hz, 2H), 7.34 (t, J=7.3 Hz, 1H), 7.28 (s, 1H), 7.07-7.01 (m, 2H), 6.35 (s, 1H), 5.42 (d, J=13.2 Hz, 1H), 5.24 (d, J=13.2 Hz, 1H), 4.99 (d, J=11.6 Hz, 1H), 4.92 (d, J=11.6 Hz, 1H), 3.87 (s, 3H).

$^{13}$C NMR: (100 MHz, CDCl$_3$) δ 160.3, 159.6, 148.7, 142.9, 141.2, 139.7, 130.7, 129.9, 129.7, 129.1, 128.9, 128.1, 128.0, 127.6, 127.4, 127.3, 119.7, 112.8, 112.4, 103.7, 70.5, 70.1, 55.6.

IR: (film) 1596, 1463, 1215, 1022, 762 cm$^{-1}$.

HRMS: (ESI+) m/z calc'd for (M+H)$^+$ [O$_{25}$H$_{21}$NO$_3$+H]$^+$: 384.1594, found 384.1596.

Example 16

Arylation Product 3ab:

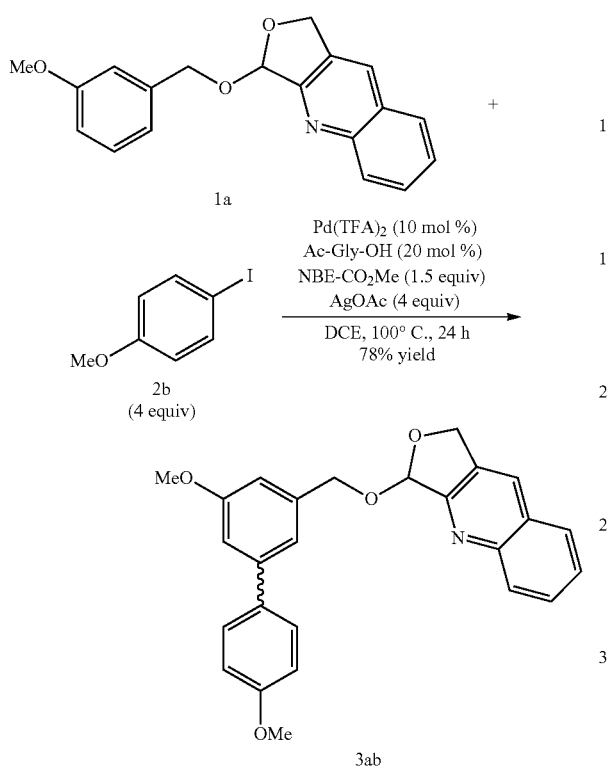

3ab

To a 2-dram vial with a PTFE-lined cap was charged with acetal 1a (1.00 mL, 0.100 M in DCE, 0.100 mmol), 1-iodo-4-methoxybenzene (93.2 mg, 0.398 mmol), NBE-CO$_2$Me (21.9 mg, 0.144 mmol), Pd(TFA)$_2$ (3.4 mg, 0.0102 mmol), TFA-Gly-OH (3.4 mg, 0.0199 mmol), AgOAc (67.8 mg, 0.406 mmol), and DCE (1.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (4:1:1 hexanes/EtOAc/CH$_2$Cl$_2$ eluent) to afford arylation product 3ab (32.4 mg, 78% yield, R$_f$=0.18 in 3:1 hexanes/EtOAc) as a colorless oil. (6% recovery of starting material 1a was observed in the crude NMR prior to purification.)

$^1$H NMR: (400 MHz, CDCl$_3$) δ 8.18 (d, J=8.5 Hz, 1H), 8.04 (s, 1H), 7.83 (d, J=7.9 Hz, 1H), 7.76-7.68 (m, 1H), 7.60-7.49 (m, 3H), 7.24 (s, 1H), 7.03-7.00 (m, 1H), 6.98 (s, 1H), 6.96 (d, J=8.8 Hz, 2H), 6.35 (s, 1H), 5.42 (d, J=13.5 Hz, 1H), 5.23 (d, J=13.5 Hz, 1H), 4.97 (d, J=11.6 Hz, 1H), 4.91 (d, J=11.6 Hz, 1H), 3.86 (s, 3H), 3.84 (s, 3H).

$^{13}$C NMR: (100 MHz, CDCl$_3$) δ 160.3, 159.6, 159.4, 148.7, 142.5, 139.7, 133.7, 130.8, 129.9, 129.7, 129.1, 128.4, 128.10, 128.05, 127.3, 119.3, 114.3, 112.4, 111.8, 103.7, 70.5, 70.1, 55.6, 55.5.

IR: (film) 1516, 1249, 1023, 909, 732 cm$^{-1}$.

HRMS: (ESI+) m/z calc'd for (M+H)$^+$ [C$_{26}$H$_{23}$NO$_4$+H]$^+$: 414.1700, found 414.1703.

Example 17

Arylation Product 3ac:

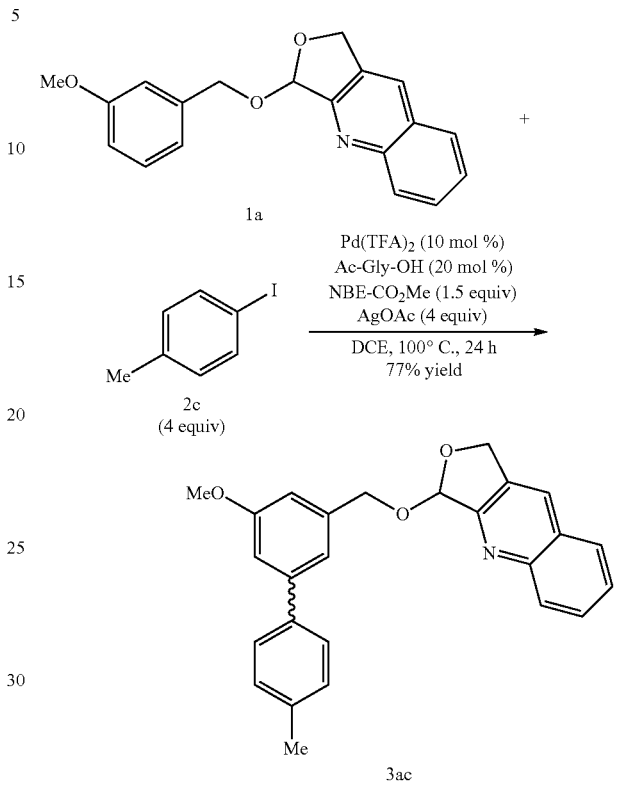

3ac

To a 2-dram vial with a PTFE-lined cap was charged with acetal 1a (1.00 mL, 0.100 M in DCE, 0.100 mmol), 1-iodo-4-methylbenzene (89.0 mg, 0.408 mmol), NBE-CO$_2$Me (23.5 mg, 0.155 mmol), Pd(TFA)$_2$ (3.3 mg, 0.00994 mmol), TFA-Gly-OH (3.5 mg, 0.0205 mmol), AgOAc (66.5 mg, 0.398 mmol), and DCE (1.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (5:1:1 hexanes/EtOAc/CH$_2$Cl$_2$ eluent) to afford arylation product 3ac (30.7 mg, 77% yield, R$_f$=0.33 in 2:1 hexanes/EtOAc) as a colorless oil. (4% recovery of starting material 1a was observed in the crude NMR prior to purification.)

$^1$H NMR: (400 MHz, CDCl$_3$) δ 8.18 (d, J=8.5 Hz, 1H), 8.05 (s, 1H), 7.84 (d, J=8.1 Hz, 1H), 7.76-7.69 (m, 1H), 7.61-7.54 (m, 1H), 7.49 (d, J=8.0 Hz, 2H), 7.26 (s, 1H), 7.23 (d, J=8.0 Hz, 2H), 7.07-7.02 (m, 1H), 7.01 (s, 1H), 6.35 (s, 1H), 5.42 (d, J=13.2 Hz, 1H), 5.24 (dd, J=13.2, 0.8 Hz, 1H), 4.98 (d, J=11.6 Hz, 1H), 4.91 (d, J=11.6 Hz, 1H), 3.86 (s, 3H), 2.39 (s, 3H).

$^{13}$C NMR: (100 MHz, CDCl$_3$) δ 160.3, 159.6, 148.7, 142.9, 139.7, 138.3, 137.4, 130.8, 130.0, 129.7, 129.6, 129.1, 128.12, 128.05, 127.3, 119.6, 112.7, 112.1, 103.7, 70.5, 70.2, 55.6, 21.3.

IR: (film) 1595, 1504, 1459, 1021, 816 cm$^{-1}$.

HRMS: (ESI+) m/z calc'd for (M+H)$^+$ [C$_{26}$H$_{23}$NO$_3$+H]$^+$: 398.1751, found 398.1751.

Example 18

Arylation Product 3ad:

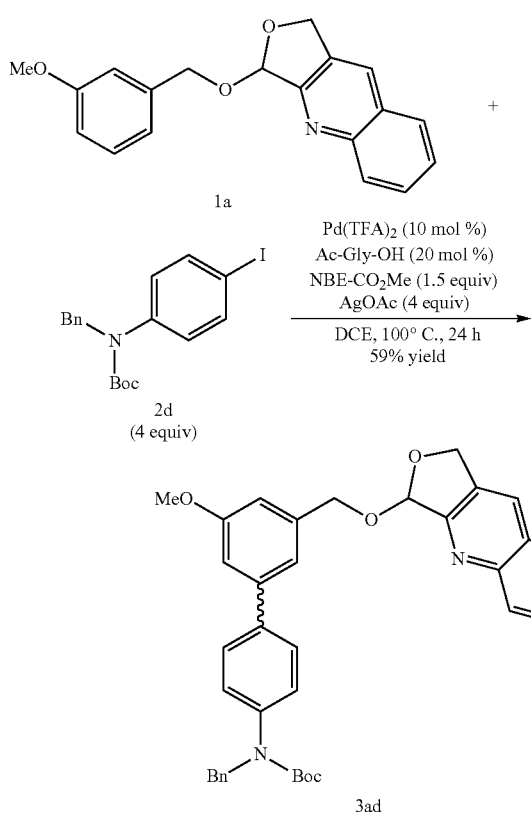

To a 2-dram vial with a PTFE-lined cap was charged with acetal 1a (1.00 mL, 0.100 M in DCE, 0.100 mmol), tert-butyl benzyl(4-iodophenyl)carbamate (2d) (Shen et al., (2015) *J. Am. Chem. Soc.* 137: 11574-11577), 165 mg, 0.403 mmol), NBE-CO$_2$Me (23.5 mg, 0.155 mmol), Pd(TFA)$_2$ (3.4 mg, 0.0102 mmol), TFA-Gly-OH (3.4 mg, 0.0199 mmol), AgOAc (65.5 mg, 0.392 mmol), and DCE (1.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (3:1 hexanes/EtOAc eluent) to afford arylation product 3ad (34.6 mg, 59% yield, R$_f$=0.22 in 2:1 hexanes/EtOAc) as a light yellow oil. (31% recovery of starting material 1a was observed in the crude NMR prior to purification.)

$^1$H NMR: (400 MHz, CDCl$_3$) δ 8.09 (d, J=8.5 Hz, 1H), 7.97 (s, 1H), 7.76 (d, J=8.0 Hz, 1H), 7.68-7.61 (m, 1H), 7.54-7.48 (m, 1H), 7.41 (d, J=8.5 Hz, 2H), 7.28-7.09 (m, 8H), 6.92 (app. d, J=0.8 Hz, 2H), 6.26 (s, 1H), 5.34 (d, J=13.3 Hz, 1H), 5.16 (d, J=13.3 Hz, 1H), 4.89 (d, J=11.6 Hz, 1H), 4.82 (d, J=11.6 Hz, 1H), 4.79 (s, 2H), 3.77 (s, 3H), 1.36 (s, 9H).

$^{13}$C NMR: (100 MHz, CDCl$_3$) δ 160.3, 159.5, 155.0, 148.7, 142.4, 142.2, 139.7, 138.8, 138.4, 130.7, 129.9, 129.7, 129.1, 128.6, 128.10, 128.06, 127.6, 127.5, 127.28, 127.27, 126.7, 119.5, 112.6, 112.3, 103.7, 80.9, 70.5, 70.2, 55.6, 54.1, 28.5.

IR: (film) 1694, 1265, 1164, 1013, 738 cm$^{-1}$.

HRMS: (ESI+) m/z calc'd for (M+H)$^+$ [C$_{37}$H$_{36}$N$_2$O$_5$+H]$^+$: 589.2697, found 589.2698.

Example 19

Arylation Product 3ae:

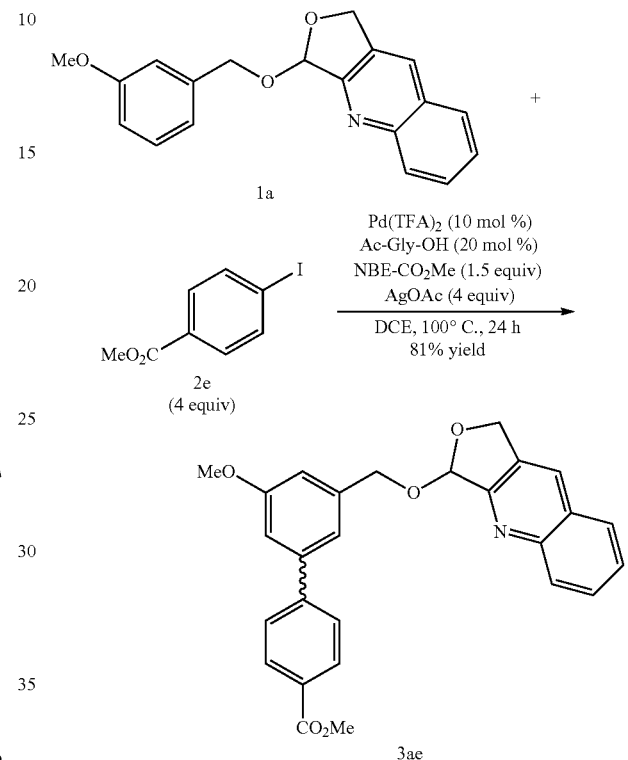

To a 2-dram vial with a PTFE-lined cap was charged with acetal 1a (1.00 mL, 0.100 M in DCE, 0.100 mmol), methyl 4-iodobenzoate (104 mg, 0.397 mmol), NBE-CO$_2$Me (22.0 mg, 0.145 mmol), Pd(TFA)$_2$ (3.3 mg, 0.00994 mmol), TFA-Gly-OH (3.4 mg, 0.0199 mmol), AgOAc (67.4 mg, 0.404 mmol), and DCE (1.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (3:1:1 hexanes/EtOAc/CH$_2$Cl$_2$ eluent) to afford arylation product 3ae (35.9 mg, 81% yield, R$_f$=0.18 in 3:1 hexanes/EtOAc) as a colorless oil. (9% recovery of starting material 1a was observed in the crude NMR prior to purification.)

$^1$H NMR: (400 MHz, CDCl$_3$) δ 8.17 (d, J=8.5 Hz, 1H), 8.08 (d, J=8.3 Hz, 2H), 8.05 (s, 1H), 7.83 (d, J=8.1 Hz, 1H), 7.77-7.70 (m, 1H), 7.65 (d, J=8.4 Hz, 2H), 7.61-7.54 (m, 1H), 7.30 (s, 1H), 7.06 (s, 2H), 6.34 (s, 1H), 5.42 (d, J=13.3 Hz, 1H), 5.24 (d, J=13.3 Hz, 1H), 4.98 (d, J=11.7 Hz, 1H), 4.91 (d, J=11.7 Hz, 1H), 3.93 (s, 3H), 3.87 (s, 3H).

$^{13}$C NMR: (100 MHz, CDCl$_3$) δ 167.2, 160.4, 159.5, 148.7, 145.6, 141.7, 140.1, 130.7, 130.2, 129.9, 129.7, 129.2, 129.1, 128.11, 128.06, 127.4, 127.3, 119.7, 113.2, 112.9, 103.8, 70.3, 70.2, 55.7, 52.3.

IR: (film) 1720, 1281, 1107, 1019, 731 cm$^{-1}$.
HRMS: (ESI+) m/z calc'd for (M+H)$^+$ [C$_{27}$H$_{23}$NO$_5$+H]$^+$: 442.1649, found 442.1652.

Example 20

Arylation Product 3af:

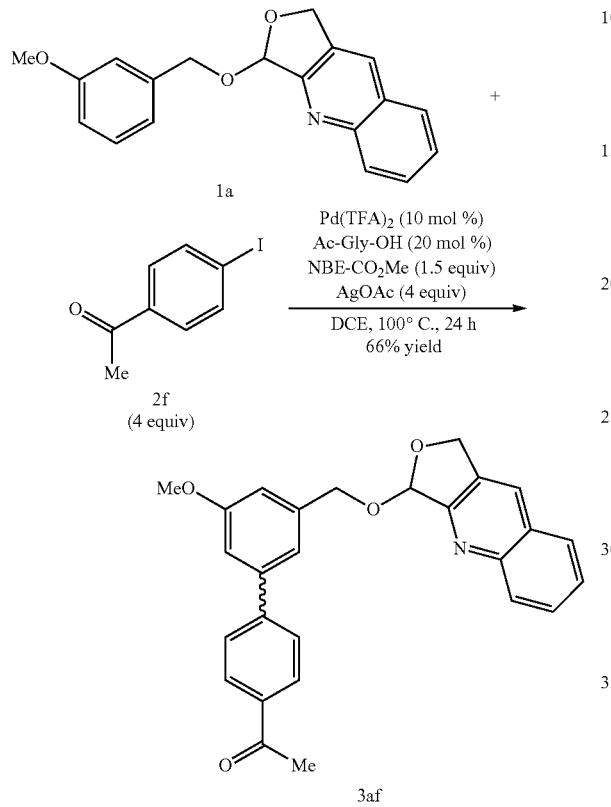

To a 2-dram vial with a PTFE-lined cap was charged with acetal 1a (1.00 mL, 0.100 M in DCE, 0.100 mmol), 1-(4-iodophenyl)ethanone (98.3 mg, 0.400 mmol), NBE-CO$_2$Me (21.7 mg, 0.143 mmol), Pd(TFA)$_2$ (3.4 mg, 0.0102 mmol), TFA-Gly-OH (3.4 mg, 0.0199 mmol), AgOAc (66.5 mg, 0.398 mmol), and DCE (1.00 mL). The resulting mixture was heated to 100° C. and stirred for 24 h. After cooling to room temperature, the mixture was filtered through a plug of silica gel, eluting with EtOAc (30 mL), and the filtrate was concentrated under reduced pressure. The residue was purified by flash column chromatography (2:1:1 hexanes/EtOAc/CH$_2$Cl$_2$ eluent) to afford arylation product 3af (28.0 mg, 66% yield, R$_f$=0.14 in 2:1 hexanes/EtOAc) as a light yellow oil. (16% recovery of starting material 1a was observed in the crude NMR prior to purification.)

$^1$H NMR: (400 MHz, CDCl$_3$) δ 8.17 (d, J=8.5 Hz, 1H), 8.06 (s, 1H), 8.01 (d, J=8.4 Hz, 2H), 7.84 (d, J=8.0 Hz, 1H), 7.77-7.71 (m, 1H), 7.68 (d, J=8.4 Hz, 2H), 7.61-7.55 (m, 1H), 7.30 (s, 1H), 7.06 (s, 2H), 6.35 (s, 1H), 5.42 (d, J=13.2 Hz, 1H), 5.25 (d, J=13.2 Hz, 1H), 4.98 (d, J=11.7 Hz, 1H), 4.92 (d, J=11.7 Hz, 1H), 3.87 (s, 3H), 2.63 (s, 3H).

$^{13}$C NMR: (100 MHz, CDCl$_3$) δ 198.0, 160.4, 159.5, 148.7, 145.7, 141.5, 140.1, 136.2, 130.7, 129.9, 129.8, 129.1, 129.0, 128.13, 128.07, 127.5, 127.3, 119.7, 113.2, 113.0, 103.8, 70.3, 70.2, 55.7, 26.9.

IR: (film) 1680, 1596, 1270, 1021, 732 cm$^{-1}$.
HRMS: (ESI+) m/z calc'd for (M+H)$^+$ [C$_{27}$H$_{23}$NO$_4$+H]$^+$: 426.1700, found 426.1703.

Example 21

Arylation Product 3ag:

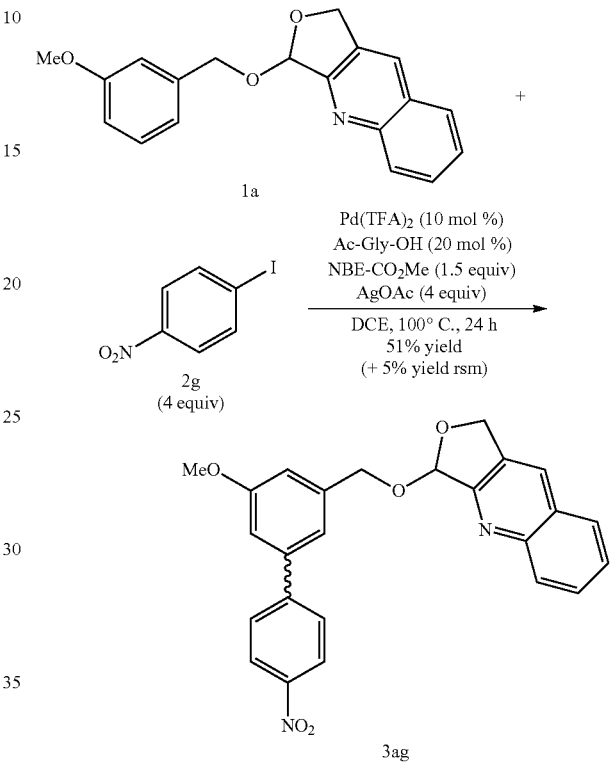

To a 2-dram vial with a PTFE-lined cap was charged with acetal 1a (1.00 mL, 0.100 M in DCE, 0.100 mmol), 1-iodo-4-nitrobenzene (99.2 mg, 0.398 mmol), NBE-CO$_2$Me (23.1 mg, 0.152 mmol), Pd(TFA)$_2$ (3.4 mg, 0.0102 mmol), TFA-Gly-OH (3.3 mg, 0.0193 mmol), AgOAc (67.8 mg, 0.406 mmol), and DCE (1.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (3:1:1 hexanes/EtOAc/CH$_2$Cl$_2$ eluent) to afford arylation product 3ag (23.5 mg, 51% yield+5% recovered 1a, R$_f$=0.18 in 2:1 hexanes/EtOAc) as a yellow oil. (41% recovery of starting material 1a was observed in the crude NMR prior to purification.)

$^1$H NMR: (400 MHz, CDCl$_3$) δ 8.27 (d, J=8.8 Hz, 2H), 8.17 (d, J=8.5 Hz, 1H), 8.07 (s, 1H), 7.85 (d, J=7.8 Hz, 1H), 7.77-7.69 (m, 3H), 7.63-7.55 (m, 1H), 7.31 (s, 1H), 7.08 (s, 1H), 7.06-7.04 (m, 1H), 6.35 (s, 1H), 5.43 (d, J=13.2 Hz, 1H), 5.26 (d, J=13.2 Hz, 1H), 4.99 (d, J=11.9 Hz, 1H), 4.92 (d, J=11.9 Hz, 1H), 3.88 (s, 3H).

$^{13}$C NMR: (100 MHz, CDCl$_3$) δ 160.5, 159.4, 148.7, 147.6, 147.4, 140.5, 140.4, 130.7, 129.9, 129.8, 129.2, 128.13, 128.11, 127.4, 124.2, 119.7, 113.7, 113.1, 103.8, 70.3, 70.2, 55.7.

IR: (film) 1593, 1517, 1346, 1022, 731 cm$^{-1}$.
HRMS: (ESI+) m/z calc'd for (M+H)$^+$ [C$_{25}$H$_{20}$N$_2$O$_5$+H]$^+$: 429.1445, found 429.1446.

Example 22

Arylation Product 3ah:

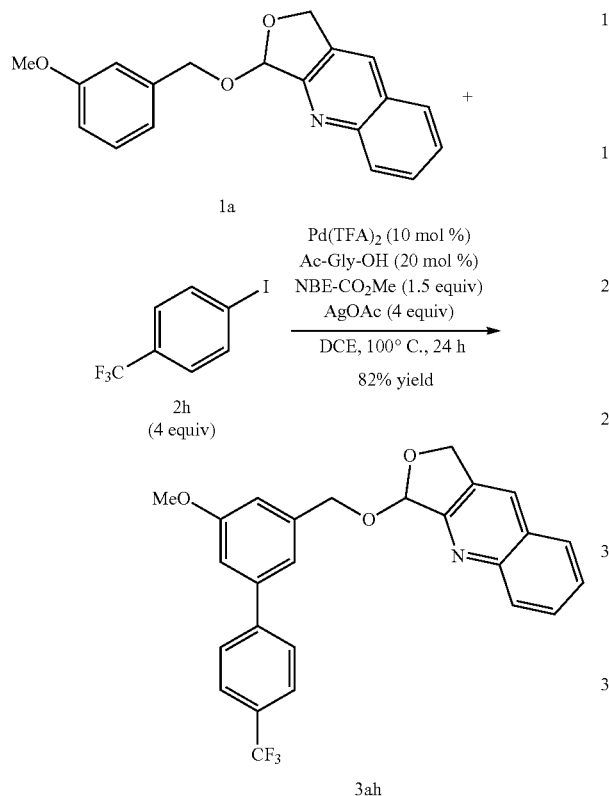

To a 2-dram vial with a PTFE-lined cap was charged with acetal 1a (1.00 mL, 0.100 M in DCE, 0.100 mmol), 1-iodo-4-(trifluoromethyl)benzene (110 mg, 0.404 mmol), NBE-CO$_2$Me (23.1 mg, 0.152 mmol), Pd(TFA)$_2$ (3.3 mg, 0.00994 mmol), TFA-Gly-OH (3.4 mg, 0.0199 mmol), AgOAc (66.5 mg, 0.398 mmol), and DCE (1.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (5:1:1 hexanes/EtOAc/CH$_2$Cl$_2$ eluent) to afford arylation product 3ah (36.8 mg, 82% yield, R$_f$=0.32 in 2:1 hexanes/EtOAc) as a light yellow oil.

$^1$H NMR: (400 MHz, CDCl$_3$) δ 8.18 (d, J=8.5 Hz, 1H), 8.05 (s, 1H), 7.84 (d, J=8.1 Hz, 1H), 7.76-7.63 (m, 5H), 7.61-7.53 (m, 1H), 7.28 (s, 1H), 7.06 (s, 1H), 7.05-7.01 (m, 1H), 6.35 (s, 1H), 5.42 (d, J=13.2 Hz, 1H), 5.24 (d, J=13.2 Hz, 1H), 4.99 (d, J=11.7 Hz, 1H), 4.92 (d, J=11.7 Hz, 1H), 3.87 (s, 3H).

$^{13}$C NMR: (100 MHz, CDCl$_3$) δ 160.4, 159.4, 148.7, 144.7, 141.4, 140.2, 130.7, 129.9, 129.8, 129.1, 128.12, 128.07, 127.7, 127.3, 125.8 (q, J=3.6 Hz), 119.7, 113.1, 113.0, 103.8, 70.3, 70.2, 55.7.

$^{19}$F NMR: (376 MHz, CDCl$_3$) δ −62.4.
IR: (film) 1326, 1166, 1123, 1068, 1018 cm$^{-1}$.
HRMS: (ESI+) m/z calc'd for (M+H)$^+$ [C$_{26}$H$_{20}$F$_3$NO$_3$+H]$^+$: 452.1468, found 452.1469.

Example 23

Arylation Product 3ai:

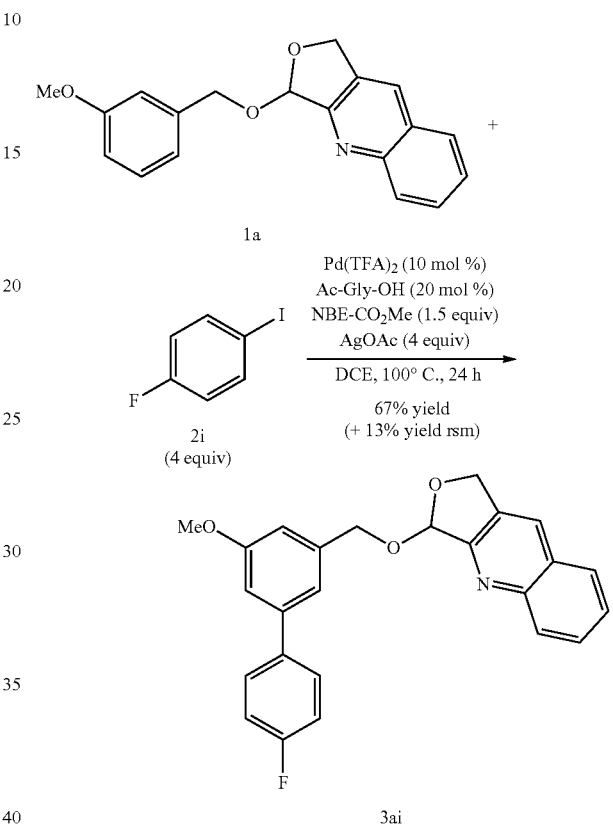

To a 2-dram vial with a PTFE-lined cap was charged with acetal 1a (1.00 mL, 0.100 M in DCE, 0.100 mmol), 1-fluoro-4-iodobenzene (89.1 mg, 0.401 mmol), NBE-CO$_2$Me (23.7 mg, 0.156 mmol), Pd(TFA)$_2$ (3.4 mg, 0.0102 mmol), TFA-Gly-OH (3.5 mg, 0.0205 mmol), AgOAc (66.4 mg, 0.398 mmol), and DCE (1.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (5:1:1 hexanes/EtOAc/CH$_2$Cl$_2$ eluent) to afford arylation product 3ai (30.7 mg, 67% yield+13% recovered 1a, R$_f$=0.31 in 2:1 hexanes/EtOAc) as a light yellow oil. (13% recovery of starting material 1a was observed in the crude NMR prior to purification.)

$^1$H NMR: (400 MHz, CDCl$_3$) δ 8.18 (d, J=8.5 Hz, 1H), 8.05 (s, 1H), 7.84 (d, J=8.1 Hz, 1H), 7.78-7.68 (m, 1H), 7.64-7.50 (m, 3H), 7.22 (s, 1H), 7.10 (app. t, J=8.7 Hz, 2H), 7.02-6.97 (m, 2H), 6.34 (s, 1H), 5.42 (d, J=13.2 Hz, 1H), 5.24 (d, J=13.2 Hz, 1H), 4.97 (d, J=11.7 Hz, 1H), 4.91 (d, J=11.7 Hz, 1H), 3.86 (s, 3H).

$^{13}$C NMR: (100 MHz, CDCl$_3$) δ 162.7 (d, J=246.4 Hz), 160.3, 159.5, 148.7, 141.9, 139.9, 137.3 (d, J=3.0 Hz), 130.7, 129.9, 129.7, 129.1, 129.0 (d, J=8.0 Hz), 128.12, 128.06, 127.3, 119.5, 115.7 (d, J=21.4 Hz), 112.7, 112.3, 103.7, 70.4, 70.2, 55.6.

$^{19}$F NMR: (376 MHz, CDCl$_3$) δ −115.5.

IR: (film) 1601, 1513, 1215, 1022, 832 cm$^{-1}$.

HRMS: (ESI+) m/z calc'd for (M+H)$^+$ [C$_{25}$H$_{20}$FNO$_3$+H]$^+$: 402.1500, found 402.1501.

Example 24

Arylation Product 3aj:

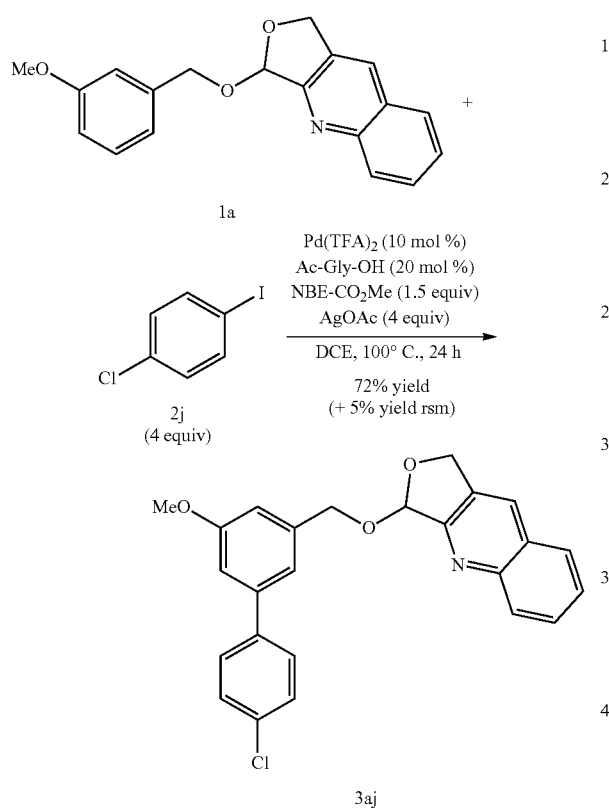

To a 2-dram vial with a PTFE-lined cap was charged with acetal 1a (1.00 mL, 0.100 M in DCE, 0.100 mmol), 1-chloro-4-iodobenzene (96.8 mg, 0.407 mmol), NBE-CO$_2$Me (23.3 mg, 0.153 mmol), Pd(TFA)$_2$ (3.3 mg, 0.00994 mmol), TFA-Gly-OH (3.4 mg, 0.0199 mmol), AgOAc (65.7 mg, 0.393 mmol), and DCE (1.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (5:1:1 hexanes/EtOAc/CH$_2$Cl$_2$ eluent) to afford arylation product 3aj (31.7 mg, 72% yield+5% recovered 1a, R$_f$=0.29 in 2:1 hexanes/EtOAc) as a light yellow oil. (5% recovery of starting material 1a was observed in the crude NMR prior to purification.)

$^1$H NMR: (400 MHz, CDCl$_3$) δ 8.18 (d, J=8.5 Hz, 1H), 8.04 (s, 1H), 7.83 (d, J=8.1 Hz, 1H), 7.73 (ddd, J=8.4, 7.0, 1.3 Hz, 1H), 7.61-7.54 (m, 1H), 7.51 (d, J=8.5 Hz, 2H), 7.38 (d, J=8.5 Hz, 2H), 7.23 (s, 1H), 7.02 (s, 1H), 7.01-6.97 (m, 1H), 6.34 (s, 1H), 5.41 (d, J=13.2 Hz, 1H), 5.24 (d, J=13.2 Hz, 1H), 4.97 (d, J=11.7 Hz, 1H), 4.91 (d, J=11.7 Hz, 1H), 3.86 (s, 3H).

$^{13}$C NMR: (100 MHz, CDCl$_3$) δ 160.4, 159.5, 148.7, 141.6, 140.0, 139.6, 133.7, 130.7, 129.9, 129.7, 129.1, 129.0, 128.7, 128.11, 128.06, 127.3, 119.4, 112.7, 112.6, 103.7, 70.4, 70.2, 55.6.

IR: (film) 1597, 1459, 1013, 825, 732 cm$^{-1}$.

HRMS: (ESI+) m/z calc'd for (M+H)$^+$ [C$_{25}$H$_{20}$ClNO$_3$+H]$^+$: 418.1204, found 418.1207.

Example 25

Arylation Product 3ak:

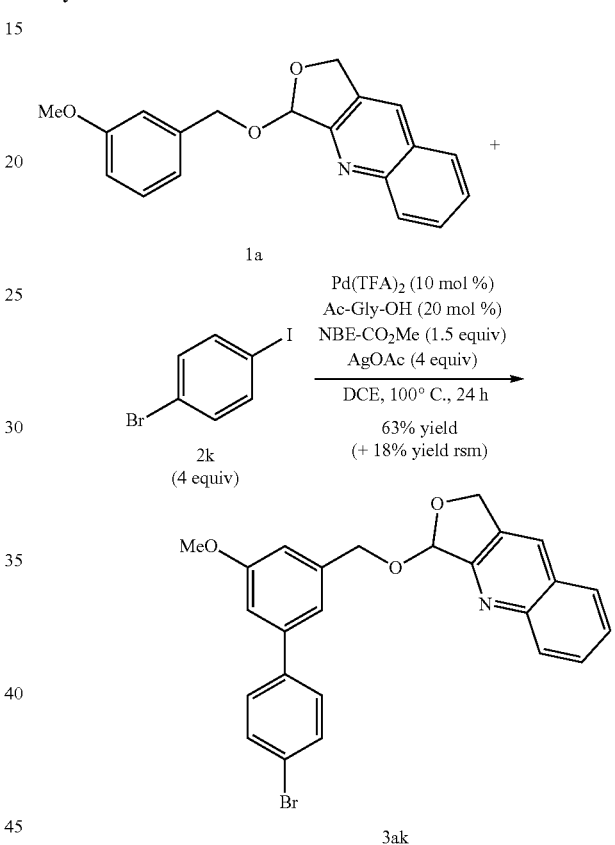

To a 2-dram vial with a PTFE-lined cap was charged with acetal 1a (1.00 mL, 0.100 M in DCE, 0.100 mmol), 1-bromo-4-iodobenzene (113 mg, 0.399 mmol), NBE-CO$_2$Me (21.5 mg, 0.141 mmol), Pd(TFA)$_2$ (3.4 mg, 0.0102 mmol), TFA-Gly-OH (3.4 mg, 0.0199 mmol), AgOAc (66.1 mg, 0.396 mmol), and DCE (1.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30.0 mL), and the filtrate was concentrated under reduced pressure. The residue was purified by flash column chromatography (5:1:1 hexanes/EtOAc/CH$_2$Cl$_2$ eluent) to afford arylation product 3ak (34.6 mg, 63% yield+18% recovered 1a, R$_f$=0.28 in 2:1 hexanes/EtOAc) as a light yellow oil. (19% recovery of starting material 1a was observed in the crude NMR prior to purification.)

$^1$H NMR: (400 MHz, CDCl$_3$) δ 8.18 (d, J=8.5 Hz, 1H), 8.05 (s, 1H), 7.83 (d, J=8.1 Hz, 1H), 7.73 (ddd, J=8.3, 6.9, 1.3 Hz, 1H), 7.63-7.50 (m, 3H), 7.45 (d, J=8.5 Hz, 2H), 7.23 (s, 1H), 7.05-7.01 (m, 1H), 7.01-6.97 (m, 1H), 6.34 (s, 1H), 5.41 (d, J=13.2 Hz, 1H), 5.24 (d, J=13.2 Hz, 1H), 4.97 (d, J=11.7 Hz, 1H), 4.91 (d, J=11.7 Hz, 1H), 3.86 (s, 3H).

$^{13}C$ NMR: (100 MHz, CDCl$_3$) δ 160.4, 159.5, 148.7, 141.7, 140.1, 140.0, 132.0, 130.7, 129.9, 129.7, 129.1, 129.0, 128.11, 128.06, 127.3, 121.8, 119.4, 112.6, 103.7, 70.3, 70.2, 55.6.

IR: (film) 1596, 1072, 1021, 1009, 822 cm$^{-1}$.

HRMS: (ESI+) m/z calc'd for (M+H)$^+$ [C$_{25}$H$_{20}$BrNO$_3$+H]$^+$: 462.0699, found 462.0701.

Example 26

Arylation Product 3al:

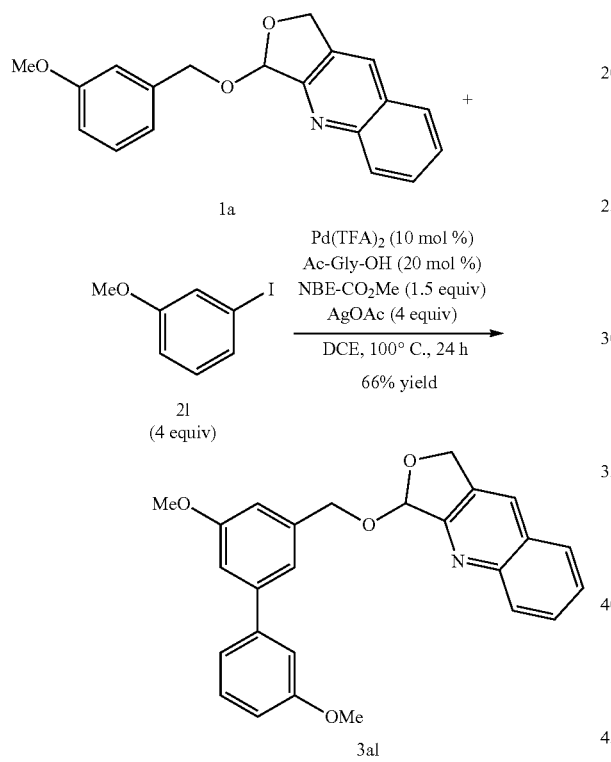

To a 2-dram vial with a PTFE-lined cap was charged with acetal 1a (1.00 mL, 0.100 M in DCE, 0.100 mmol), 1-iodo-3-methoxybenzene (94.8 mg, 0.405 mmol), NBE-CO$_2$Me (22.7 mg, 0.149 mmol), Pd(TFA)$_2$ (3.3 mg, 0.00994 mmol), TFA-Gly-OH (3.3 mg, 0.0193 mmol), AgOAc (67.4 mg, 0.404 mmol), and DCE (1.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (5:1:1 hexanes/EtOAc/CH$_2$Cl$_2$ eluent) to afford arylation product 3al (27.1 mg, 66% yield, R$_f$=0.24 in 2:1 hexanes/EtOAc) as a colorless oil. (16% recovery of starting material 1a was observed in the crude NMR prior to purification.)

$^1$H NMR: (400 MHz, CDCl$_3$) δ 8.18 (d, J=8.5 Hz, 1H), 8.05 (s, 1H), 7.84 (d, J=8.1 Hz, 1H), 7.77-7.68 (m, 1H), 7.61-7.53 (m, 1H), 7.33 (t, J=7.9 Hz, 1H), 7.26 (s, 1H), 7.18

(d, J=8.0 Hz, 1H), 7.15-7.10 (m, 1H), 7.07-6.99 (m, 2H), 6.93-6.86 (m, 1H), 6.35 (s, 1H), 5.42 (d, J=13.2 Hz, 1H), 5.24 (d, J=13.2 Hz, 1H), 4.98 (d, J=11.6 Hz, 1H), 4.91 (d, J=11.6 Hz, 1H), 3.87 (s, 3H), 3.85 (s, 3H).

$^{13}$C NMR: (100 MHz, CDCl$_3$) δ 160.3, 160.1, 159.6, 148.7, 142.8, 142.7, 139.7, 130.7, 130.0, 129.9, 129.7, 129.1, 128.11, 128.05, 127.3, 120.0, 119.7, 113.11, 113.10, 112.9, 112.5, 103.7, 70.5, 70.2, 55.6, 55.5.

IR: (film) 1596, 1579, 1462, 1243, 1022 cm$^{-1}$.

HRMS: (ESI+) m/z calc'd for (M+H)$^+$ [C$_{26}$H$_{23}$NO$_4$+H]$^+$: 414.1700, found 414.1700.

Example 27

Arylation Product 3am:

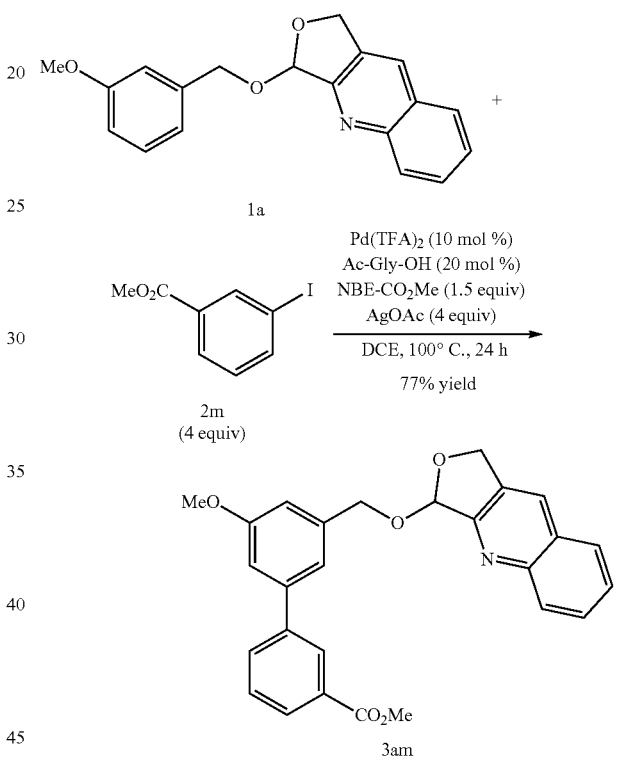

To a 2-dram vial with a PTFE-lined cap was charged with acetal 1a (1.00 mL, 0.100 M in DCE, 0.100 mmol), methyl 3-iodobenzoate (105 mg, 0.401 mmol), NBE-CO$_2$Me (22.6 mg, 0.149 mmol), Pd(TFA)$_2$ (3.4 mg, 0.0102 mmol), TFA-Gly-OH (3.3 mg, 0.0193 mmol), AgOAc (65.8 mg, 0.394 mmol), and DCE (1.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (4:1:1 hexanes/EtOAc/CH$_2$Cl$_2$ eluent) to afford arylation product 3am (34.0 mg, 77% yield, R$_f$=0.18 in 2:1 hexanes/EtOAc) as a colorless oil. (10% recovery of starting material 1a was observed in the crude NMR prior to purification.)

$^1$H NMR: (400 MHz, CDCl$_3$) δ 8.26 (s, 1H), 8.17 (d, J=8.5 Hz, 1H), 8.05 (s, 1H), 8.01 (d, J=7.8 Hz, 1H), 7.84 (d, J=8.0 Hz, 1H), 7.78 (d, J=7.8 Hz, 1H), 7.75-7.68 (m, 1H), 7.61-7.54 (m, 1H), 7.49 (t, J=7.7 Hz, 1H), 7.29 (s, 1H), 7.10-7.01 (m, 2H), 6.35 (s, 1H), 5.42 (d, J=13.3 Hz, 1H), 5.24 (d, J=13.3 Hz, 1H), 4.98 (d, J=11.7 Hz, 1H), 4.92 (d, J=11.7 Hz, 1H), 3.94 (s, 3H), 3.88 (s, 3H).

$^{13}$C NMR: (100 MHz, CDCl$_3$) δ 167.2, 160.4, 159.5, 148.7, 141.8, 141.4, 140.0, 131.9, 130.8, 130.7, 130.0, 129.7, 129.1, 129.0, 128.7, 128.5, 128.13, 128.06, 127.3, 119.6, 112.85, 112.82, 103.8, 70.4, 70.2, 55.7, 52.4.

IR: (film) 1721, 1270, 1212, 1022, 731 cm$^{-1}$.

HRMS: (ESI+) m/z calc'd for (M+H)$^+$ [C$_{27}$H$_{23}$NO$_5$+H]$^+$: 442.1649, found 442.1652.

Example 28

Arylation Product 3an:

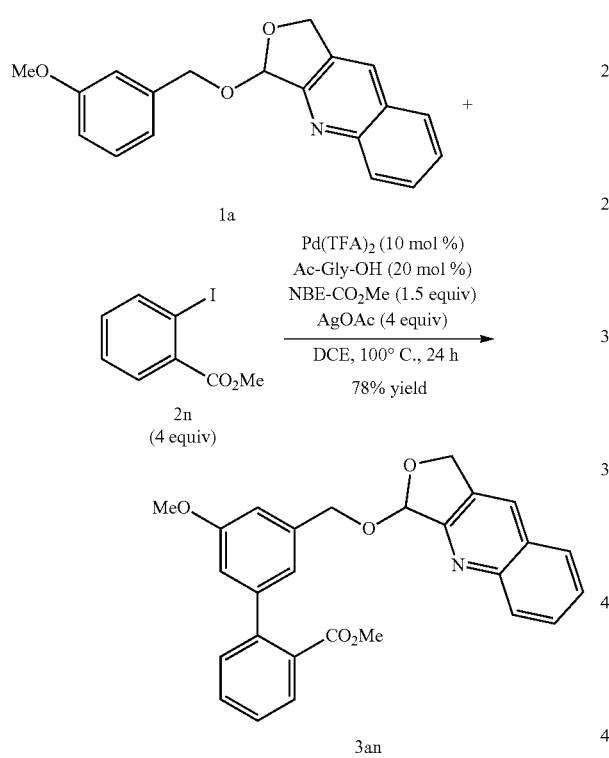

To a 2-dram vial with a PTFE-lined cap was charged with acetal 1a (1.00 mL, 0.100 M in DCE, 0.100 mmol), methyl 2-iodobenzoate (104 mg, 0.397 mmol), NBE-CO$_2$Me (22.1 mg, 0.145 mmol), Pd(TFA)$_2$ (3.4 mg, 0.0102 mmol), TFA-Gly-OH (3.4 mg, 0.0199 mmol), AgOAc (66.4 mg, 0.398 mmol), and DCE (1.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (4:1:1 hexanes/EtOAc/CH$_2$Cl$_2$ eluent) to afford arylation product 3an (34.2 mg, 78% yield, R$_f$=0.18 in 2:1 hexanes/EtOAc) as a colorless oil.

$^1$H NMR: (400 MHz, CDCl$_3$) δ 8.16 (d, J=8.5 Hz, 1H), 8.05 (s, 1H), 7.83 (d, J=8.1 Hz, 1H), 7.81-7.75 (m, 1H), 7.75-7.68 (m, 1H), 7.60-7.54 (m, 1H), 7.53-7.47 (m, 1H), 7.42-7.35 (m, 2H), 7.03 (s, 1H), 6.97 (s, 1H), 6.83-6.75 (m, 1H), 6.32 (s, 1H), 5.41 (d, J=13.2 Hz, 1H), 5.23 (d, J=13.2 Hz, 1H), 4.95 (d, J=11.6 Hz, 1H), 4.87 (d, J=11.6 Hz, 1H), 3.83 (s, 3H), 3.60 (s, 3H).

$^{13}$C NMR: (100 MHz, CDCl$_3$) δ 169.4, 159.7, 159.6, 148.7, 142.8, 142.2, 139.1, 131.3, 131.2, 130.81, 130.78, 129.9, 129.8, 129.7, 129.1, 128.09, 128.05, 127.4, 127.3, 120.9, 113.8, 112.6, 103.6, 70.3, 70.1, 55.6, 52.2.

IR: (film) 1724, 1293, 1022, 910, 732 cm$^{-1}$.

HRMS: (ESI+) m/z calc'd for (M+H)$^+$ [C$_{27}$H$_{23}$NO$_5$+H]$^+$: 442.1649, found 442.1652.

Example 29

Arylation Product 3aa:

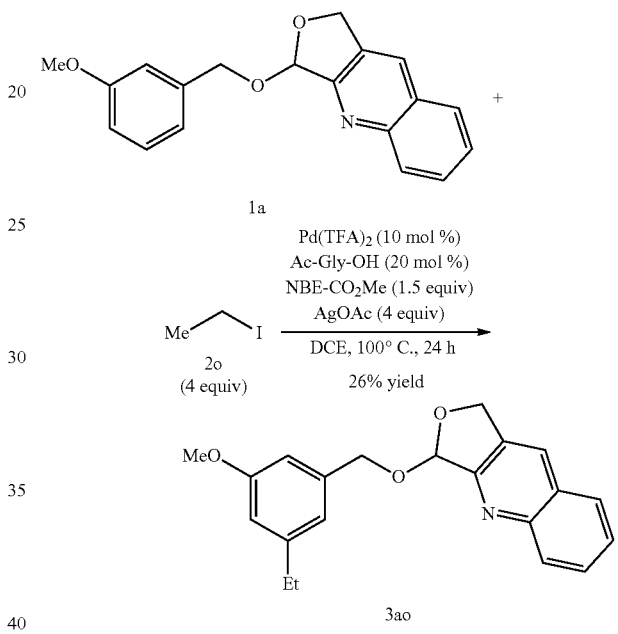

To a 2-dram vial with a PTFE-lined cap was charged with acetal 1a (15.7 mg, 0.0511 mmol), iodoethane (32.2 mg, 0.206 mmol), NBE-CO$_2$Me (12.3 mg, 0.0809 mmol), Pd(TFA)$_2$ (1.8 mg, 0.00542 mmol), TFA-Gly-OH (1.8 mg, 0.0105 mmol), AgOAc (33.9 mg, 0.203 mmol), and DCE (1.00 mL). The resulting mixture was heated to 100° C. and stirred for 24 h. After cooling to room temperature, the mixture was filtered through a plug of silica gel, eluting with EtOAc (30 mL), and the filtrate was concentrated under reduced pressure. The residue was purified by preparative TLC (2:1 hexanes/EtOAc eluent) to afford the alkylation product 3ao (4.4 mg, 26% yield, R$_f$=0.40 in 2:1 hexanes/EtOAc) as yellow oil. (59% recovery of starting material 1a was observed in the crude NMR prior to purification.)

$^1$H NMR: (400 MHz, CDCl$_3$) δ 8.18 (d, J=8.5 Hz, 1H), 8.06 (s, 1H), 7.84 (d, J=8.0 Hz, 1H), 7.73 (app. t, J=7.7 Hz, 1H), 7.58 (app. t, J=7.5 Hz, 1H), 6.88 (s, 1H), 6.85 (s, 1H), 6.67 (s, 1H), 6.31 (s, 1H), 5.42 (d, J=13.3 Hz, 1H), 5.24 (d, J=13.3 Hz, 1H), 4.90 (d, J=11.4 Hz, 1H), 4.83 (d, J=11.4 Hz, 1H), 3.80 (s, 3H), 2.61 (q, J=7.6 Hz, 2H), 1.22 (t, J=7.6 Hz, 3H).

$^{13}$C NMR: (100 MHz, CDCl$_3$) δ 160.0, 159.7, 148.7, 146.1, 139.1, 130.8, 130.0, 129.7, 129.1, 128.11, 128.06, 127.3, 120.5, 113.6, 110.7, 103.6, 70.6, 70.1, 55.5, 29.1, 15.7.

IR: (film) 1596, 1462, 1290, 1074, 1022 cm$^{-1}$.

HRMS: (ESI+) m/z calc'd for (M+H)$^{+}$ [C$_{21}$H$_{12}$NO$_{3}$+H]$^{+}$: 336.1594, found 336.1597.

Example 30

Arylation Product 3bn:

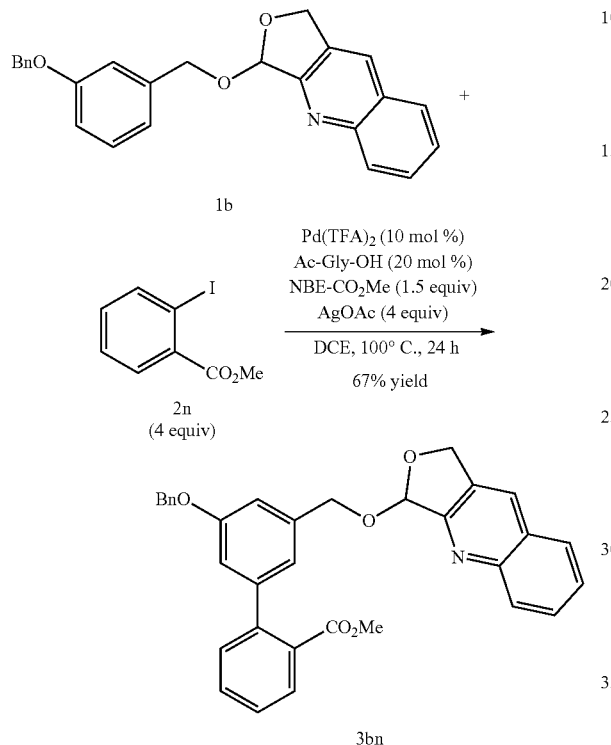

To a 2-dram vial with a PTFE-lined cap was charged with acetal 1b (1.00 mL, 0.100 M in DCE, 0.100 mmol), methyl 2-iodobenzoate (107 mg, 0.408 mmol), NBE-CO$_{2}$Me (21.9 mg, 0.144 mmol), Pd(TFA)$_{2}$ (3.4 mg, 0.0102 mmol), TFA-Gly-OH (3.4 mg, 0.0199 mmol), AgOAc (68.8 mg, 0.412 mmol), and DCE (1.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (5:1:1 hexanes/EtOAc/CH$_{2}$Cl$_{2}$ eluent) to afford arylation product 3bn (34.7 mg, 67% yield, R$_f$=0.20 in 2:1 hexanes/EtOAc) as a light yellow oil.

$^{1}$H NMR: (400 MHz, CDCl$_{3}$) δ 8.17 (d, J=8.5 Hz, 1H), 8.05 (s, 1H), 7.84 (d, J=8.1 Hz, 1H), 7.80-7.76 (m, 1H), 7.75-7.68 (m, 1H), 7.57 (app. t, J=7.4 Hz, 1H), 7.50 (app. td, J=7.5, 1.2 Hz, 1H), 7.44 (d, J=7.2 Hz, 2H), 7.42-7.34 (m, 4H), 7.34-7.28 (m, 1H), 7.13 (s, 1H), 6.99 (s, 1H), 6.88 (s, 1H), 6.33 (s, 1H), 5.40 (d, J=13.3 Hz, 1H), 5.22 (d, J=13.3 Hz, 1H), 5.09 (s, 2H), 4.96 (d, J=11.6 Hz, 1H), 4.88 (d, J=11.6 Hz, 1H), 3.58 (s, 3H).

$^{13}$C NMR: (100 MHz, CDCl$_{3}$) δ 169.4, 159.6, 158.9, 148.6, 142.8, 142.1, 139.2, 137.1, 131.3, 131.2, 130.82, 130.75, 129.9, 129.8, 129.7, 129.1, 128.7, 128.12, 128.07, 128.05, 127.8, 127.4, 127.3, 121.1, 114.6, 113.4, 103.6, 70.3, 70.2, 70.1, 52.2.

IR: (film) 1725, 1593, 1293, 1253, 1021 cm$^{-1}$.

HRMS: (ESI+) m/z calc'd for (M+H)$^{+}$ [C$_{33}$H$_{27}$NO$_{5}$+H]$^{+}$: 518.1962, found 518.1969.

Example 31

Arylation Product 3bn:

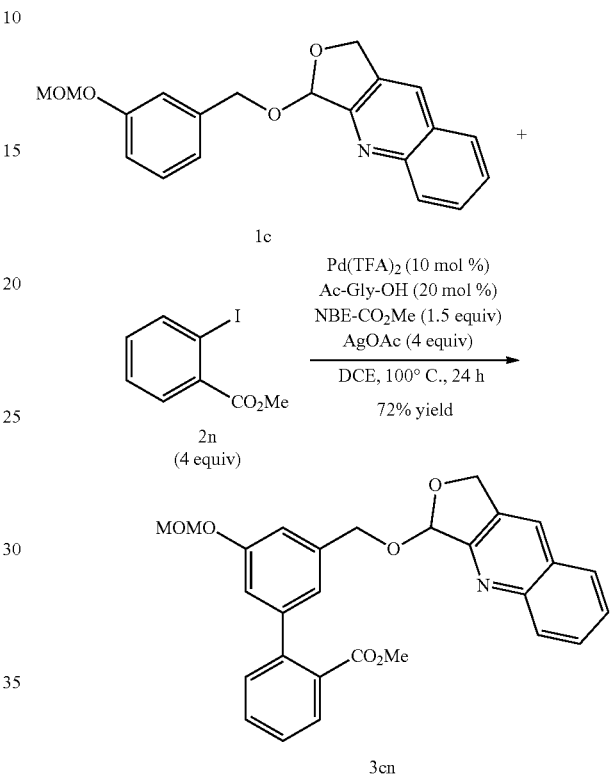

To a 2-dram vial with a PTFE-lined cap was charged with acetal 1c (1.00 mL, 0.100 M in DCE, 0.100 mmol), methyl 2-iodobenzoate (106 mg, 0.405 mmol), NBE-CO$_{2}$Me (22.4 mg, 0.147 mmol), Pd(TFA)$_{2}$ (3.3 mg, 0.00994 mmol), TFA-Gly-OH (3.3 mg, 0.0193 mmol), AgOAc (66.6 mg, 0.399 mmol), and DCE (1.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (2:1 hexanes/EtOAc eluent) to afford arylation product 3cn (34.0 mg, 72% yield, R$_f$=0.19 in 2:1 hexanes/EtOAc) as a light yellow oil.

$^{1}$H NMR: (400 MHz, CDCl$_{3}$) δ 8.16 (d, J=8.5 Hz, 1H), 8.04 (s, 1H), 7.83 (d, J=8.1 Hz, 1H), 7.80-7.75 (m, 1H), 7.71 (app. t, J=7.3 Hz, 1H), 7.56 (app. t, J=7.4 Hz, 1H), 7.52-7.46 (m, 1H), 7.42-7.35 (m, 2H), 7.13 (s, 1H), 7.05 (s, 1H), 6.92 (s, 1H), 6.32 (s, 1H), 5.41 (d, J=13.4 Hz, 1H), 5.22 (d, J=13.4 Hz, 1H), 5.18 (s, 2H), 4.95 (d, J=11.5 Hz, 1H), 4.86 (d, J=11.5 Hz, 1H), 3.60 (s, 3H), 3.47 (s, 3H).

$^{13}$C NMR: (100 MHz, CDCl$_{3}$) δ 169.4, 159.5, 157.2, 148.6, 142.7, 141.9, 139.2, 131.3, 131.2, 130.83, 130.75, 129.9, 129.8, 129.6, 129.1, 128.1, 128.0, 127.4, 127.2, 122.0, 115.9, 115.1, 103.4, 94.7, 70.2, 70.1, 56.2, 52.2.

IR: (film) 1727, 1594, 1292, 1151, 1010 cm$^{-1}$.

HRMS: (ESI+) m/z calc'd for (M+H)$^+$ [C$_{28}$H$_{25}$NO$_6$+H]$^+$: 472.1755, found 472.1760.

Example 32

Arylation Product 3bp:

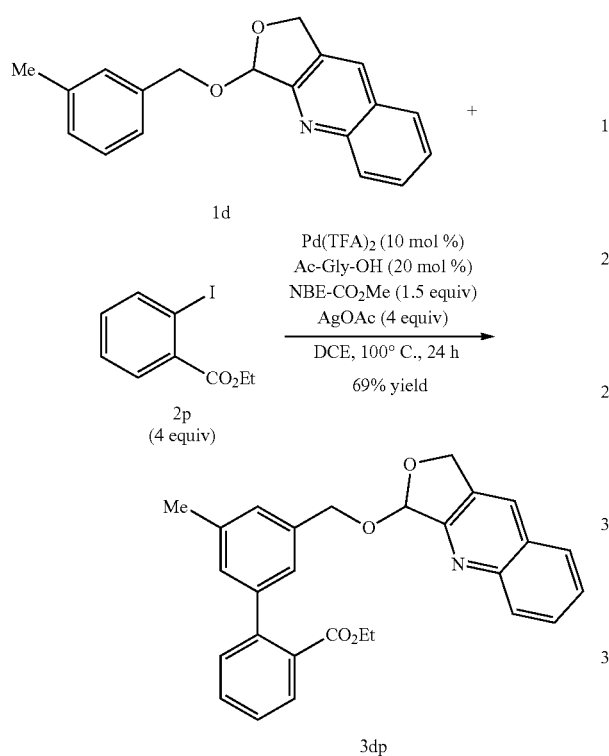

3dp

To a 2-dram vial with a PTFE-lined cap was charged with acetal 1d (29.4 mg, 0.101 mmol), ethyl 2-iodobenzoate (110 mg, 0.399 mmol), NBE-CO$_2$Me (22.6 mg, 0.149 mmol), Pd(TFA)$_2$ (3.3 mg, 0.00994 mmol), TFA-Gly-OH (3.3 mg, 0.0193 mmol), AgOAc (66.5 mg, 0.398 mmol), and DCE (2.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (4:1 hexanes/EtOAc eluent) to afford arylation product 3dp (30.8 mg, 69% yield, R$_f$=0.33 in 2:1 hexanes/EtOAc) as a light yellow oil.

$^1$H NMR: (400 MHz, CDCl$_3$) δ 8.17 (d, J=8.5 Hz, 1H), 8.04 (s, 1H), 7.83 (d, J=8.1 Hz, 1H), 7.81-7.75 (m, 1H), 7.75-7.68 (m, 1H), 7.60-7.53 (m, 1H), 7.48 (td, J=7.5, 1.3 Hz, 1H), 7.41-7.33 (m, 2H), 7.27 (s, 1H), 7.19 (s, 1H), 7.05 (s, 1H), 6.32 (s, 1H), 5.40 (d, J=13.3 Hz, 1H), 5.23 (d, J=13.3 Hz, 1H), 4.95 (d, J=11.3 Hz, 1H), 4.85 (d, J=11.3 Hz, 1H), 4.05 (q, J=7.1 Hz, 2H), 2.36 (s, 3H), 0.96 (t, J=7.1 Hz, 3H).

$^{13}$C NMR: (100 MHz, CDCl$_3$) δ 169.2, 159.6, 148.6, 142.4, 141.5, 137.9, 137.5, 131.6, 131.2, 130.80, 130.78, 129.9, 129.7, 129.6, 129.1, 128.8, 128.1, 128.03, 128.01, 127.23, 127.21, 125.7, 103.6, 70.4, 70.1, 61.1, 21.5, 13.9.

IR: (film) 1716, 1290, 1248, 1022, 761 cm$^{-1}$.

HRMS: (ESI+) m/z calc'd for (M+H)$^+$ [C$_{28}$H$_{25}$NO$_4$+H]$^+$: 440.1856, found 440.1863.

Example 33

Arylation Product 3ep:

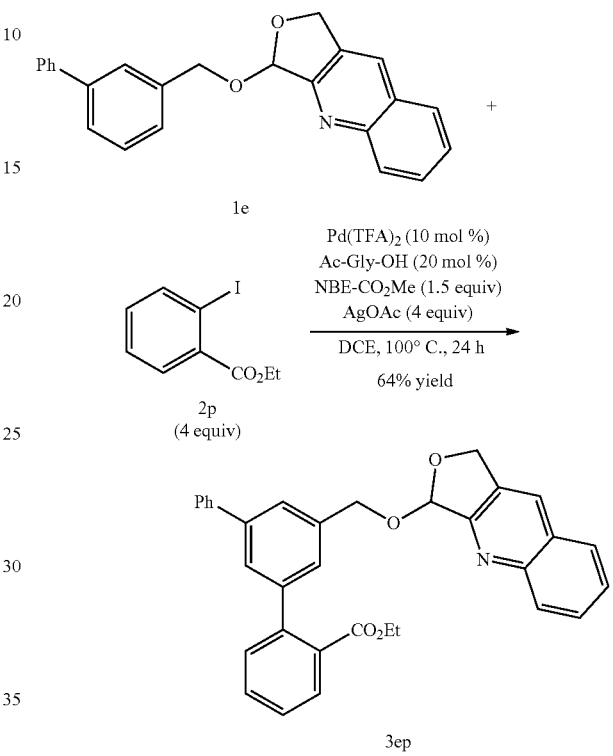

3ep

To a 2-dram vial with a PTFE-lined cap was charged with acetal 1e (1.00 mL, 0.100 M in DCE, 0.100 mmol), ethyl 2-iodobenzoate (110 mg, 0.399 mmol), NBE-CO$_2$Me (22.9 mg, 0.151 mmol), Pd(TFA)$_2$ (3.4 mg, 0.0102 mmol), TFA-Gly-OH (3.4 mg, 0.0199 mmol), AgOAc (67.5 mg, 0.404 mmol), and DCE (1.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (3:1 hexanes/EtOAc eluent) to afford arylation product 3ep (32.3 mg, 64% yield, R$_f$=0.23 in 2:1 hexanes/EtOAc) as a light yellow oil. (7% recovery of starting material 1e was observed in the crude NMR prior to purification.)

$^1$H NMR: (500 MHz, CDCl$_3$) δ 8.18 (d, J=8.5 Hz, 1H), 8.05 (s, 1H), 7.84 (d, J=7.8 Hz, 2H), 7.76-7.68 (m, 2H), 7.63 (d, J=7.3 Hz, 2H), 7.57 (app. t, J=7.5 Hz, 1H), 7.52 (app. t, J=7.5 Hz, 1H), 7.47 (s, 1H), 7.46-7.40 (m, 4H), 7.39 (s, 1H), 7.34 (app. t, J=7.4 Hz, 1H), 6.37 (s, 1H), 5.42 (d, J=13.2 Hz, 1H), 5.24 (d, J=13.2 Hz, 1H), 5.05 (d, J=11.5 Hz, 1H), 4.97 (d, J=11.5 Hz, 1H), 4.04 (q, J=7.1 Hz, 2H), 0.91 (t, J=7.1 Hz, 3H).

$^{13}$C NMR: (100 MHz, CDCl$_3$) δ 169.0, 159.6, 148.6, 142.3, 142.2, 141.2, 141.0, 138.2, 131.6, 131.3, 130.9, 130.7, 129.9, 129.7, 129.1, 128.08, 128.05, 127.6, 127.5, 127.4, 127.33, 127.27, 126.9, 125.9, 103.8, 70.4, 70.1, 61.1, 13.8.

IR: (film) 1716, 1291, 1252, 1022, 758 cm$^{-1}$.
HRMS: (ESI+) m/z calc'd for (M+H)$^+$ [C$_{33}$H$_{27}$NO$_4$+H]$^+$: 502.2013, found 502.2017.

Example 34

Arylation Product 3fp:

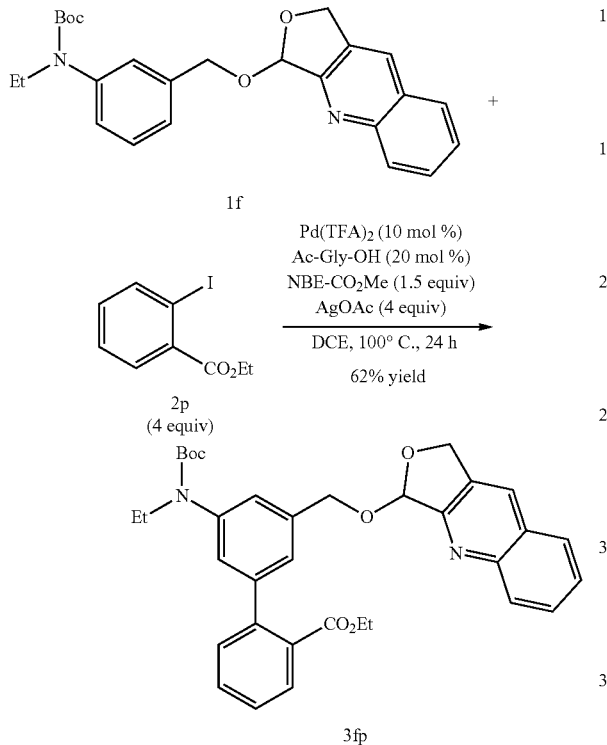

To a 2-dram vial with a PTFE-lined cap was charged with acetal 1f (1.00 mL, 0.100 M in DCE, 0.100 mmol), ethyl 2-iodobenzoate (111 mg, 0.402 mmol), NBE-CO$_2$Me (23.8 mg, 0.157 mmol), Pd(TFA)$_2$ (3.4 mg, 0.0102 mmol), TFA-Gly-OH (3.4 mg, 0.0199 mmol), AgOAc (66.3 mg, 0.397 mmol), and DCE (1.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (3:1 hexanes/EtOAc eluent) to afford arylation product 3fp (35.4 mg, 62% yield, R$_f$=0.16 in 2:1 hexanes/EtOAc) as a colorless oil.

$^1$H NMR: (500 MHz, CDCl$_3$) δ 8.16 (d, J=8.5 Hz, 1H), 8.05 (s, 1H), 7.84 (d, J=8.2 Hz, 1H), 7.79 (d, J=7.7 Hz, 1H), 7.75-7.68 (m, 1H), 7.59-7.54 (m, 1H), 7.49 (app. td, J=7.5, 1.2 Hz, 1H), 7.42-7.33 (m, 2H), 7.28 (s, 1H), 7.20 (s, 1H), 7.07 (s, 1H), 6.32 (s, 1H), 5.40 (d, J=13.2 Hz, 1H), 5.23 (d, J=13.2 Hz, 1H), 4.96 (d, J=11.6 Hz, 1H), 4.86 (d, J=11.6 Hz, 1H), 4.03 (q, J=7.1 Hz, 2H), 3.69 (q, J=7.1 Hz, 2H), 1.40 (s, 9H), 1.15 (t, J=7.1 Hz, 3H), 0.95 (t, J=7.1 Hz, 3H).

$^{13}$C NMR: (100 MHz, CDCl$_3$) δ 168.9, 159.5, 154.6, 148.6, 142.5, 142.1, 141.8, 138.2, 131.5, 131.3, 130.8, 130.7, 129.92, 129.90, 129.7, 129.1, 128.07, 128.05, 127.5, 127.3, 126.3, 125.8, 125.5, 103.7, 80.2, 70.1, 70.0, 61.1, 45.2, 28.5, 14.1, 13.9.

IR: (film) 1698, 1290, 1253, 1151, 758 cm$^{-1}$.
HRMS: (ESI+) m/z calc'd for (M+H)$^+$ [C$_{34}$H$_{36}$N$_2$O$_6$+H]$^+$: 569.2646, found 569.2651.

Example 35

Arylation Product 3gp:

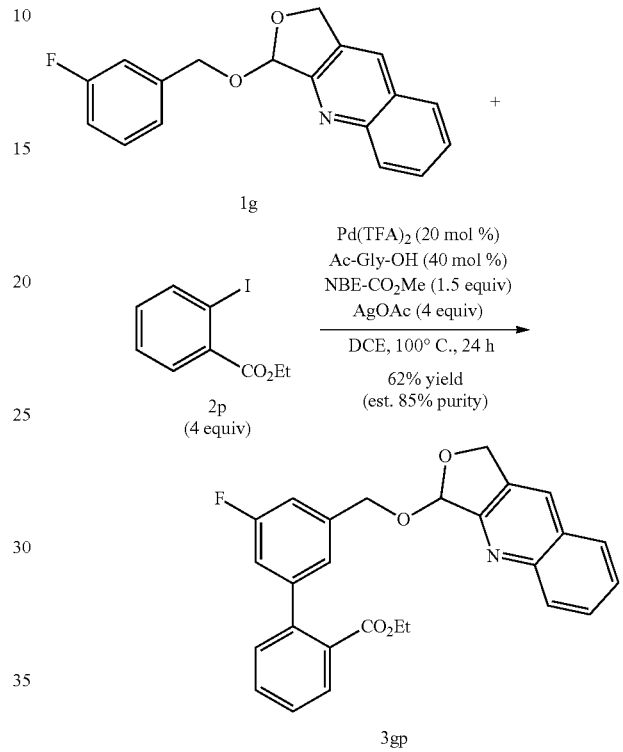

To a 2-dram vial with a PTFE-lined cap was charged with acetal 1g (29.8 mg, 0.101 mmol), ethyl 2-iodobenzoate (110 mg, 0.399 mmol), NBE-CO$_2$Me (22.0 mg, 0.145 mmol), Pd(TFA)$_2$ (6.6 mg, 0.0199 mmol), TFA-Gly-OH (6.9 mg, 0.0404 mmol), AgOAc (67.0 mg, 0.401 mmol), and DCE (2.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (4:1 hexanes/EtOAc eluent) to afford arylation product 3gp (27.7 mg, 62% yield, R$_f$=0.25 in 2:1 hexanes/EtOAc) as a light yellow oil. Product 3gp was determined to be of 85% purity with an unidentified additional compound, on the basis of integration of the terminal methyl protons of the $^1$H NMR spectrum.

$^1$H NMR: (400 MHz, CDCl$_3$) δ 8.17 (d, J=8.5 Hz, 1H), 8.06 (s, 1H), 7.88-7.80 (m, 2H), 7.76-7.69 (m, 1H), 7.58 (app. t, J=7.2 Hz, 1H), 7.53-7.48 (m, 1H), 7.46-7.38 (m, 1H), 7.33 (d, J=7.6 Hz, 1H), 7.17 (d, J=9.2 Hz, 1H), 7.13 (s, 1H), 6.94 (d, J=9.3 Hz, 1H), 6.32 (s, 1H), 5.40 (d, J=13.3 Hz, 1H), 5.23 (d, J=13.3 Hz, 1H), 4.96 (d, J=11.9 Hz, 1H), 4.87 (d, J=11.9 Hz, 1H), 4.07 (q, J=7.1 Hz, 2H), 0.99 (t, J=7.1 Hz, 3H).

$^{13}$C NMR: (100 MHz, CDCl$_3$) δ 168.5, 162.7 (d, J=245.9 Hz), 159.3, 148.7, 143.7 (d, J=8.2 Hz), 141.2 (d, J=2.0 Hz), 140.1 (d, J=8.0 Hz), 131.4, 131.3, 130.72, 130.65, 130.1, 129.9, 129.8, 129.2, 128.10, 128.07, 127.8, 127.4, 123.8 (d, J=2.6 Hz), 114.9 (d, J=22.2 Hz), 113.7 (d, J=21.8 Hz), 103.8, 70.2, 69.6 (d, J=1.5 Hz), 61.2, 13.9.

$^{19}$F NMR: (376 MHz, CDCl$_3$) δ −114.2.

IR: (film) 1717, 1290, 1253, 1024, 761 cm$^{-1}$.

HRMS: (ESI+) m/z calc'd for (M+H)$^+$ [C$_{27}$H$_{22}$FNO$_4$+H]$^+$: 444.1606, found 444.1609.

Example 36

Arylation Product 3hp:

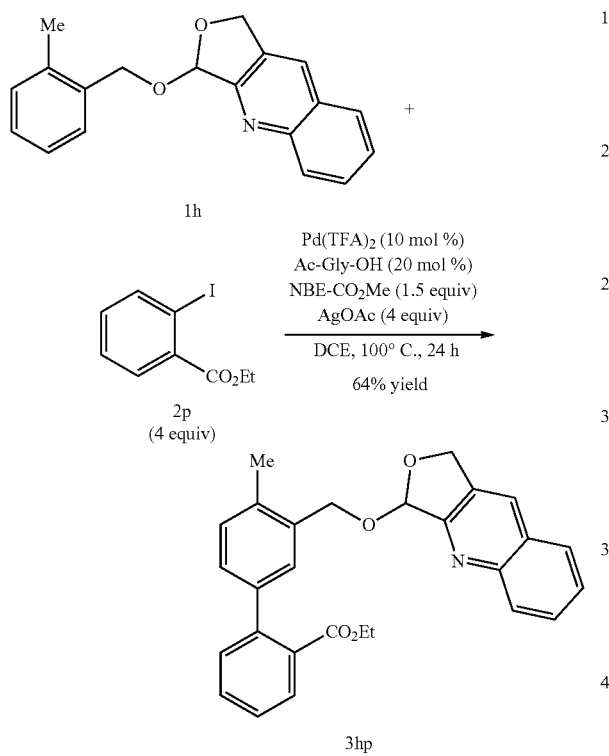

To a 2-dram vial with a PTFE-lined cap was charged with acetal 1h (28.7 mg, 0.0986 mmol), ethyl 2-iodobenzoate (111 mg, 0.402 mmol), NBE-CO$_2$Me (23.7 mg, 0.156 mmol), Pd(TFA)$_2$ (3.2 mg, 0.00964 mmol), TFA-Gly-OH (3.3 mg, 0.0193 mmol), AgOAc (65.7 mg, 0.393 mmol), and DCE (2.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (4:1 hexanes/EtOAc eluent) to afford arylation product 3hp (27.7 mg, 64% yield, R$_f$=0.27 in 2:1 hexanes/EtOAc) as a colorless oil. (15% recovery of starting material 1h was observed in the crude NMR prior to purification.)

$^1$H NMR: (400 MHz, CDCl$_3$) δ 8.15 (d, J=8.5 Hz, 1H), 8.04 (s, 1H), 7.83 (d, J=8.1 Hz, 1H), 7.80-7.76 (m, 1H), 7.74-7.67 (m, 1H), 7.59-7.53 (m, 1H), 7.51-7.44 (m, 1H), 7.40 (d, J=1.4 Hz, 1H), 7.39-7.33 (m, 2H), 7.18 (d, J=7.8 Hz, 1H), 7.14 (dd, J=7.7, 1.8 Hz, 1H), 6.32 (s, 1H), 5.40 (d, J=13.3 Hz, 1H), 5.23 (d, J=13.3 Hz, 1H), 5.03 (d, J=11.3 Hz, 1H), 4.86 (d, J=11.3 Hz, 1H), 4.07 (q, J=7.1 Hz, 2H), 2.45 (s, 3H), 0.99 (t, J=7.1 Hz, 3H).

$^{13}$C NMR: (100 MHz, CDCl$_3$) δ 169.0, 159.6, 148.6, 142.4, 139.1, 136.1, 135.4, 131.4, 131.2, 131.0, 130.8, 130.1, 130.0, 129.8, 129.6, 129.4, 129.0, 128.2, 128.1, 128.0, 127.2, 127.1, 103.7, 70.1, 68.9, 61.1, 18.9, 14.0.

IR: (film) 1717, 1266, 1011, 759, 736 cm$^{-1}$.

HRMS: (ESI+) m/z calc'd for (M+H)$^+$ [C$_{28}$H$_{25}$NO$_4$+H]$^+$: 440.1856, found 440.1862.

Example 37

Arylation Product 3in:

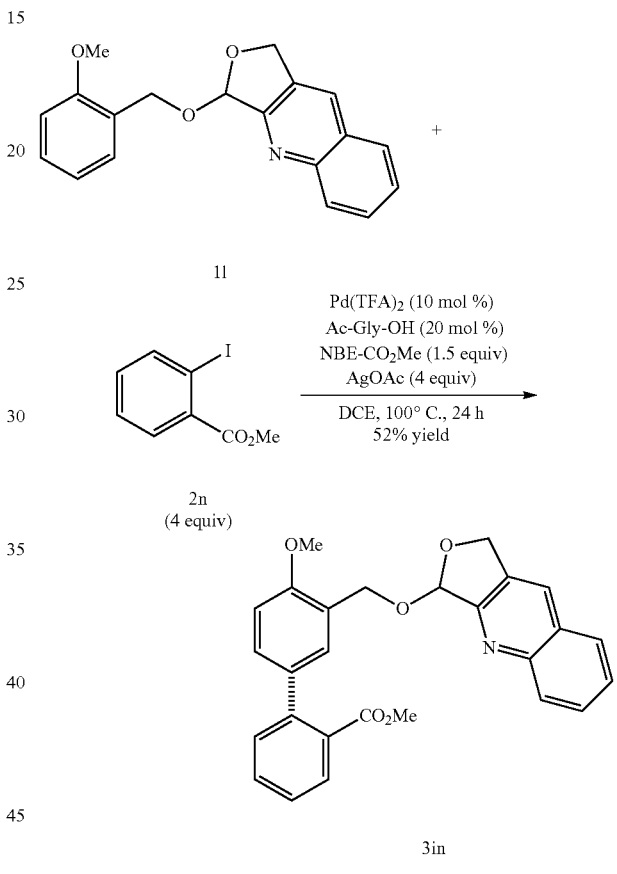

To a 2-dram vial with a PTFE-lined cap was charged with acetal 1i (30.2 mg, 0.0984 mmol), methyl 2-iodobenzoate (104 mg, 0.397 mmol), NBE-CO$_2$Me (23.0 mg, 0.151 mmol), Pd(TFA)$_2$ (3.3 mg, 0.00994 mmol), TFA-Gly-OH (3.4 mg, 0.0199 mmol), AgOAc (67.3 mg, 0.403 mmol), and DCE (2.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (4:1:1 hexanes/EtOAc/CH$_2$Cl$_2$ eluent) to afford arylation product 3in (22.4 mg, 52% yield, R$_f$=0.19 in 2:1 hexanes/EtOAc) as a colorless oil. (21% recovery of starting material 1i was observed in the crude NMR prior to purification.)

$^1$H NMR: (400 MHz, CDCl$_3$) δ 8.15 (d, J=8.5 Hz, 1H), 8.03 (s, 1H), 7.82 (d, J=8.0 Hz, 1H), 7.75 (dd, J=7.7, 1.0 Hz,

1H), 7.73-7.67 (m, 1H), 7.59-7.52 (m, 1H), 7.50-7.43 (m, 2H), 7.40-7.30 (m, 2H), 7.20 (dd, J=8.4, 2.3 Hz, 1H), 6.88 (d, J=8.4 Hz, 1H), 6.35 (s, 1H), 5.40 (d, J=13.3 Hz, 1H), 5.21 (d, J=13.3 Hz, 1H), 5.03 (d, J=12.3 Hz, 1H), 4.95 (d, J=12.3 Hz, 1H), 3.88 (s, 3H), 3.60 (s, 3H).

$^{13}$C NMR: (100 MHz, CDCl$_3$) δ 169.6, 159.8, 156.7, 148.6, 142.2, 133.4, 131.3, 131.0, 130.9, 130.0, 129.8, 129.64, 129.55, 129.0, 128.8, 128.1, 128.0, 127.2, 126.8, 126.2, 110.0, 103.9, 70.0, 65.3, 55.7, 52.1.

IR: (film) 1725, 1291, 1265, 1023, 738 cm$^{-1}$.

HRMS: (ESI+) m/z calc'd for (M+H)$^+$ [C$_{27}$H$_{23}$NO$_5$+H]$^+$: 442.1649, found 442.1656.

Example 38

Arylation Product 3jn:

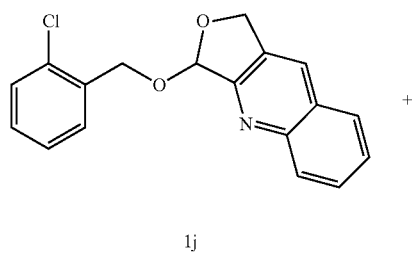

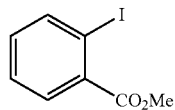

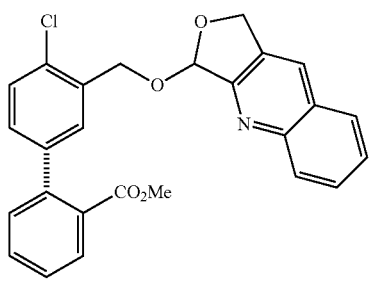

To a 2-dram vial with a PTFE-lined cap was charged with acetal 1j (30.8 mg, 0.0987 mmol), methyl 2-iodobenzoate (105 mg, 0.401 mmol), NBE-CO$_2$Me (22.2 mg, 0.146 mmol), Pd(TFA)$_2$ (3.4 mg, 0.0102 mmol), TFA-Gly-OH (3.4 mg, 0.0199 mmol), AgOAc (68.2 mg, 0.408 mmol), and DCE (2.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (4:1 hexanes/EtOAc eluent) to afford arylation product 3jn (23.6 mg, 54% yield, R$_f$=0.27 in 2:1 hexanes/EtOAc) as a colorless oil. (24% recovery of starting material 1j was observed in the crude NMR prior to purification.)

$^1$H NMR: (400 MHz, CDCl$_3$) δ 8.15 (d, J=8.5 Hz, 1H), 8.06 (s, 1H), 7.87-7.78 (m, 2H), 7.75-7.68 (m, 1H), 7.60-7.54 (m, 2H), 7.49 (app. td, J=7.5, 1.3 Hz, 1H), 7.42-7.32 (m, 3H), 7.14 (dd, J=8.2, 2.2 Hz, 1H), 6.36 (s, 1H), 5.42 (d, J=13.3 Hz, 1H), 5.24 (d, J=13.3 Hz, 1H), 5.11 (d, J=12.8 Hz, 1H), 4.99 (d, J=12.8 Hz, 1H), 3.60 (s, 3H).

$^{13}$C NMR: (100 MHz, CDCl$_3$) δ 168.9, 159.4, 148.6, 141.6, 140.2, 135.5, 132.1, 131.6, 131.0, 130.8, 130.7, 130.1, 129.9, 129.7, 129.5, 129.1, 128.9, 128.8, 128.10, 128.06, 127.6, 127.3, 104.0, 70.2, 67.5, 52.2.

IR: (film) 1725, 1291, 1266, 1024, 737 cm$^{-1}$.

HRMS: (ESI+) m/z calc'd for (M+H)$^+$ [C$_{26}$H$_{20}$ClNO$_4$+H]$^+$: 446.1154, found 446.1160.

Example 39

Arylation Product 3kp:

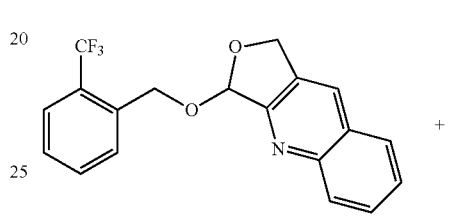

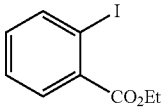

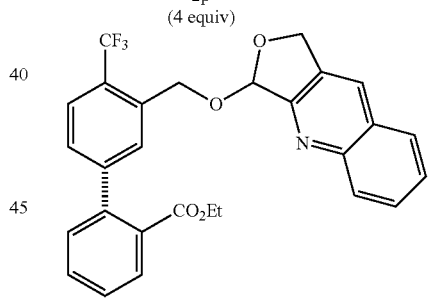

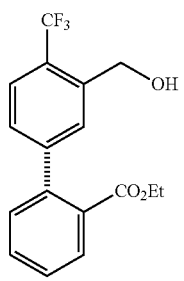

To a 2-dram vial with a PTFE-lined cap was charged with acetal 1k (34.4 mg, 0.0997 mmol), ethyl 2-iodobenzoate (110 mg, 0.399 mmol), NBE-CO$_2$Me (21.9 mg, 0.144 mmol), Pd(TFA)$_2$ (3.4 mg, 0.0102 mmol), TFA-Gly-OH (3.5 mg, 0.0205 mmol), AgOAc (67.1 mg, 0.402 mmol), and DCE (2.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (5:1 hexanes/EtOAc eluent) to afford arylation product 3kp together with an unidentified impurity (27.0 mg total). (53% recovery of starting material 1k was also observed in the crude NMR prior to purification.) Impure arylation product 3kp was then dissolved in MeOH (2.00 mL), HCl (gas) was bubbled through the mixture until the pH ~1, and the mixture was stirred at room temperature for 22 h. Sat. aq. Na$_2$CO$_3$ (5 mL) and water (10 mL) were then added, and the mixture was extracted with EtOAc (3×15 mL). The combined organic layers were washed with brine (10.0 mL) and dried over anhydrous Na$_2$SO$_4$. The solvent was removed by rotary evaporation, and the resulting residue was purified by preparative TLC (3:1 hexanes/EtOAc eluent) to afford biaryl alcohol 6kp (11.9 mg, 37% yield, R$_f$=0.44 in 2:1 hexanes/EtOAc) as a colorless oil.

$^1$H NMR: (500 MHz, CDCl$_3$) δ 7.91 (d, J=7.7 Hz, 1H), 7.68 (s, 1H), 7.66 (d, J=8.1 Hz, 1H), 7.59-7.53 (m, 1H), 7.46 (app. t, J=7.6 Hz, 1H), 7.35 (d, J=7.6 Hz, 1H), 7.32 (d, J=7.9 Hz, 1H), 4.92 (d, J=2.7 Hz, 2H), 4.12 (q, J=7.1 Hz, 2H), 1.95 (br. s, 1H), 1.05 (t, J=7.1 Hz, 3H).

$^{13}$C NMR: (100 MHz, CDCl$_3$) δ 168.2, 145.9, 141.5, 139.2, 131.7, 130.9, 130.8, 130.4, 129.1, 128.2, 127.6, 125.7 (q, J=5.6 Hz), 61.6 (q, J=2.8 Hz), 61.3, 13.9.

$^{19}$F NMR: (376 MHz, CDCl$_3$) δ -59.8.

IR: (film) 3462, 1716, 1315, 1160, 1121 cm$^{-1}$.

HRMS: (ESI+) m/z calc'd for (M+Na)$^+$ [C$_{17}$H$_{15}$F$_3$O$_3$+Na]$^+$: 347.0866, found 347.0866.

Example 40

Arylation Product 3/n:

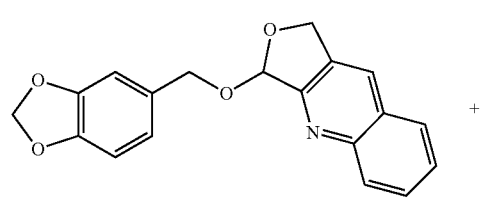

11

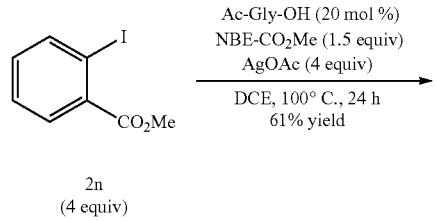

2n
(4 equiv)

Pd(TFA)$_2$ (10 mol %)
Ac-Gly-OH (20 mol %)
NBE-CO$_2$Me (1.5 equiv)
AgOAc (4 equiv)
―――――――――→
DCE, 100° C., 24 h
61% yield

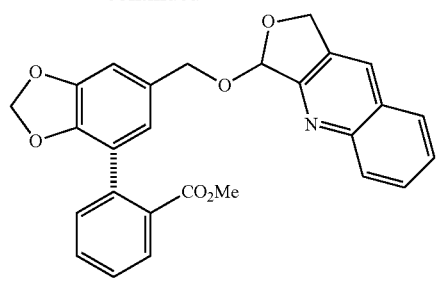

3ln

To a 2-dram vial with a PTFE-lined cap was charged with acetal 11 (32.0 mg, 0.0997 mmol), methyl 2-iodobenzoate (104 mg, 0.397 mmol), NBE-CO$_2$Me (23.0 mg, 0.151 mmol), Pd(TFA)$_2$ (3.4 mg, 0.0102 mmol), TFA-Gly-OH (3.5 mg, 0.0205 mmol), AgOAc (65.7 mg, 0.393 mmol), and DCE (2.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (3:1:1 hexanes/EtOAc/CH$_2$Cl$_2$ eluent) to afford arylation product 3ln (27.7 mg, 61% yield, R$_f$=0.19 in 2:1 hexanes/EtOAc) as a colorless oil.

$^1$H NMR: (400 MHz, CDCl$_3$) δ 8.18 (d, J=8.5 Hz, 1H), 8.05 (s, 1H), 7.89 (dd, J=7.7, 0.9 Hz, 1H), 7.84 (d, J=8.0 Hz, 1H), 7.76-7.69 (m, 1H), 7.61-7.50 (m, 2H), 7.47-7.37 (m, 2H), 6.99 (d, J=1.3 Hz, 1H), 6.93 (s, 1H), 6.32 (s, 1H), 5.90 (s, 2H), 5.41 (d, J=13.3 Hz, 1H), 5.24 (d, J=13.3 Hz, 1H), 4.90 (d, J=11.2 Hz, 1H), 4.82 (d, J=11.2 Hz, 1H), 3.70 (s, 3H).

$^{13}$C NMR: (100 MHz, CDCl$_3$) δ 168.6, 159.6, 148.7, 147.5, 144.6, 136.4, 131.9, 131.7, 131.3, 131.0, 130.8, 130.3, 130.0, 129.7, 129.1, 128.11, 128.05, 127.9, 127.3, 122.7, 122.6, 108.6, 103.5, 101.3, 70.4, 70.1, 52.3.

IR: (film) 1725, 1422, 1291, 1256, 1020 cm$^{-1}$.

HRMS: (ESI+) m/z calc'd for (M+H)$^+$ [C$_{27}$H$_{21}$NO$_6$+H]$^+$: 456.1442, found 456.1446.

Example 41

Arylation Product 3mn:

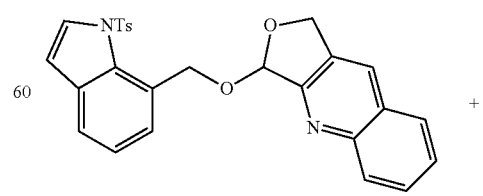

1m

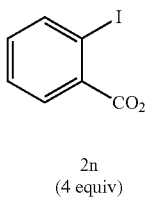

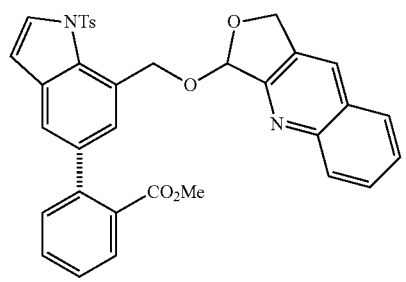

3mn

To a 2-dram vial with a PTFE-lined cap was charged with acetal 1m (46.8 mg, 0.0994 mmol), methyl 2-iodobenzoate (106 mg, 0.405 mmol), NBE-CO$_2$Me (24.5 mg, 0.161 mmol), Pd(TFA)$_2$ (3.4 mg, 0.0102 mmol), TFA-Gly-OH (3.5 mg, 0.0205 mmol), AgOAc (69.3 mg, 0.415 mmol), and DCE (2.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (3:1 hexanes/EtOAc eluent) to afford arylation product 3mn (28.3 mg, 47% yield, $R_f$=0.26 in 2:1 hexanes/EtOAc) as a colorless oil. (17% recovery of starting material 1m was observed in the crude NMR prior to purification.)

$^1$H NMR: (400 MHz, CDCl$_3$) δ 8.12 (d, J=8.5 Hz, 1H), 8.06 (s, 1H), 7.86 (d, J=7.8 Hz, 1H), 7.79-7.68 (m, 3H), 7.62-7.56 (m, 2H), 7.53 (d, J=8.4 Hz, 2H), 7.47 (app. td, J=7.6, 1.3 Hz, 1H), 7.41-7.33 (m, 3H), 7.04 (d, J=8.2 Hz, 2H), 6.69 (d, J=3.8 Hz, 1H), 6.36 (s, 1H), 5.41 (d, J=13.5 Hz, 1H), 5.34 (d, J=13.3 Hz, 1H), 5.30 (d, J=13.3 Hz, 1H), 5.22 (d, J=13.5 Hz, 1H), 3.41 (s, 3H), 2.26 (s, 3H).

$^{13}$C NMR: (100 MHz, CDCl$_3$) δ 169.4, 159.6, 148.7, 144.8, 142.1, 137.3, 135.9, 133.3, 132.7, 131.3, 131.23, 131.22, 131.1, 130.7, 129.93, 129.88, 129.85, 129.6, 129.0, 128.12, 128.09, 127.2, 126.9, 126.3, 125.6, 120.3, 110.4, 103.9, 70.3, 67.3, 52.0, 21.7.

IR: (film) 1724, 1172, 1125, 1089, 736 cm$^{-1}$.

HRMS: (ESI+) m/z calc'd for (M+H)$^+$ [C$_{35}$H$_{28}$N$_2$O$_6$S+H]$^+$: 605.1741, found 605.1745.

Example 42

Arylation Product 3np:

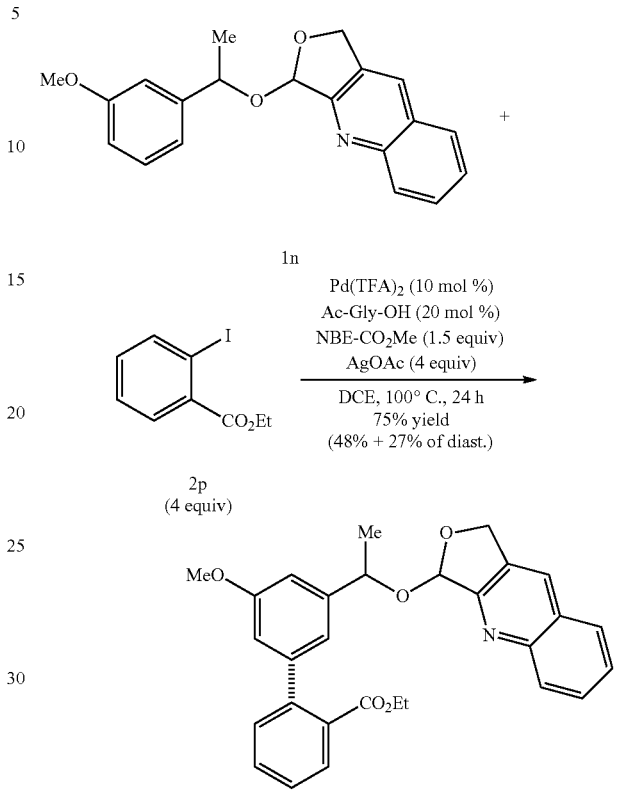

3np

To a 2-dram vial with a PTFE-lined cap was charged with acetal 1n (1.00 mL, 0.100 M in DCE, 0.100 mmol), ethyl 2-iodobenzoate (111 mg, 0.402 mmol), NBE-CO$_2$Me (22.9 mg, 0.151 mmol), Pd(TFA)$_2$ (3.4 mg, 0.0102 mmol), TFA-Gly-OH (3.4 mg, 0.0199 mmol), AgOAc (66.7 mg, 0.399 mmol), and DCE (1.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by flash column chromatography (5:1→4:1→2:1 hexanes/EtOAc eluent) to afford the major arylation product 3np$_{major}$ (22.7 mg, 48% yield, $R_f$=0.37 in 2:1 hexanes/EtOAc) as a colorless oil. The minor arylation product was also isolated from this column and further purified by preparative TLC (3:1:1 hexanes/EtOAc/CH$_2$Cl$_2$ eluent) to afford product 3np$_{minor}$ (12.5 mg, 27% yield, $R_f$=0.26 in 2:1 hexanes/EtOAc) as a colorless oil. Major product (3np$_{major}$): $^1$H NMR: (400 MHz, CDCl$_3$) δ 8.12 (d, J=8.5 Hz, 1H), 8.03 (s, 1H), 7.85-7.79 (m, 2H), 7.74-7.66 (m, 1H), 7.59-7.51 (m, 2H), 7.47 (d, J=6.7 Hz, 1H), 7.43 (app. td, J=7.6, 1.2 Hz, 1H), 7.24 (s, 1H), 7.05 (s, 1H), 6.84 (app. t, J=1.9 Hz, 1H), 6.12 (s, 1H), 5.41 (d, J=13.2 Hz, 1H), 5.18 (d, J=13.2 Hz, 1H), 5.12 (q, J=6.6 Hz, 1H), 4.09 (q, J=7.1 Hz, 2H), 3.94 (s, 3H), 1.55 (d, J=6.6 Hz, 3H), 1.00 (t, J=7.1 Hz, 3H).

$^{13}$C NMR: (100 MHz, CDCl$_3$) δ 169.2, 160.0, 159.9, 148.8, 144.5, 143.1, 142.3, 131.7, 131.2, 130.84, 130.82, 130.1, 129.8, 129.4, 128.8, 128.1, 128.0, 127.5, 127.1, 119.8, 114.0, 110.8, 101.8, 75.6, 69.8, 61.2, 55.7, 24.6, 14.0.

IR: (film) 1719, 1593, 1290, 1258, 1009 cm$^{-1}$.

HRMS: (ESI+) m/z calc'd for (M+H)$^+$ [C$_{29}$H$_{27}$NO$_5$+H]$^+$: 470.1962, found 470.1976. Minor product (3np$_{minor}$): $^1$H NMR: (400 MHz, CDCl$_3$) δ 8.19 (d, J=8.5 Hz, 1H), 8.02 (s, 1H), 7.82 (d, J=8.1 Hz, 1H), 7.79-7.75 (m, 1H), 7.75-7.69 (m, 1H), 7.57 (app. t, J=7.2 Hz, 1H), 7.49 (app. td, J=7.5, 1.3 Hz, 1H), 7.42-7.34 (m, 2H), 6.98 (s, 1H), 6.92 (s, 1H), 6.75 (app. t, J=1.8 Hz, 1H), 6.35 (s, 1H), 5.22 (d, J=13.2 Hz, 1H), 5.15-5.04 (m, 2H), 4.04 (q, J=7.1 Hz, 2H), 3.80 (s, 3H), 1.63 (d, J=6.5 Hz, 3H), 0.96 (t, J=7.1 Hz, 3H).

$^{13}$C NMR: (100 MHz, CDCl$_3$) δ 169.2, 160.2, 159.5, 148.6, 146.0, 142.8, 142.3, 131.8, 131.2, 130.9, 130.6, 130.0, 129.7, 129.6, 129.0, 128.0, 127.4, 127.2, 119.1, 112.9, 110.8, 103.0, 76.2, 69.8, 61.1, 55.6, 23.4, 13.9.

IR: (film) 1720, 1594, 1289, 1257, 1008 cm$^{-1}$.

HRMS: (ESI+) m/z calc'd for (M+H)$^+$ [C$_{29}$H$_{27}$NO$_5$+H]$^+$: 470.1962, found 470.1967.

Example 43

Arylation Products 3op$_{mono}$ and 6op$_{di}$:

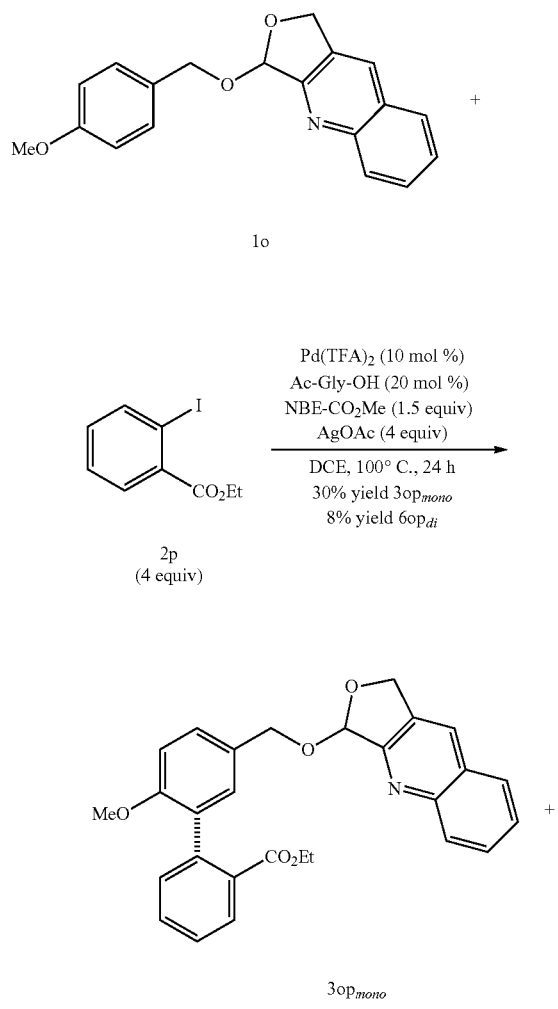

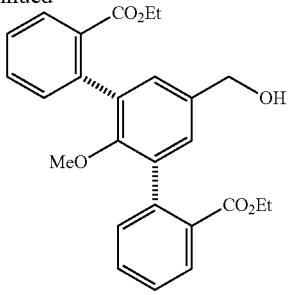

To a 2-dram vial with a PTFE-lined cap was charged with acetal 1o (30.1 mg, 0.0980 mmol), ethyl 2-iodobenzoate (111 mg, 0.402 mmol), NBE-CO$_2$Me (23.1 mg, 0.152 mmol), Pd(TFA)$_2$ (3.3 mg, 0.00994 mmol), TFA-Gly-OH (3.3 mg, 0.0193 mmol), AgOAc (66.0 mg, 0.395 mmol), and DCE (2.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by preparative TLC (2:1 hexanes/EtOAc eluent) to afford arylation product 3op$_{mono}$ (13.6 mg, 30% yield, R$_f$=0.21 in 2:1 hexanes/EtOAc) as a yellow oil and arylation product 3op$_{di}$ together with an unidentified impurity (6.0 mg total). (20% recovery of starting material 1o was also observed in the crude NMR prior to purification.) The impure arylation product 3op$_{di}$ was then dissolved in MeOH (2.00 mL), HCl (gas) was bubbled through the mixture until the pH ~1, and the mixture was stirred at room temperature for 23 h. Saturated aq. Na$_2$CO$_3$ (5 mL) and water (10 mL) were then added, and the mixture was extracted with EtOAc (3×15 mL). The combined organic layers were washed with brine (15 mL) and dried over anhydrous Na$_2$SO$_4$. The solvent was concentrated by rotary evaporation, and the resulting residue was purified by preparative TLC (2:1 hexanes/EtOAc eluent) to afford biaryl alcohol 6op$_{di}$ (3.3 mg, 8% yield, R$_f$=0.21 in 2:1 hexanes/EtOAc) as a colorless oil.

Monoarylation product (3op$_{mono}$): $^1$H NMR: (400 MHz, CDCl$_3$) δ 8.17 (d, J=8.5 Hz, 1H), 8.05 (s, 1H), 7.86 (d, J=7.2 Hz, 1H), 7.83 (d, J=8.2 Hz, 1H), 7.72 (app. t, J=7.7 Hz, 1H), 7.61-7.48 (m, 2H), 7.46-7.30 (m, 4H), 6.86 (d, J=8.4 Hz, 1H), 6.32 (s, 1H), 5.40 (d, J=13.2 Hz, 1H), 5.23 (d, J=13.2 Hz, 1H), 4.93 (d, J=11.1 Hz, 1H), 4.85 (d, J=11.1 Hz, 1H), 4.07 (q, J=7.2 Hz, 2H), 3.69 (s, 3H), 1.02 (t, J=7.2 Hz, 3H).

$^{13}$C NMR: (100 MHz, CDCl$_3$) δ 168.5, 159.7, 156.1, 148.6, 138.7, 132.1, 131.63, 131.56, 130.83, 130.80, 130.6, 129.93, 129.85, 129.64, 129.56, 129.2, 129.1, 128.1, 128.0, 127.3, 127.2, 110.2, 103.4, 70.2, 70.1, 60.8, 55.5, 14.0.

IR: (film) 1721, 1503, 1289, 1251, 1020 cm$^{-1}$.

HRMS: (ESI+) m/z calc'd for (M+H)$^+$ [C$_{28}$H$_{25}$NO$_5$+H]$^+$: 456.1805, found 456.1813. Diarylation product alcohol (6op$_{di}$): $^1$H NMR: (400 MHz, CDCl$_3$) δ 7.90 (d, J=7.8 Hz, 2H), 7.57-7.49 (m, 2H), 7.46-7.38 (m, 4H), 7.22 (s, 2H), 4.69 (d, J=5.9 Hz, 2H), 4.17 (app. br. s, 4H), 3.01 (s, 3H), 1.66 (t, J=5.9 Hz, 1H), 1.12 (t, J=7.0 Hz, 6H).

$^{13}$C NMR: (125 MHz, CDCl$_3$) δ 168.2, 153.7, 139.0, 136.0, 135.2, 131.6, 131.3, 129.9, 128.6, 127.5, 65.2, 61.0, 60.1, 14.1.

IR: (film) 3473, 1717, 1291, 1254, 1131 cm$^{-1}$.
HRMS: (ESI+) m/z calc'd for (M+Na)$^+$ [C$_{26}$H$_{26}$O$_6$+Na]$^+$: 457.1622, found 457.1627.

Example 44

Arylation Products 3pp$_{mono}$ and 3pp$_{di}$:

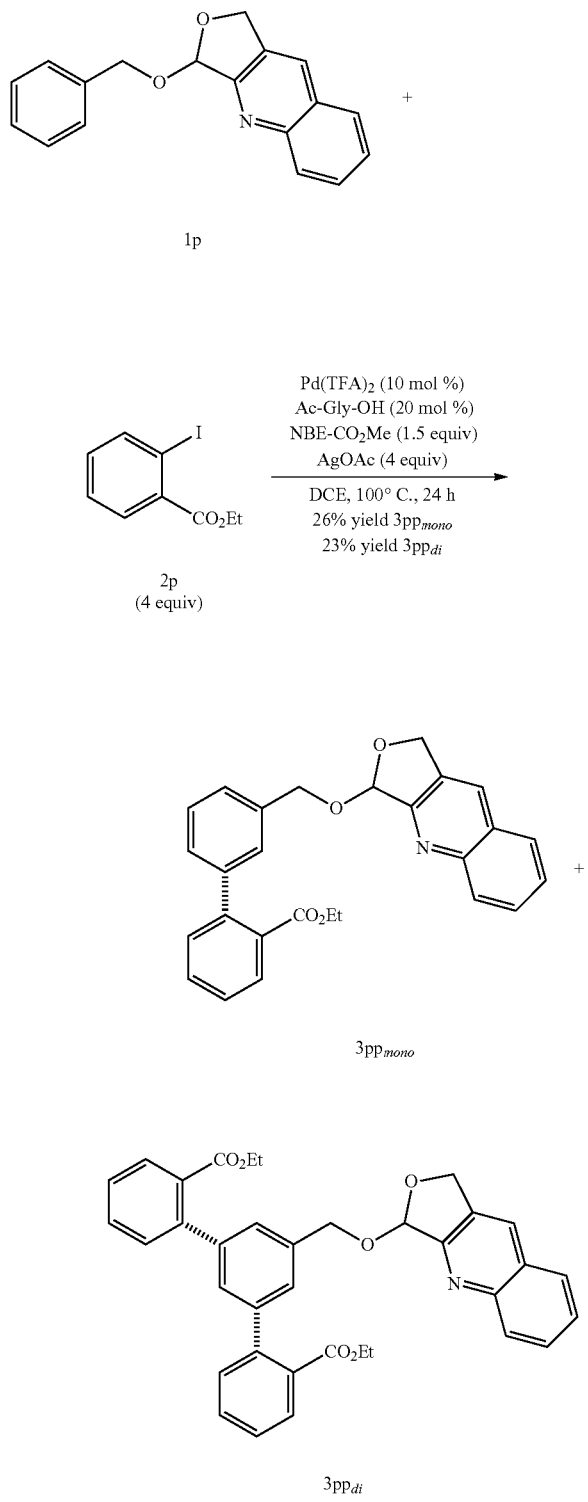

To a 2-dram vial with a PTFE-lined cap was charged with acetal 1p (26.8 mg, 0.0968 mmol), ethyl 2-iodobenzoate (111 mg, 0.402 mmol), NBE-CO$_2$Me (24.1 mg, 0.159 mmol), Pd(TFA)$_2$ (3.4 mg, 0.0102 mmol), TFA-Gly-OH (3.4 mg, 0.0199 mmol), AgOAc (66.8 mg, 0.400 mmol), and DCE (2.00 mL). The resulting mixture was heated to 100° C. and stirred for 24 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by preparative TLC (2:1 hexanes/EtOAc eluent) to afford the arylation product 3pp$_{mono}$ (10.5 mg, 26% yield, R$_f$=0.33 in 2:1 hexanes/EtOAc) and the arylation product 3pp$_{di}$ (12.8 mg, 23% yield, R$_f$=0.26 in 2:1 hexanes/EtOAc), both as light yellow oils. (19% recovery of starting material 1p was observed in the crude NMR prior to purification.)

Monoarylation product (3pp$_{mono}$): $^1$H NMR: (400 MHz, CDCl$_3$) δ 8.17 (d, J=8.5 Hz, 1H), 8.06 (s, 1H), 7.84 (d, J=8.1 Hz, 1H), 7.82-7.78 (m, 1H), 7.75-7.69 (m, 1H), 7.57 (app. t, J=7.3 Hz, 1H), 7.50 (app. td, J=7.5, 1.2 Hz, 1H), 7.44 (d, J=7.6 Hz, 1H), 7.42-7.33 (m, 4H), 7.23 (d, J=7.6 Hz, 1H), 6.33 (s, 1H), 5.41 (d, J=13.3 Hz, 1H), 5.23 (d, J=13.3 Hz, 1H), 4.99 (d, J=11.5 Hz, 1H), 4.89 (d, J=11.5 Hz, 1H), 4.03 (q, J=7.1 Hz, 2H), 0.94 (t, J=7.1 Hz, 3H).

$^{13}$C NMR: (100 MHz, CDCl$_3$) δ 169.0, 159.6, 148.6, 142.4, 141.7, 137.6, 131.5, 131.3, 130.9, 130.8, 130.0, 129.9, 129.7, 129.1, 128.4, 128.2, 128.09, 128.05, 127.4, 127.3, 127.2, 103.7, 70.4, 70.1, 61.1, 13.9.

IR: (film) 1716, 1287, 1247, 1021, 758 cm$^{-1}$.

HRMS: (ESI+) m/z calc'd for (M+H)$^+$ [C$_{27}$H$_{23}$NO$_4$+H]$^+$: 426.1700, found 426.1705. Diarylation product (3pp$_{di}$): $^1$H NMR: (400 MHz, CDCl$_3$) δ 8.16 (d, J=8.5 Hz, 1H), 8.06 (s, 1H), 7.84 (d, J=8.1 Hz, 1H), 7.82-7.78 (m, 2H), 7.74-7.69 (m, 1H), 7.57 (app. t, J=7.5 Hz, 1H), 7.53-7.46 (m, 2H), 7.43-7.36 (m, 6H), 7.21 (s, 1H), 6.34 (s, 1H), 5.41 (d, J=13.4 Hz, 1H), 5.23 (d, J=13.4 Hz, 1H), 5.02 (d, J=11.5 Hz, 1H), 4.91 (d, J=11.5 Hz, 1H), 4.05 (q, J=7.1 Hz, 4H), 0.97 (t, J=7.1 Hz, 6H).

$^{13}$C NMR: (100 MHz, CDCl$_3$) δ 168.9, 159.6, 148.6, 142.1, 141.5, 137.5, 131.6, 131.3, 130.9, 130.8, 129.93, 129.90, 129.7, 129.1, 128.09, 128.06, 127.4, 127.3, 103.7, 70.2, 70.1, 61.2, 13.9.

IR: (film) 1716, 1291, 1252, 1020, 759 cm$^{-1}$.

HRMS: (ESI+) m/z calc'd for (M+H)$^+$ [O$_{36}$H$_{31}$NO$_6$+H]$^+$: 574.2224, found 574.2231.

Example 45

Two-Step Arylation/Scaffold Cleavage and Telescoping Procedure:
Two-Step Arylation/Scaffold Cleavage:

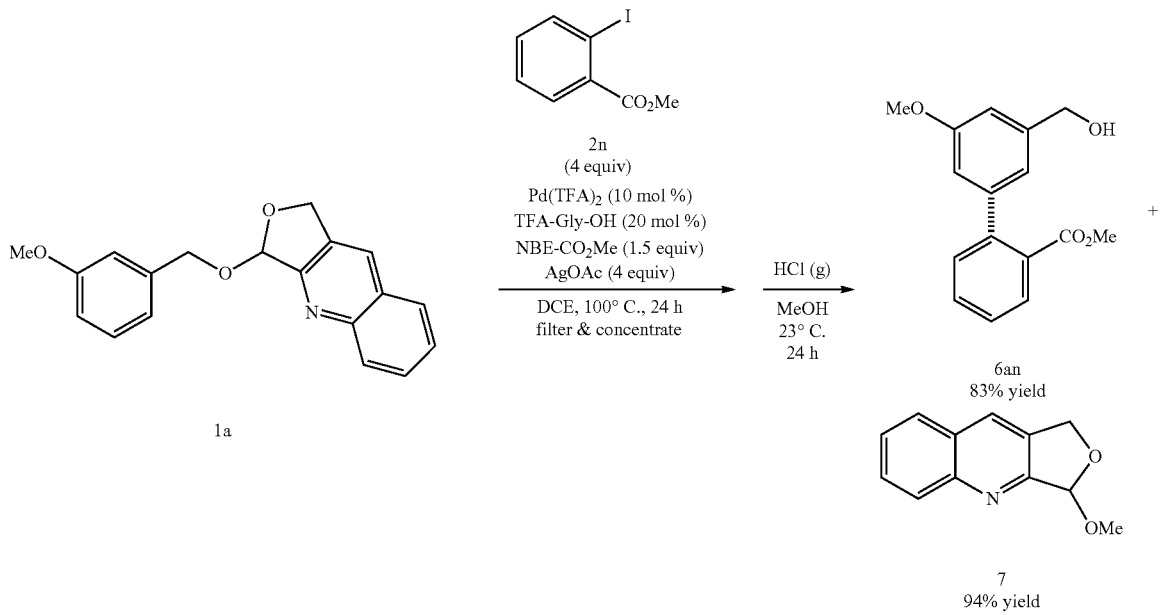

Biaryl Alcohol 6an.

To a 2-dram vial with a PTFE-lined cap was charged with acetal 1a (1.00 mL, 0.100 M in DCE, 0.100 mmol), methyl 2-iodobenzoate (106 mg, 0.405 mmol), NBE-CO$_2$Me (23.8 mg, 0.157 mmol), Pd(TFA)$_2$ (3.4 mg, 0.0102 mmol), TFA-Gly-OH (3.4 mg, 0.0199 mmol), AgOAc (66.2 mg, 0.396 mmol), and DCE (1.00 mL). The resulting mixture was heated to 100° C. and stirred for 24 h. The reaction mixture was cooled to ambient temperature and filtered through a plug of silica gel, eluting with EtOAc (30 mL). The filtrate was concentrated by rotary evaporation, and the resulting residue was dissolved in MeOH (2.00 mL). HCl (gas) was bubbled through the mixture until the pH was at about 1.0, and the mixture was stirred at room temperature for 24 h. Saturated aq. Na$_2$CO$_3$ (5 mL) and water (10 mL) were added, and the mixture was extracted with EtOAc (3×15 mL). The combined organic layers were washed with brine (15 mL) and dried over anhydrous Na$_2$SO$_4$. The mixture was concentrated by rotary evaporation, and the resulting residue was purified by flash column chromatography (3:1→2:1 hexanes/EtOAc eluent) to afford biaryl alcohol 6an (22.5 mg, 83% yield, R$_f$=0.23 in 1:1 hexanes/EtOAc) as a light yellow oil. The quinoline-based methyl acetal (7) was also isolated from this column, and it was further purified by preparative TLC (1:1 hexanes/EtOAc eluent) to afford acetal 7 (18.8 mg, 94% yield, R$_f$=0.32 in 2:1 hexanes/EtOAc) as a light yellow oil.

$^1$H NMR: (400 MHz, CDCl$_3$) δ 7.80 (dd, J=7.7, 0.9 Hz, 1H), 7.52 (app. td, J=7.5, 1.3 Hz, 1H), 7.44-7.34 (m, 2H), 6.92 (s, 1H), 6.89 (s, 1H), 6.78 (s, 1H), 4.69 (s, 2H), 3.82 (s, 3H), 3.66 (s, 3H), 1.93 (s, 1H).

$^{13}$C NMR: (100 MHz, CDCl$_3$) δ 169.3, 159.8, 143.0, 142.5, 142.3, 131.5, 131.0, 130.8, 129.9, 127.5, 119.5, 113.5, 111.4, 65.4, 55.5, 52.3.

IR: (film) 3493, 1724, 1294, 1266, 739 cm$^{-1}$.

HRMS: (ESI+) m/z calc'd for (M+Na)$^+$ [C$_{16}$H$_{16}$O$_4$+Na]$^+$: 295.0941, found 295.0942.

Telescoping Procedure:

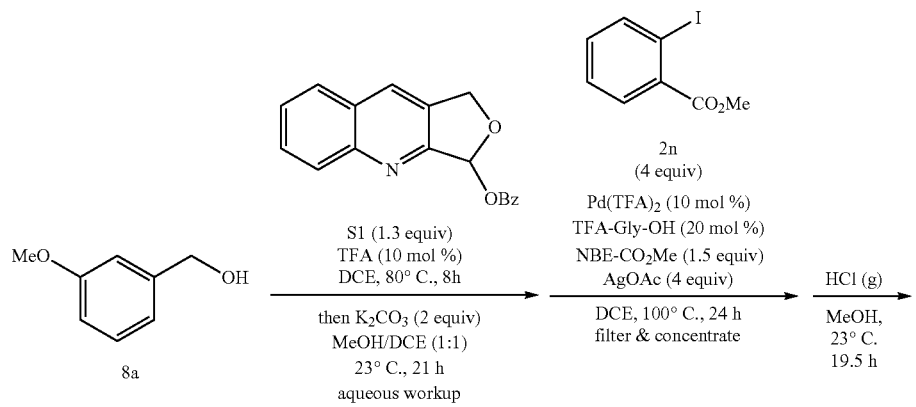

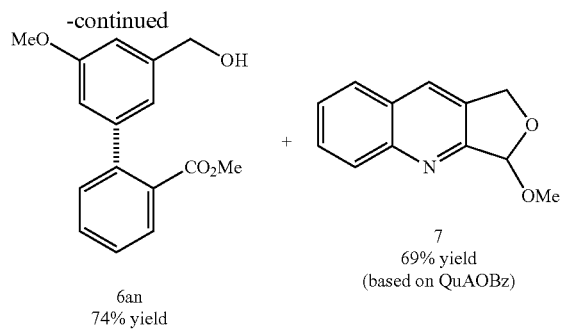

6an
74% yield 7
69% yield
(based on QuAOBz)

Arylation Product Alcohol 6an.

A 2-dram vial was charged with (3-methoxyphenyl) methanol (41.8 mg, 0.303 mmol) and benzoate S1 (115 mg, 0.395 mmol). These were dissolved in DCE (1.00 mL), and TFA (2.2 µL, 0.0298 mmol) was added. The resulting mixture was heated to 80° C. and stirred for 8 h. After cooling to room temperature, $K_2CO_3$ (83.0 mg, 0.601 mmol) and MeOH (1.00 mL) were added, and the resulting mixture was stirred at 23° C. for 21 h. The mixture was filtered through a plug of silica gel and washed with EtOAc (50 mL). The organic layer was then washed sequentially with 10% aq. NaOH (15 mL), water (6×15 mL), and brine (15 mL), and then dried over anhydrous $Na_2SO_4$. Evaporation and dried on vacuum gave the crude product, which was used directly in the next step.

A suspension of the crude material (assume 0.303 mmol), methyl 2-iodobenzoate (313 mg, 1.19 mmol), NBE-$CO_2$Me (69.2 mg, 0.455 mmol), Pd(TFA)$_2$ (9.9 mg, 0.0298 mmol), TFA-Gly-OH (10.3 mg, 0.0602 mmol), and AgOAc (202 mg, 1.21 mmol) in DCE (1.00 mL) in a tube sealed with a PTFE-lined cap was heated at 100° C. and stirred for 24 h. The reaction mixture was cooled to ambient temperature and filtered through a plug of silica gel, eluting with EtOAc (100 mL). The filtrate was concentrated by rotary evaporation, and the resulting residue was dissolved in MeOH (6.00 mL). HCl (gas) was bubbled through the mixture until the pH ~1, and the mixture was stirred at room temperature for 19.5 h. Saturated aq. $Na_2CO_3$ (10 mL) and water (10 mL) were added, and the mixture was extracted with EtOAc (3×20 mL). The combined organic layers were washed with brine (15 mL) and dried over anhydrous $Na_2SO_4$. The mixture was concentrated by rotary evaporation, and the resulting residue was purified by flash column chromatography (3:1:1→2:1:1 hexanes/EtOAc/$CH_2Cl_2$ eluent) to afford biaryl alcohol 6an (61.0 mg, 74% yield) as a light yellow oil. The quinoline-based methyl acetal (7) was also isolated from this column, and it was further purified by preparative TLC (2:1:1 hexanes/EtOAc/$CH_2Cl_2$ eluent) to afford acetal 7 (54.4 mg, 69% yield based on benzoate S1) as a light yellow oil.

Example 46

Secondary Functionalization Studies:

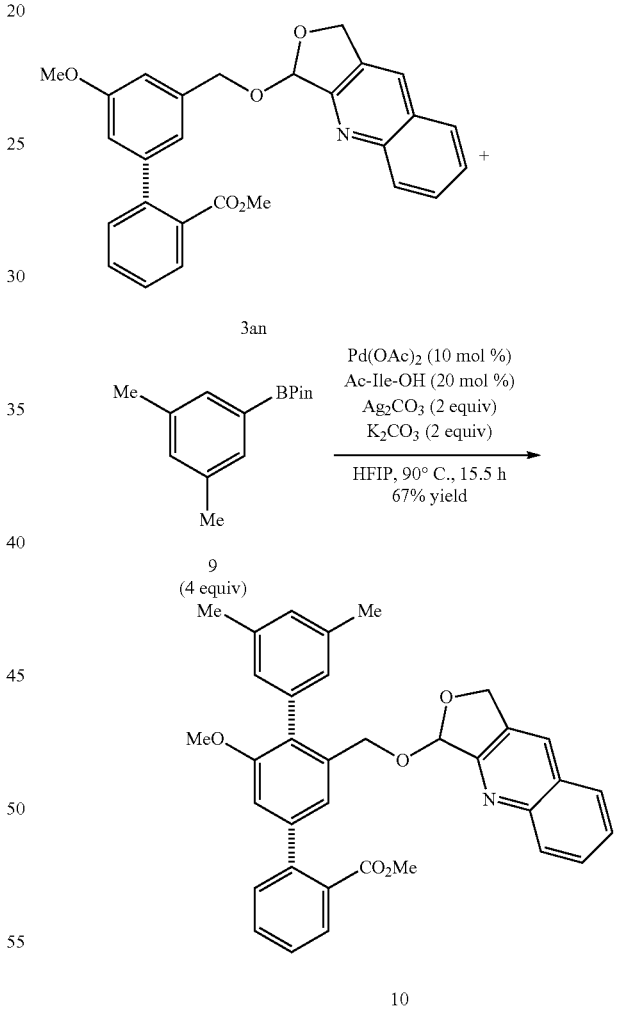

Arylation Product 10:

A Suspension of Acetal 3an (22.3 mg, 0.0506 Mmol), 3,5-Me$_2$C$_6$H$_3$BPin (9, 46.4 mg, 0.200 mmol), Pd(OAc)$_2$ (1.1 mg, 0.00491 mmol), N-acetylisoleucine (1.7 mg, 0.00994 mmol), Ag$_2$CO$_3$ (27.2 mg, 0.0986 mmol), and K$_2$CO$_3$ (13.1 mg, 0.0949 mmol) in hexafluoroisopropanol (1.00 mL) in a 2-dram vial with a PTFE-lined cap was heated at 90° C. and stirred for 15.5 h. The reaction mixture was cooled to ambient temperature and filtered through a plug of silica gel, eluting with diethyl ether (50 mL). The filtrate was concentrated by rotary evaporation, and the resulting residue was purified by preparative TLC (2:1 hexanes/EtOAc eluent) to afford arylation product 10 (18.4 mg, 67% yield, $R_f$=0.36 in 2:1 hexanes/EtOAc) as a light yellow oil.

$^1$H NMR: (400 MHz, CDCl$_3$) δ 8.13 (d, J=8.5 Hz, 1H), 8.01 (s, 1H), 7.82 (d, J=8.1 Hz, 1H), 7.76 (d, J=7.6 Hz, 1H), 7.74-7.67 (m, 1H), 7.60-7.44 (m, 3H), 7.39 (app. td, J=7.6, 1.5 Hz, 1H), 7.24 (d, J=1.3 Hz, 1H), 7.00 (s, 2H), 6.92 (s, 1H), 6.85 (d, J=1.3 Hz, 1H), 6.13 (s, 1H), 5.27 (d, J=13.3 Hz, 1H), 5.13 (d, J=13.3 Hz, 1H), 4.75 (d, J=11.7 Hz, 1H), 4.59 (d, J=11.7 Hz, 1H), 3.72 (s, 3H), 3.62 (s, 3H), 2.41 (s, 3H), 2.34 (s, 3H).

$^{13}$C NMR: (100 MHz, CDCl$_3$) δ 169.7, 159.8, 156.6, 148.6, 142.3, 141.1, 137.6, 137.3, 137.2, 135.9, 131.4, 131.3, 130.9, 130.8, 129.9, 129.8, 129.7, 129.5, 129.2, 128.9, 128.2, 128.1, 128.03, 128.01, 127.3, 127.2, 121.3, 110.5, 103.8, 69.9, 68.7, 56.1, 52.3, 21.7.

IR: (film) 1727, 1292, 1067, 1021, 730 cm$^{-1}$.

HRMS: (ESI+) m/z calc'd for (M+H)$^+$ [O$_{35}$H$_{31}$NO$_5$+H]$^+$: 546.2275, found 546.2282.

In addition to analyses of NMR spectra, 1D selective NOESY experiments were performed on product 10 to confirm the meta-selectivity in C—H arylation and secondary ortho-selectivity in C—H arylation.

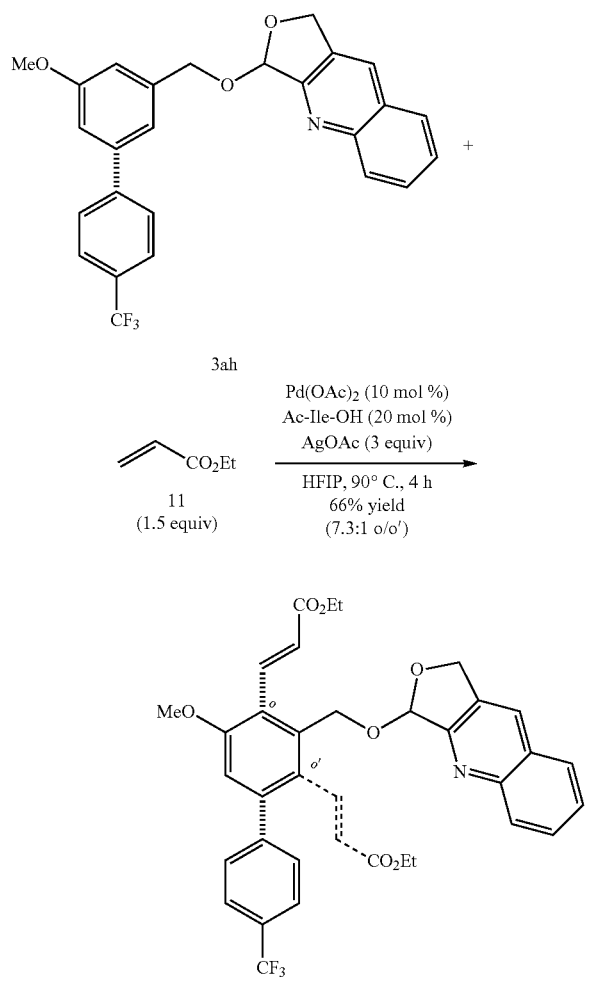

Example 47

Olefin 11:

A suspension of acetal 3ah (26.3 mg, 0.0583 mmol), ethyl acrylate (9.1 mg, 0.0910 mmol), Pd(OAc)$_2$ (1.3 mg, 0.00580 mmol), N-acetylglycine (1.4 mg, 0.0120 mmol), and AgOAc (29.9 mg, 0.179 mmol) in hexafluoroisopropanol (1.20 mL) in a 2-dram vial with a PTFE-lined cap was heated at 90° C. and stirred for 4 h. The reaction mixture was cooled to ambient temperature and filtered through a plug of silica gel, eluting with EtOAc (30 mL). The filtrate was concentrated by rotary evaporation, and the resulting residue was purified by flash column chromatography (4:1 hexanes/EtOAc eluent) to afford olefin product 12 (21.2 mg, 66% yield, $R_f$=0.25 in 2:1 hexanes/EtOAc) as a light yellow oil. Olefin product 12 was identified as a 7.3:1 mixture of constitutional isomers based on the site selectivity of olefination.

$^1$H NMR: (400 MHz, CDCl$_3$) δ 8.14 (d, J=8.5 Hz, 1H), 8.07 (s, 1H), 8.00 (d, J=16.2 Hz, 1H), 7.84 (d, J=8.0 Hz, 1H), 7.77-7.65 (m, 5H), 7.57 (app. t, J=7.5 Hz, 1H), 7.46 (d, J=1.2 Hz, 1H), 7.06 (d, J=1.2 Hz, 1H), 6.75 (d, J=16.2 Hz, 1H), 6.37 (s, 1H), 5.61 (d, J=13.5 Hz, 1H), 5.29 (d, J=13.5 Hz, 1H), 5.25 (d, J=11.3 Hz, 1H), 4.91 (d, J=11.3 Hz, 1H), 4.30 (q, J=7.2 Hz, 2H), 3.93 (s, 3H), 1.36 (t, J=7.2 Hz, 3H).

$^{13}$C NMR: (100 MHz, CDCl$_3$) δ 167.9, 159.7, 159.3, 148.6, 144.1, 141.7, 139.0, 137.4, 130.9, 129.9, 129.7, 129.2, 128.2, 128.1, 127.7, 127.3, 126.0 (q, J=3.7 Hz), 123.8, 122.8, 121.8, 109.8, 104.1, 70.4, 68.8, 60.6, 56.0, 14.6.

$^{19}$F NMR: (376 MHz, CDCl$_3$) δ −62.4.

IR: (film) 1709, 1325, 1167, 1123, 1017 cm$^{-1}$.

HRMS: (ESI+) m/z calc'd for (M+H)$^+$ [C$_{31}$H$_{26}$F$_3$NO$_5$+H]$^+$: 550.1836, found 550.1842.

A selective NOESY experiment in conjunction with HMBC data confirmed the selectivity of C—H arylation and C—H olefination for product 12$_{major}$.

Example 47

Optimization Studies:

General Optimization Procedure:

A suspension of substrate acetal 1a (0.050 mmol), iodobenzene (2a, 4.00 equiv), NBE-CO$_2$Me (1.5 equiv), Pd(TFA)$_2$ (10.0 mol %), ligand (20.0 mol %), and Ag salts (4.00 equiv) in DCE (50.0 mM) in a 2-dram vial with a PTFE-lined cap was heated at 100° C. and stirred for the specified time. After cooling to ambient temperature, the mixture was filtered through a plug of silica gel, eluting with EtOAc (30.0 mL). The filtrate was concentrated by rotary evaporation, and the resulting residue was analyzed by $^1$H NMR using 1-octene as an internal standard.

(Hydroxypyridine ligands (entries 6 and 7) were synthesized according to procedures known in the art. The amino acid based ligands are either commercially available or known compounds.)

Example 48

Meta-C—H Arylation of the PyA-Attached Alcohol:

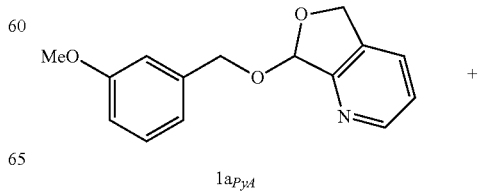

71
-continued

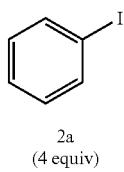

2a
(4 equiv)

Pd(OAc)$_2$ (10 mol %)
Ac-Gly-OH (20 mol %)
NBE-CO$_2$Me (1.5 equiv)
AgOAc(4 equiv)
———————————————→
DCE, 100° C., 46 h
15% NMR yield
(+59% yield rsm)

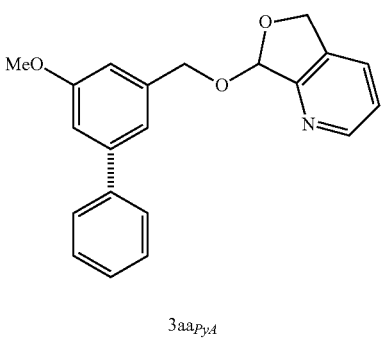

3aa$_{PyA}$

A 2-dram vial with a PTFE-lined cap was charged with acetal 1a$_{PyA}$ (25.4 mg, 0.0988 mmol), PhI (82.6 mg, 0.405 mmol), NBE-CO$_2$Me (22.3 mg, 0.1497 mmol), Pd(OAc)$_2$ (2.2 mg, 0.00982 mmol), Ac-Gly-OH (2.2 mg, 0.0188 mmol), AgOAc (66.7 mg, 0.399 mmol), and DCE (2.00 mL). The resulting mixture was heated to 100° C. and stirred for 46 h. After cooling to room temperature, the mixture was filtered through a plug of silica gel, eluting with EtOAc (30.0 mL). The filtrate was concentrated under reduced pressure to afford arylation product 3aa$_{PyA}$ (15% NMR yield+59% NMR yield recovery of acetal 1a$_{PyA}$, measured using 1-octene as an internal standard).

Arylation product 3aa$_{PyA}$: $^1$H NMR: (selected peaks) (400 MHz, CDCl$_3$) δ 6.19 (d, J=1.9 Hz, 1H), 3.79 (s, 3H).

The arylation using 1a$_{PyA}$ did not improve significantly using Pd(TFA)$_2$.

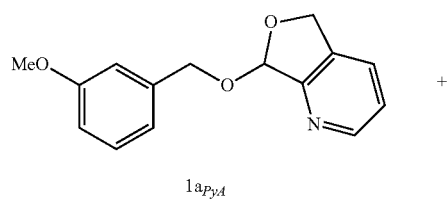

1a$_{PyA}$

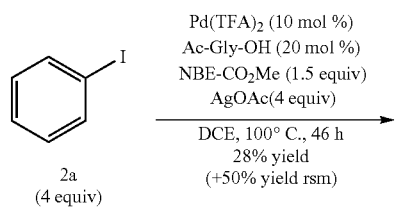

2a
(4 equiv)

Pd(TFA)$_2$ (10 mol %)
Ac-Gly-OH (20 mol %)
NBE-CO$_2$Me (1.5 equiv)
AgOAc(4 equiv)
———————————————→
DCE, 100° C., 46 h
28% yield
(+50% yield rsm)

72
-continued

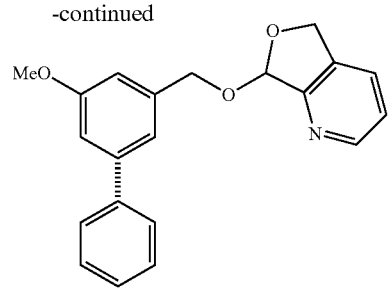

3aa$_{PyA}$

A 2-dram vial with a PTFE-lined cap was charged with acetal 1a$_{PyA}$ (27.0 mg, 0.105 mmol), PhI (82.4 mg, 0.404 mmol), NBE-CO$_2$Me (22.6 mg, 0.149 mmol), Pd(TFA)$_2$ (3.3 mg, 0.00994 mmol), Ac-Gly-OH (2.3 mg, 0.0197 mmol), AgOAc (65.5 mg, 0.392 mmol), and DCE (2.00 mL). The resulting mixture was heated to 100° C. and stirred for 46 h. After cooling to room temperature, ethylenediamine (0.100 mL) was added, and the resulting mixture was stirred at 23° C. for 2 h. The mixture was filtered through a plug of silica gel, eluting with EtOAc (30 mL), and the filtrate was concentrated under reduced pressure. The residue was purified by preparative TLC (1:1 hexanes/EtOAc eluent) to afford arylation product 3aa$_{PyA}$ (21.9 mg, 28% yield+50% yield recovered 1a$_{PyA}$, R$_f$=0.27 in 1:1 hexanes/EtOAc) as a yellow oil.

Example 49

Formation and Characterization of the Benzocyclobutene Byproduct:

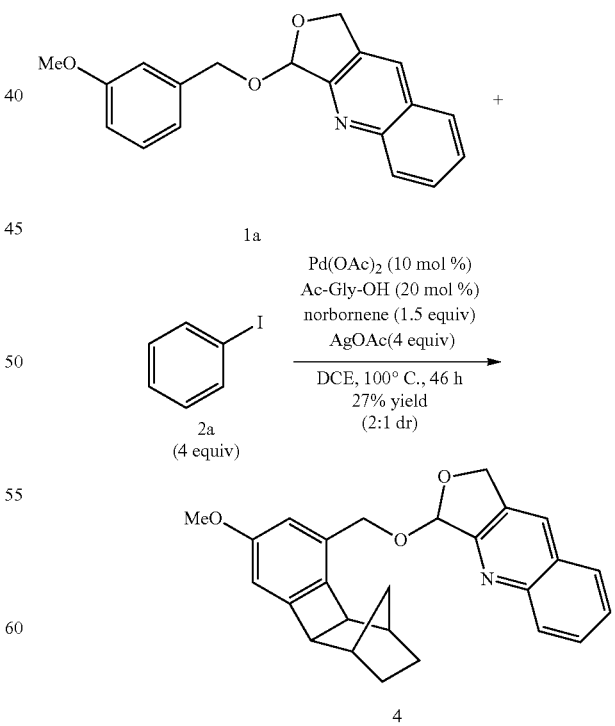

To a 2-dram vial with a PTFE-lined cap was charged with acetal 1a (0.500 mL, 0.100 M in DCE, 0.0500 mmol), PhI (40.1 mg, 0.197 mmol), norbornene (7.8 mg, 0.0830 mmol), Pd(OAc)$_2$ (1.1 mg, 0.00491 mmol), Ac-Gly-OH (1.2 mg, 0.0103 mmol), AgOAc (34.4 mg, 0.206 mmol), and DCE (0.500 mL). The resulting mixture was heated to 100° C. and stirred for 46 h. After cooling to room temperature, the mixture was filtered through a plug of silica gel, eluting with EtOAc (30 mL), and the filtrate was concentrated under reduced pressure. The residue was purified by preparative TLC (2:1 hexanes/EtOAc eluent) to afford benzocyclobutene byproduct 4 (5.4 mg, 27% yield, R$_f$=0.47 in 2:1 hexanes/EtOAc) as a light yellow oil. (4% yield of arylation product 3aa and 44% recovery of starting material 1a were observed in the crude NMR prior to purification.)

$^1$H NMR: (400 MHz, CDCl$_3$) δ 8.17 (d, J=8.5 Hz, 1H), 8.05 (s, 1H), 7.85 (d, J=8.1 Hz, 1H), 7.73 (app. t, J=7.6 Hz, 1H), 7.58 (app. t, J=7.5 Hz, 1H), 6.84 (s, 1H), 6.51 (s, 1H), 6.284 (s, 0.67H), 6.276 (s, 0.33H), 5.39 (d, J=13.2 Hz, 1H), 5.23 (d, J=13.2 Hz, 1H), 4.87-4.73 (m, 2H), 3.76 (s, 3H), 3.19 (d, J=3.7 Hz, 0.33H), 3.13 (d, J=3.7 Hz, 0.67H), 3.09 (app. t, J=4.2 Hz, 1H), 2.30 (s, 1H), 2.21 (s, 1H), 1.58-1.50 (m, 2H), 1.18-1.11 (m, 2H), 0.95-0.79 (m, 2H).

$^{13}$C NMR: (125 MHz, CDCl$_3$) δ 160.23, 160.21, 159.7, 148.7, 147.4, 147.3, 137.0, 136.9, 133.30, 133.26, 130.80, 130.77, 130.00, 129.98, 129.6, 128.99, 128.98, 128.1, 128.0, 127.2, 125.7, 112.72, 112.71, 107.59, 107.55, 103.6, 103.5, 70.11, 70.09, 67.1, 67.0, 55.7, 50.0, 49.9, 49.19, 49.16, 36.71, 36.66, 36.6, 32.30, 32.26, 30.5, 28.01, 27.98, 27.96.

IR: (film) 2948, 2868, 1471, 1020, 1009 cm$^{-1}$.

HRMS: (ESI+) m/z calc'd for (M+H)$^+$ [C$_{26}$H$_{25}$NO$_3$+H]$^+$: 400.1907, found 400.1910.

What is claimed is:

1. A method of meta-arylating an arene alcohol, the method comprising the steps of:
   (a) replacing a benzoate group of a quinolinyl hemiacetal benzoate with an aromatic alcohol or a substituted aromatic alcohol wherein the aromatic alcohol or a substituted aromatic alcohol has the formula II:

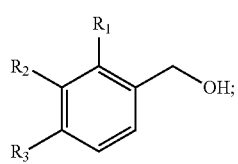

thereby forming form a compound of formula III:

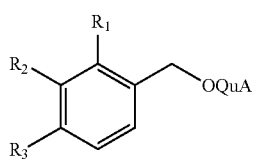

(b) reacting the compound of formula III with an aryl iodide having the formula I:

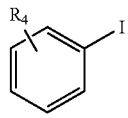

in the presence of a palladium trifluoroacetate catalyst, silver acetate, trifluoroacetylglycine, and carboxymethyl norbornene to generate a meta-arylated arene-quinolinyl hemiacetal scaffold conjugate; and (c) incubating the meta-arylated arene-quinolinyl hemiacetal scaffold conjugate of step (b) with an alkyl alcohol under acid conditions to generate an alkylated quinolinyl hemiacetal scaffold having the formula V:

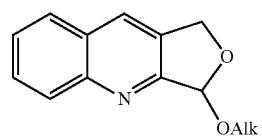

and a meta-arylated arene alcohol having the formula VI:

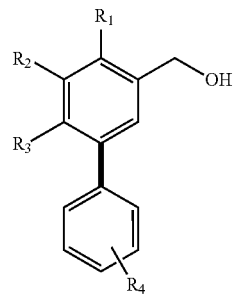

wherein:
   R$_1$, R$_2$, or R$_3$ are independently selected from the group consisting of: H, a halogen, an alkyl, a substituted alkyl, an aryl, a substituted aryl, an amino group, a substituted amino group, an alkoxy group, a heterocyclic group, R$_1$ and R$_2$ are linked to form a cyclic group and R$_2$ and R$_3$ are linked to form a cyclic group; and
   R$_4$ is selected from the group consisting of: H, a halogen, an alkyl, an alkoxy, a carboxyalkyl, an alkylbenzoate, a substituted amine, an ether group, a ketone group, an ester group, a carbamate group, a nitro group, and a halogenated alkyl group.

2. The method of claim 1, wherein the aryl iodide is an alkyliodobenzoate.

3. The method of claim 2, wherein the alkyliodobenzoate is methyliodobenzoate.

* * * * *